(12) United States Patent
Noguera et al.

(10) Patent No.: US 11,028,418 B2
(45) Date of Patent: Jun. 8, 2021

(54) MICROORGANISMS AND METHODS FOR PRODUCING 2-PYRONE-4,6-DICARBOXYLIC ACID AND OTHER COMPOUNDS

(71) Applicant: WISCONSIN ALUMNI RESEARCH FOUNDATION, Madison, WI (US)

(72) Inventors: Daniel R. Noguera, Madison, WI (US); Timothy James Donohue, Middleton, WI (US); Jose Perez, Madison, WI (US); Wayne S. Kontur, Madison, WI (US); German Eduardo Umana Chapeton, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/795,111

(22) Filed: Feb. 19, 2020

(65) Prior Publication Data
US 2020/0263215 A1 Aug. 20, 2020

Related U.S. Application Data

(60) Provisional application No. 62/808,030, filed on Feb. 20, 2019.

(51) Int. Cl.
| | |
|---|---|
| *C12N 9/00* | (2006.01) |
| *C12P 17/06* | (2006.01) |
| *C12N 15/52* | (2006.01) |
| *C12N 9/18* | (2006.01) |
| *C12N 1/20* | (2006.01) |
| *C12N 9/90* | (2006.01) |
| *C12N 9/10* | (2006.01) |

(52) U.S. Cl.
CPC ............... *C12P 17/06* (2013.01); *C12N 1/20* (2013.01); *C12N 9/1007* (2013.01); *C12N 9/18* (2013.01); *C12N 9/90* (2013.01); *C12Y 301/01057* (2013.01)

(58) Field of Classification Search
CPC ........ C12P 7/22; C12N 9/1007; C12N 9/0073
See application file for complete search history.

(56) References Cited

U.S. PATENT DOCUMENTS

| | | | |
|---|---|---|---|
| 10,144,938 B2 | 12/2018 | Noguera | |
| 2016/0312257 A1 | 10/2016 | Noguera | |
| 2019/0048329 A1 | 2/2019 | Donohue | |
| 2019/0153485 A1* | 5/2019 | Beckham | ................. C12N 9/90 |
| 2020/0017891 A1 | 1/2020 | Donohue | |

OTHER PUBLICATIONS

Altschul et al. *Journal of Molecular Biology.* 1990. 215:403-410.
Austin, S., Kontur, W.S., Ulbrich, A., Oshlag, J.Z., Zhang, W., Higbee, A., Zhang, Y., Coon, J.J., Hodge, D.B., Donohue, T.J. and Noguera, D.R., *Environmental Science & Technology.* 2015. 49, 8914-8922.
Ausubel, F.M. et al. "Current Protocols in Molecular Biology." Eds., Current Protocols, a joint venture between Greene Publishing Associates, Inc. and John Wiley & Sons, Inc. Supplemented through 2008. (Book—Copy Not Provided).
Beckham, G.T., Johnson, C.W., Karp, E.M., Salvachua, D. and Vardon, D.R., *Current Opinion in Biotechnology.* 2016. 42, 40-53.
Bhalla, A., Bansal, N., Stoklosa, R., Fountain, M., Ralph, J., Hodge, D. and Hegg, E., *Biotechnology for Biofuels.* 2016. 9, 34.
Bugg, T.D., Ahmad, M., Hardiman, E.M. and Rahmanpour, R., *Natural Product Reports.* 2011. 28, 1883-1896.
Cecil, J.H., Garcia, D.C., Giannone, R.J. and Michener, J.K., *Applied and Environmental Microbiology.* 2018. 84, 1-13.
D'Argenio, V., Notomista, E., Petrillo, M., Cantiello, P., Cafaro, V., Izzo,V., Naso, B., Cozzuto, L., Durante, L., Troncone, L., Paolella, G., Salvatore, F. and Di Donato, A., *BMC Genomics.* 2014. 15:384.
Das, A., Rahimi, A., Ulbrich, A., Alherech, M., Motagamwala, A.H., Bhalla, A., Da Costa Sousa, L., Balan, V., Dumesic, J., Hegg, E.L., Dale, B.E., Ralph, J., Coon, J.J. and Stahl, S.S., *ACS Sustainable Chemistry & Engineering.* 2018. 6, 3, 3367-3374.
Fredrickson, J.K., Balkwill, D.L., Drake, G.R., Romine, M.F., Ringelberg, D.B. and White, D.C. *Applied and Environmental Microbiology.* 1995. 61, 1917-1922.
Fuchs, G., Boll, M. and Heider, J., *Nature Reviews Microbiology.* 2011. 9, 803-816.
Gall, D.L., Ralph, J., Donohue, T.J. and Noguera, D.R., *Current Opinion in Biotechnology.* 2017. 45, 120-126.
Green et al. "Molecular Cloning: A laboratory manual." 4th edition. Cold Spring Harbor Laboratory Press. 2012 (Book—Copy Not Provided).
Harris, P.J. and Hartley, R.D., *Biochemical Systematics and Ecology.* 1980. 8, 153-160.
Harris, P.J. and Hartley, R.D., *Nature.* 1976. 259, 508.
Henikoff & Henikoff, *Proceedings of the National Academy of Sciences of the United States of America.* 1992. 89:10915.

(Continued)

*Primary Examiner* — Maryam Monshipouri
(74) *Attorney, Agent, or Firm* — Daniel A. Blasiole; DeWitt LLP

(57) ABSTRACT

Recombinant microorganisms configured for enhanced production of compounds such as 2-pyrone-4,6-dicarboxylic acid (PDC) and methods of using the recombinant microorganisms for the production of these compounds. The recombinant microorganisms include one or more modifications that reduce 2-pyrone-4,6-dicarboxylic acid (PDC) hydrolase activity, 4-carboxy-2-hydroxy-6-methoxy-6-oxohexa-2,4-dienoate (CHMOD) cis-trans isomerase activity, 4-carboxy-2-hydroxy-6-methoxy-6-oxohexa-2,4-dienoate (CHMOD) methyl esterase activity, and/or vanillate/3-O-methylgallate O-demethylase activity. The recombinant microorganisms can be used to generate PDC from media comprising plant-derived phenolics, such as syringyl phenolics, guaiacyl phenolics, and p-hydroxyphenyl phenolics. The plant-derived phenolics can be derived from pretreated lignin, including depolymerized lignin or other chemically altered lignin.

10 Claims, 39 Drawing Sheets
(39 of 39 Drawing Sheet(s) Filed in Color)
Specification includes a Sequence Listing.

(56) References Cited

OTHER PUBLICATIONS

Jørgensen, H., Kristensen, J.B. and Felby, C., *Biofuels, Bioproducts and Biorefining*. 2007. 1(2), 119-134.
Kamimura, N., Takahashi, K., Mori, K., Araki, T., Fujita, M., Higuchi, Y. and Masai, E., *Environmental Microbiology*. 2017. 9, 679-705.
Karlen, SD, Fasahati, P, Mazaheri, M, Serate, J, Smith, RA, Sirobhushanam, S, Chen, M, Tymkhin, VI, Cass, CL, Liu, S, Padmakshan, D, Xie, D, Zhang, Y, McGee, MA, Russell, JD, Coon, JJ, Kaeppler, HF, De Leon, N, Maravelias, CT, Runge, TM, Kaeppler, SM, Sedbrook, JC, Ralph, J. Assessing the viability of recovering hydroxycinnamic acids from lignocellulosic biorefinery alkaline pretreatment waste of streams. *ChemSusChem*. Jan. 26, 2020.
Karlin & Altschul, *Proceedings of the National Academy of Sciences of the United States of America*. 1993. 90:5873-5877.
Kasai, D., Masai, E., Katayama, Y. and Fukuda, M., *FEMS Microbiology Letters*. 2007. 274, 323-328.
Kasai, D., Masai, E., Miyauchi, K., Katayama, Y. and Fukuda, M., *Journal of Bacteriology*. 2004. 186, 4951-4959.
Kontur, W.S., Bingman, C.A., Olmsted, C.N., Wassarman, D.R., Ulbrich, A., Gall, D.L., Smith, R.W., Yusko, L.M., Fox, DB.G., Noguera, R., Coon, J.J. and Donohue, T.J., *Journal of Biological Chemistry*. 2018. 293, 4955-4968.
Kumar AK and Sharma S. Recent Updates on Different Methods of Pretreatment of Lignocellulosic Feedstocks: A Review. *Bioresources and Bioprocessing*. 2017. 4:7.
Kumar, P.; Barrett, D. M.; Delwiche, M. J.; Stroeve, P., Methods for Pretreatment of lignocellulosic Biomass for Efficient Hydrolysis and Biofuel Production. *Industrial & Engineering Chemistry Research*. 2009. 48, (8), 3713-3729.
Li, Y. et al., Kinetic and mechanistic insights into hydrogenolysis of lignin to monomers in a continuous flow reactor. *Green Chem*., 2019, 21, 3561.
Li, Z., Chen, C.H., Liu, T., Mathrubootham, V., Hegg, E.L. and Hodge, D.B., *Biotechnology and Bioengineering*. 2013. 110, 1078-1086.
Linger, J.G., Vardon, D.T., Guarnieri, M.T., Karp, E.M., Hunsinger, G.B., Franden, M.A., Johnson, C.W., Chupka, G., Strathmann, T.J., Pienkos, P.T. and Beckham, G.T., *Proceedings of the National Academy of Sciences of the United States of America*. 2014. 111, 12013-12018.
Masai, E., Katayama, Y. and Fukuda, M. *Bioscience, Biotechnology, and Biochemistry*. 2007. 71, 1-15.
Masai, E., Shinohara, S., Hara, H., Nishikawa, S., Katayama, Y. and Fukuda, M., *Journal of Bacteriology*. 1999. 181, 55-62.
Michinobu, T., Bito, M., Yamada, Y., Katayama, Y., Noguchi, K., Masai, E., Nakamura, M., Ohara, S. and Shigehara, K. *Bulletin of the Chemical Society of Japan*. 2007. 80, 2436-2442.
Michinobu, T., Hishida, M., Sato, M., Katayama, Y., Masai, E., Nakamura,M., Otsuka, Y., Ohara, S. and Shigehara, K., *Polymer Journal*. 2008. 40, 68-75.
Mitchell, V.D., Taylor, C.M. and Bauer, S., *BioEnergy Research*. 2014. 7, 654-669.
Mycroft, Z., Gomis, M., Mines, P., Law, P. and Bugg, T.D.H., *Green Chem*. 2015. 17, 4974-4979.
Needleman & Wunsch, *Journal of Molecular Biology*. 1970. 48:443.
Okamura-Abe, Y., Abe, T., Nishimura, K., Kawata, Y., Sato-Izawa, K., Otsuka, M. Nakamura, S. Kajita, E. Masai, T. Sonoki and Y. Katayama, Y., *Journal of Bioscience and Bioengineering*. 2016. 121, 652-658.
Olins et al. *Journal of Biological Chemistry*. 1989. 264(29):16973-16976.
Otsuka, Y., Nakamura, M., Shigehara, K., Sugimura, K., Masai, E., Ohara, S. and Katayama, Y. *Applied Microbiology and Biotechnology*. 2006. 71, 608-614.
Pandey MP, Kim CS., Lignin Depolymerization and Conversion: A Review of Thermochemical Methods. *Chemical & Engineering Technology*. 2011. vol. 34, Issue 1, pp. 29-41.
Pearson & Lipman, *Proceedings of the National Academy of Sciences of the United States of America*. 1988. 85:2444.
Perez, Jose M. and Kontur, Wayne S. and Alherech, Manar and Coplien, Jason and Karlen, Steven D. and Stahl, Shannon S. and Donohue, Timothy J. and Noguera, Daniel R., Funneling aromatic products of chemically depolymerized lignin into 2-pyrone-4-6-dicarboxylic acid with Novosphingobium aromaticivorans. *Green Chemistry*. 2019. 21(6):1340-1350.
Qian, Y., Otsuka, Y., Sonoki, T., Mukhopadhyay, B., Nakamura, M., Jellison, J. and Goodell, B., *BioResources*. 2016. 11, 6097-6109.
Ragauskas, A.J., Beckham, G.T., Biddy, M.J., Chandra, R., Chen, F., Davis,M.F., Davison, B.H., Dixon, R.A., Gilna, P., Keller, M., Langan, P., Naskar, A.K., Saddler, J.N., Tschaplinski, T.J., Tuskan, G.A. and Wyman, C.E., *Science*. 2014. 344, 1246843.
Rahimi, A., Ulbrich, A., Coon. J.J. and Stahl, S.S., *Nature*. 2014. 515, 249-252.
Ralph, J., Brunow, G. and Boerjan. W., *eLS*. 2007.
Sainsbury, P.D., Hardiman, E.M., Ahmad, M., Otani, H., Seghezzi, N., Eltis, L.D. and Bugg, T.D.H., *ACS Chemical Biology*. 2013. 8, 2151-2156.
Sambrook et al. "Molecular Cloning: A Laboratory Manual." 3rd edition. Cold Spring Harbor Laboratory Press. 2001. (Book—Copy Not Provided).
Schäfer, A., Tauch, A., Jäger, W., Kalinowski, J., Thierbach, G. and Pühler, A., *Gene*. 1994. 145, 69-73.
Schutyser, W., Renders, T., Van Den Bosch, S., Koelewijn, S.F., Beckham, G.T. and Sels, B.F., *Chemical Society Reviews*. 2018. 47, 852-908.
Shikinaka, K., Otsuka, Nakamura, M., Masai, E. and Katayama, Y., *Journal of Oleo Science*. 2018. 67, 1059-1070.
Simon, R., Priefer, U. and Pühler, A., *Bio/Technology*. 1983. 1, 784.
Sistrom, S.R., *The Journal of General Microbiology*. 1962. 28, 607-616.
Smith & Waterman. *Advances in Applied Mathematics*. 1981. 2:482.
Smith, D.C.C., *Nature*. 1955. 176, 267.
Sun, Z., Fridrich, B., De Santi, A., Elangovan, S. and Barta, K., *Chemical Reviews*. 2018. 118, 614-678.
Sze, I.S. and Dagley, S., *Journal of Bacteriology*. 1987. 169, 3833-3835.
Taylor, R.G., Walker, D.C. and McLnnes, R.R., *Nucleic Acids Research*. 1993. 21, 1677-1678.
Vanholme, R., Morreel, K., Darrah, C., Oyarce, P., Grabber, J.H., Ralph, J. and Boerjan, W., *New Phytologist*. 2012. 196, 978-1000.
Vardon, D., Franden, M.A., Johnson, C., Karp, E., Guarnieri, M., Linger, J., Salm, M., Strathmann, T., Beckham. G. and Ferguson, G., *Energy & Environmental Science*. 2015. 8, 617-628.
Vogel, J., *Current Opinion in Plant Biology*. 2008. 11, 301-307.
Wang H, Tucker M, Ji Y, Recent Development in Chemical Depolymerization of Lignin: A Review. *Journal of Applied Chemistry*. 2013. vol. 2013, Article ID 838645. 2013:1-9.
Zakzeski, J., Bruijnincx, P.C.A., Jongerius, A.L. and Weckhuysen, B.M., *Chemical Reviews*. 2010. 110, 3552-3599.

* cited by examiner

US 11,028,418 B2

MICROORGANISMS AND METHODS FOR PRODUCING 2-PYRONE-4,6-DICARBOXYLIC ACID AND OTHER COMPOUNDS

STATEMENT REGARDING FEDERALLY SPONSORED RESEARCH

This invention was made with government support under DE-FC02-07ER64494 and DE-SC0018409 awarded by the US Department of Energy. The government has certain rights in the invention.

SEQUENCE LISTING

The instant application contains a Sequence Listing which has been submitted in ASCII format via EFS-Web and is hereby incorporated by reference in its entirety. The ASCII copy, created on Feb. 14, 2020, is named USPTO-200219-Nonprovisional_Patent_Application-P180219US02-SEQ_LIST.txt and is 55,014 bytes in size.

FIELD OF THE INVENTION

The invention is directed to recombinant microorganisms configured for enhanced production of compounds such as 2-pyrone-4,6-dicarboxylic acid (PDC) and methods of using the recombinant microorganisms for the production of these compounds.

BACKGROUND

Plant biomass contains three main types of natural polymers: cellulose, hemicellulose, and lignin. Lignin is a heteropolymer of phenylpropanoids containing 4-hydroxy (H); 3-methoxyphenyl (G); and 3,5-dimethoxyphenyl (S) units in different proportions among plant species. Hardwoods contain between 18% and 25% lignin, with mostly G and S units. Softwoods contain between 25% and 35% lignin, with predominantly G and H units. Grasses contain between 10% and 30% lignin, with G, S, and H units present in similar proportions. Chemical lignin depolymerization treatments can produce diverse aromatic compounds that conserve the original H, G, and S units, with varying substitutions of the alkyl side chain.

This invention shows that 2-pyrone-4,6-dicarboxylic acid (PDC) is a metabolic intermediate of the biological catabolism of numerous lignocellulose-derived aromatic compounds containing H, G, and S units. PDC can be used as a natural building block and additive to plastic polymers and also shows a strong and unique binding capacity for certain metals.

Previous attempts to engineer bacterial strains to produce PDC have resulted in microorganisms able to convert selected single aromatic compounds or defined mixtures of a few compounds into PDC. The attempts have involved the addition of selected genes to bacterial strains that can allow aromatic compounds to pass through the cellular membrane but cannot naturally process them. Although these strategies have been effective in transforming selected aromatic compounds into PDC, no effective biological method is currently available to convert a wide range of biomass-derived aromatic compounds, including G, H, and S units plus others, into PDC.

Microorganisms and methods for converting a wide range of biomass-derived aromatic compounds into PDC are needed.

SUMMARY OF THE INVENTION

The invention is directed to recombinant microorganisms configured for enhanced production of compounds such as 2-pyrone-4,6-dicarboxylic acid (PDC) and methods of using the recombinant microorganisms for the production of these compounds.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
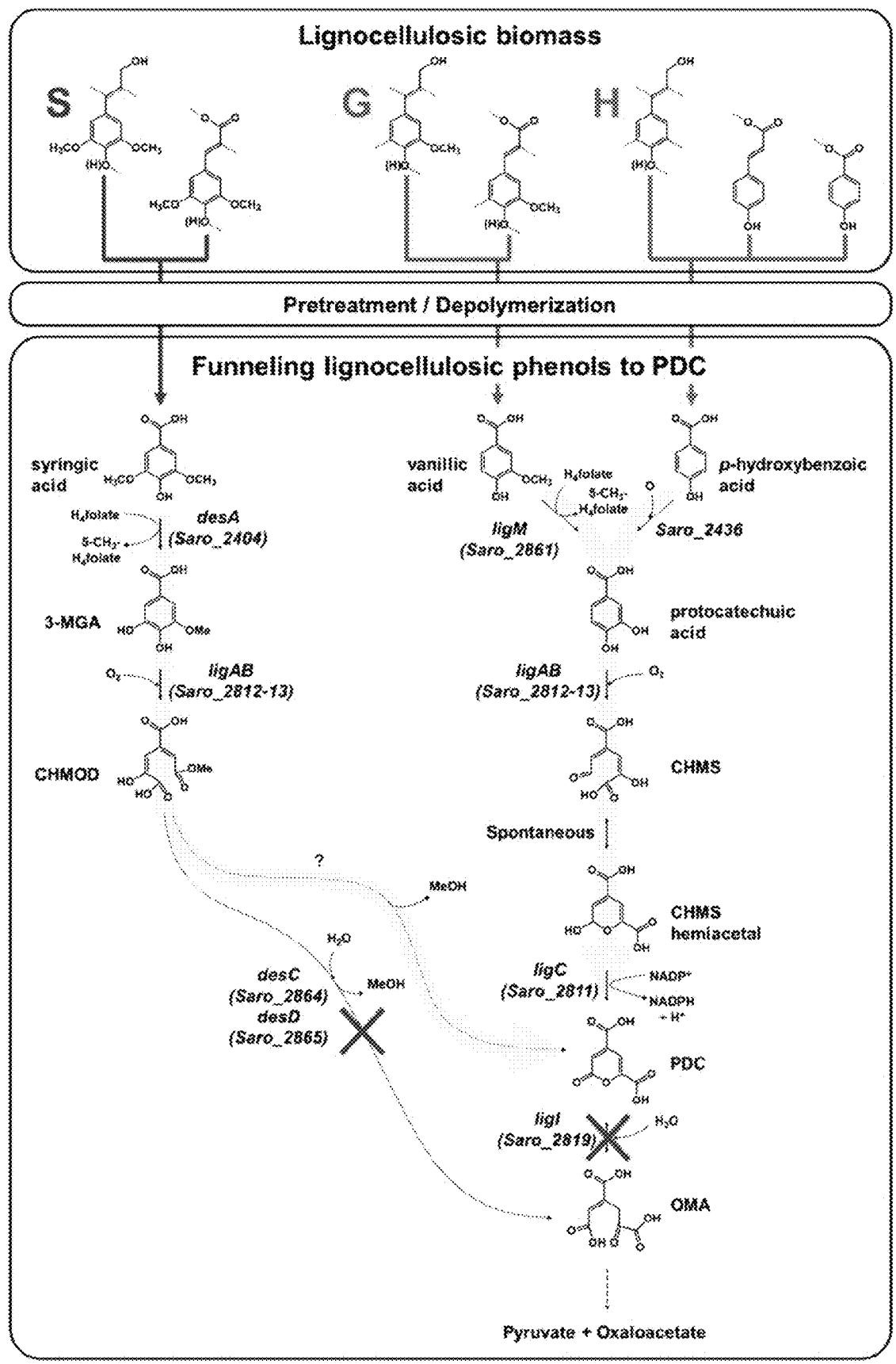
FIG. 1. Predicted pathways of S unit (syringic acid), G unit (vanillic acid), and H unit (p-hydroxybenzoic acid) metabolism in *N. aromaticivorans* DSM12444. In this model, deletions of the genes ligI (Saro_2819), desC (Saro_2864), and desD (Saro_2865) are hypothesized to enable the funneling (represented by light blue arrows) of S, G, and H lignocellulosic biomass-derived aromatic compounds into 2-pyrone-4,6-dicarboxylic acid (PDC). Abbreviations: 3-methylgallic acid, 3-MGA; 4-carboxy-2-hydroxy-6-methoxy-6-oxohexa-2,4-dienoate, CHMOD; 4-carboxy-2-hydroxy-cis,cis-muconate-6-semialdehyde, CHMS; 4-oxalomesaconate, OMA.

One aspect of the invention is directed to recombinant microorganisms. The recombinant microorganisms of the invention can be configured for enhanced production of 2-pyrone-4,6-dicarboxylic acid (PDC) or other compounds. The recombinant microorganisms of the invention comprise one or more modifications that reduce the activity of one or more genes or gene products, increase the activity of one or more genes or gene products, or reduce the activity of one or more genes or gene products and increase the activity of one or more genes or gene products. The recombinant microorganisms with the modifications can exhibit enhanced production or 2-pyrone-4,6-dicarboxylic acid (PDC) or other compounds with respect to corresponding microorganisms not comprising the modifications.

"Modifications that reduce the activity of one or more genes or gene products" refers to any modification to a microorganism that decreases or ablates expression of the gene and thus production of the gene product and/or decreases or ablates the functioning of the gene product per se. Decreasing or ablating the functioning of a gene product may comprise decreasing or ablating the specific activity of a gene product. Exemplary modifications that reduce the activity of one or more genes or gene products include genetic modifications. The genetic modifications include mutations to a gene that decrease or ablate expression of the gene in producing the gene product. Such mutations may include mutations to the coding sequence, the promoter, an enhancer, or any other part of the gene. The genetic mutations also include mutations to the coding sequence of a gene that decrease or ablate the functioning of a gene product expressed from the gene. The genetic mutations also include recombinant nucleotide sequences configured to express antisense RNAs or other molecules that decrease or ablate production of a gene product. The genetic modifications also include mutations to a first gene (such as a transcription factor or an inhibitor of a transcription factor) that affects the expression of a second gene. Other genetic modifications are described elsewhere herein. Unless explicitly stated otherwise or indicated from the context, reference to a modification that reduces the activity of any named gene (e.g., "LigI," "Saro_1879") or homolog thereof encompasses any modification that decreases the activity (e.g., expression and/or functionality) of the gene or homolog thereof and/or the gene product of the gene or homolog thereof, as described above and elsewhere herein.

"Modifications that increase the activity of one or more genes or gene products" refers to any modification to microorganism that increases expression of a gene in producing its gene product or increases the functioning of the gene product. "Increase" in this context refers to increasing beyond a positive baseline activity or increasing beyond null activity and thereby introducing a new activity. Exemplary modifications that increase the activity of one or more genes or gene products include genetic modifications. The genetic modifications include genetic modifications to a gene in a manner that increases expression of the gene in producing the gene product. Such modifications include operationally connecting the coding sequence to a stronger promoter or enhancer, etc., and/or introducing additional copies of the gene (whether the native gene or a recombinant version). The genetic modifications also include mutations to a first gene (such as a transcription factor or an inhibitor of a transcription factor) that affects the expression of a second gene. The genetic modifications also include one or more copies of a gene introduced into the microorganism. Other genetic modifications are described herein. Any modifications described herein can comprise recombinant genes. Unless explicitly stated otherwise or indicated from the context, reference to a modification that increases the activity of any named gene (e.g., "ligC," "Saro_2811") or homolog thereof encompasses any modification that increases the activity (e.g., expression and/or functionality) of the gene or homolog thereof and/or the gene product of the gene or homolog thereof, as described above and elsewhere herein.

"Corresponding microorganism" refers to a microorganism of the same species having the same or substantially same genetic and proteomic composition as a recombinant microorganism of the invention, with the exception of genetic and proteomic differences resulting from the modifications described herein for the recombinant microorganisms of the invention. In some versions, the corresponding microorganism is the native version of the recombinant microorganism of the invention, i.e., the unmodified microorganism as found in nature. The terms "microorganism" and "microbe" are used interchangeably herein.

In some versions, the recombinant microorganisms comprise one or more modifications with respect to a corresponding microorganism not comprising the one or more modifications. The one or more modifications can comprise a modification selected from the group consisting of a modification that reduces 2-pyrone-4,6-dicarboxylic acid (PDC) hydrolase activity with respect to the corresponding microorganism, a modification that reduces 4-carboxy-2-hydroxy-6-methoxy-6-oxohexa-2,4-dienoate (CHMOD) cis-trans isomerase activity with respect to the corresponding microorganism, a modification that reduces CHMOD methyl esterase activity with respect to the corresponding microorganism, a modification that reduces vanillate/3-O-methylgallate O-demethylase activity with respect to the corresponding microorganism, a modification that increases syringic acid O-demethylase activity with respect to the corresponding microorganism, a modification that increases aromatic 4,5 dioxygenase activity with respect to the corresponding microorganism, a modification that increases p-hydroxybenzoic acid 3-monooxygenase activity with respect to the corresponding microorganism, and a modification that increases 4-carboxy-2-ydroxy-cis,cis-muconate-6-semialdehyde (CHMS) dehydrogenase activity with respect to the corresponding microorganism.

PDC hydrolase activity comprises the ability to hydrolyze PDC to produce 4-oxalomesaconate (OMA). An exemplary PDC hydrolase is ligI/LigI (Saro_2819) of *Novosphingobium aromaticivorans*, the nucleic acid coding sequence of which is SEQ ID NO:1 and the protein sequence of which is SEQ ID NO:2. Homologs of the ligI/LigI of *Novosphingobium aromaticivorans* are known in other organisms. In some versions of the invention, the one or more modifications in the recombinant microorganisms can comprise a genetic modification that reduces PDC hydrolase activity. A genetic modification that reduces PDC hydrolase activity can comprise a genetic modification to a PDC hydrolase gene. A genetic modification to a PDC hydrolase gene can comprise a substitution or insertion in or a complete or partial deletion of the PDC hydrolase gene. In some versions, the one or more modifications in the recombinant microorganisms can comprise a modification that reduces activity of ligI or a homolog thereof. A modification that reduces activity of ligI or a homolog thereof can comprise a genetic modification of ligI or a homolog thereof. A genetic modification of ligI or a homolog thereof can comprise a substitution or insertion in or a complete or partial deletion of ligI or a homolog thereof.

CHMOD cis-trans isomerase activity comprises the ability to isomerize stereoisomers of CHMOD. An exemplary CHMOD cis-trans isomerase is desD/DesD (Saro_2865) of *Novosphingobium aromaticivorans*, the nucleic acid coding sequence of which is SEQ ID NO:3 and the protein sequence of which is SEQ ID NO:4. Homologs of the desD/DesD of *Novosphingobium aromaticivorans* are known in other organisms. In some versions of the invention, the one or more modifications in the recombinant microorganisms can comprise a genetic modification that reduces CHMOD cis-trans isomerase activity. A genetic modification that reduces CHMOD cis-trans isomerase activity can comprise a genetic modification to a CHMOD cis-trans isomerase gene. A genetic modification to a CHMOD cis-trans isomerase gene can comprise a substitution or insertion in or a complete or partial deletion of the CHMOD cis-trans isomerase gene. In some versions, the one or more modifications in the recombinant microorganisms can comprise a modification that reduces activity of desD or a homolog thereof. A modification that reduces activity of desD or a homolog thereof can comprise a genetic modification of desD or a homolog thereof. A genetic modification of desD or a homolog thereof can comprise a substitution or insertion in or a complete or partial deletion of desD or a homolog thereof.

CHMOD methyl esterase activity comprises the ability to demethylate CHMOD to produce OMA. An exemplary CHMOD methyl esterase is desC/DesC (Saro_2864) of *Novosphingobium aromaticivorans*, the nucleic acid coding sequence of which is SEQ ID NO:5 and the protein sequence of which is SEQ ID NO:6. Homologs of the desC/DesC of *Novosphingobium aromaticivorans* are known in other organisms. In some versions of the invention, the one or more modifications in the recombinant microorganisms can comprise a genetic modification that reduces CHMOD methyl esterase activity. A genetic modification that reduces CHMOD methyl esterase activity can comprise a genetic modification to a CHMOD methyl esterase gene. A genetic modification to a CHMOD methyl esterase gene can comprise a substitution or insertion in or a complete or partial deletion of the CHMOD methyl esterase gene. In some versions, the one or more modifications in the recombinant microorganisms can comprise a modification that reduces activity of desC or a homolog thereof. A modification that reduces activity of desC or a homolog thereof can comprise a genetic modification of desC or a homolog thereof. A genetic modification of desC or a homolog thereof can comprise a substitution or insertion in or a complete or partial deletion of desC or a homolog thereof.

Vanillate/3-O-methylgallate O-demethylase activity comprises the ability to O-demethylate substrates such as vanillate and/or 3-methoxygallic acid. Vanillate/3-O-methylgallate O-demethylases include enzymes having activity characterized under one more of Enzyme Commission (EC) Numbers 2.1.1.341 and 1.14.13.82. An exemplary vanillate/3-O-methylgallate O-demethylase is ligM/LigM (Saro_2861) of *Novosphingobium aromaticivorans*, the nucleic acid coding sequence of which is SEQ ID NO:7 and the protein sequence of which is SEQ ID NO:8. Homologs of the ligM/LigM of *Novosphingobium aromaticivorans* are known in other organisms. Another exemplary vanillate/3-O-methylgallate O-demethylase is vanA/VanA (Saro_1872) of *Novosphingobium aromaticivorans*, the nucleic acid coding sequence of which is SEQ ID NO:9 and the protein sequence of which is SEQ ID NO:10. Homologs of the vanA/VanA of *Novosphingobium aromaticivorans* are known in other organisms. In some versions of the invention, the one or more modifications in the recombinant microorganisms can comprise a genetic modification that reduces vanillate/3-O-methylgallate O-demethylase activity. A genetic modification that reduces vanillate/3-O-methylgallate O-demethylase activity can comprise a genetic modification to a vanillate/3-O-methylgallate O-demethylase gene. A genetic modification to a vanillate/3-O-methylgallate O-demethylase gene can comprise a substitution or insertion in or a complete or partial deletion of the vanillate/3-O-methylgallate O-demethylase gene. In some versions, the one or more modifications in the recombinant microorganisms can comprise a modification that reduces activity of ligM, a homolog of ligM, vanA, a homolog of vanA, or a combination thereof. A modification that reduces activity of ligM, vanA, or homologs thereof can comprise a genetic modification of ligM, vanA, or homologs thereof. A genetic modification of ligM, vanA, or homologs can comprise a substitution or insertion in or a complete or partial deletion of ligM, vanA, or homologs thereof. Vanillate/3-O-methylgallate O-demethylases such as LigM can also react with 3-methylgallate as a substrate, and also likely with syringic acid. Vanillate/3-O-methylgallate O-demethylases such as VanA can also likely react with 3-methylgallate as a substrate.

Syringic acid O-demethylase activity comprises the ability to demethylate syringic acid to produce 3-methylgallate (3-MGA). An exemplary syringic acid O-demethylase is desA/DesA (Saro_2404) of *Novosphingobium aromaticivorans*, the nucleic acid coding sequence of which is SEQ ID NO:11 and the protein sequence of which is SEQ ID NO:12. Homologs of the desA/DesA of *Novosphingobium aromaticivorans* are known in other organisms. In some versions of the invention, the one or more modifications in the recombinant microorganisms can comprise a genetic modification that increases syringic acid O-demethylase activity. A genetic modification that increases syringic acid O-demethylase activity can comprise an introduction of a recombinant (genetically modified) syringic acid O-demethylase gene. The introduction of the recombinant syringic acid O-demethylase gene can occur by newly introducing a recombinant syringic acid O-demethylase gene to the microorganism or modifying a syringic acid O-demethylase gene already present in the microorganism. In some versions, the one or more modifications in the recombinant microorganisms can comprise a modification that increases activity of desA or a homolog thereof. A modification that increases activity of desA or a homolog thereof can comprise an introduction of a recombinant desA gene or a homolog thereof. The introduction of the recombinant desA gene or homolog thereof can occur by newly introducing a recombinant desA gene or homolog thereof to the microorganism or modifying a desA gene or homolog thereof already present in the microorganism. Syringic acid O-demethylases such as DesA may also react with vanillic acid as a substrate.

Aromatic 4,5 dioxygenase activity comprises the ability to catalyze ring opening of aromatic compounds such as 3-MGA and protocatechuic acid to produce compounds such as CHMOD and CHMS. An exemplary aromatic 4,5 dioxygenase is ligAB/LigAB (Saro_2813/2812; Saro_1233/1234) of *Novosphingobium aromaticivorans*. The nucleic acid coding sequence of the Saro_2813 ligA gene is SEQ ID NO:13, and the amino acid sequence of the Saro_2813 LigA subunit is SEQ ID NO:14. The nucleic acid coding sequence of the Saro_2812 ligB gene is SEQ ID NO:15, and the amino acid sequence of the Saro_2812 LigB subunit is SEQ ID NO:16. The nucleic acid coding sequence of the Saro_1233 ligA gene is SEQ ID NO:17, and the amino acid sequence of the Saro_1233 LigA subunit is SEQ ID NO:18. The nucleic acid coding sequence of the Saro_1234 ligB gene is SEQ ID NO:19, and the amino acid sequence of the Saro_1234 LigB subunit is SEQ ID NO:20. Homologs of the ligAB/LigAB of *Novosphingobium aromaticivorans* are known in other organisms. In some versions of the invention, the one or more modifications in the recombinant microorganisms can comprise a genetic modification that increases aromatic 4,5 dioxygenase activity. A genetic modification that increases aromatic 4,5 dioxygenase activity can comprise an introduction of a recombinant (genetically modified) aromatic 4,5 dioxygenase gene. The introduction of the recombinant aromatic 4,5 dioxygenase gene can occur by newly introducing a recombinant aromatic 4,5 dioxygenase gene to the microorganism or modifying an aromatic 4,5 dioxygenase gene already present in the microorganism. In some versions, the one or more modifications in the recombinant microorganisms can comprise a modification that increases activity of ligAB or a homolog thereof. A modification that increases activity of ligAB or a homolog thereof can comprise an introduction of recombinant ligAB genes or homologs thereof. The introduction of the recombinant ligAB genes or homologs thereof can occur by newly introducing recombinant ligAB genes or homologs thereof to the microorganism or modifying ligAB genes or homologs thereof already present in the microorganism.

p-Hydroxybenzoic acid 3-monooxygenase activity comprises the ability to hydroxylate p-hydroxybenzoic acid. An exemplary p-hydroxybenzoic acid 3-monooxygenase is Saro_2436 of *Novosphingobium aromaticivorans*, the nucleic acid coding sequence of which is SEQ ID NO:21 and the protein sequence of which is SEQ ID NO:22. Homologs of Saro_2436 of *Novosphingobium aromaticivorans* are known in other organisms. In some versions of the invention, the one or more modifications in the recombinant microorganisms can comprise a genetic modification that increases p-hydroxybenzoic acid 3-monooxygenase activity. A genetic modification that increases p-hydroxybenzoic acid 3-monooxygenase activity can comprise an introduction of a recombinant (genetically modified) p-hydroxybenzoic acid 3-monooxygenase gene. The introduction of the recombinant p-hydroxybenzoic acid 3-monooxygenase gene can occur by newly introducing a recombinant p-hydroxybenzoic acid 3-monooxygenase gene to the microorganism or modifying a p-hydroxybenzoic acid 3-monooxygenase gene already present in the microorganism. In some versions, the one or more modifications in the recombinant microorganisms can comprise a modification that increases activity of Saro_2436 or a homolog thereof. A modification that increases activity of Saro_2436 or a homolog thereof can comprise an introduction of a recombinant Saro_2436 gene or a homolog thereof. The introduction of the recombinant Saro_2436 gene or homolog thereof can occur by newly introducing a recombinant Saro_2436 gene or homolog thereof to the microorganism or modifying a Saro_2436 gene or homolog thereof already present in the microorganism.

CHMS dehydrogenase activity comprises the ability to oxidize CHMS to produce PDC. An exemplary CHMS dehydrogenase is ligC/LigC (Saro_2811) of *Novosphingobium aromaticivorans*, the nucleic acid coding sequence of which is SEQ ID NO:23 and the protein sequence of which is SEQ ID NO:24. Homologs of ligC/LigC of *Novosphingobium aromaticivorans* are known in other organisms. In some versions of the invention, the one or more modifications in the recombinant microorganisms can comprise a genetic modification that increases CHMS dehydrogenase activity. A genetic modification that increases CHMS dehydrogenase activity can comprise an introduction of a recombinant (genetically modified) CHMS dehydrogenase gene. The introduction of the recombinant CHMS dehydrogenase gene can occur by newly introducing a recombinant CHMS dehydrogenase gene to the microorganism or modifying a CHMS dehydrogenase gene already present in the microorganism. In some versions, the one or more modifications in the recombinant microorganisms can comprise a modification that increases activity of ligC or a homolog thereof. A modification that increases activity of ligC or a homolog thereof can comprise an introduction of a recombinant ligC gene or a homolog thereof. The introduction of the recombinant ligC gene or homolog thereof can occur by newly introducing a recombinant ligC gene or homolog thereof to the microorganism or modifying a ligC gene or homolog thereof already present in the microorganism.

The recombinant microorganisms in preferred versions of the invention are configured to exhibit enhanced production of PDC with respect to a corresponding microorganism. The recombinant microorganisms in such versions may include any one or more of the modifications described herein. Preferred modifications that confer enhancement of PDC production include modifications that reduce PDC hydrolase activity, CHMOD cis-trans isomerase activity, CHMOD methyl esterase activity, and/or vanillate/3-O-methylgallate O-demethylase activity. The additional modifications described herein can be implemented by themselves or in combination with the modifications that reduce PDC hydrolase activity, CHMOD cis-trans isomerase activity, CHMOD methyl esterase activity, and/or vanillate/3-O-methylgallate O-demethylase activity.

Modifications that reduce the activity of a gene or gene product includes any modification to a microorganism that ablates, reduces, inhibits, or otherwise disrupts production of a gene product, renders a produced gene product nonfunctional, or otherwise reduces or ablates a produced gene product's activity. Accordingly, in some instances, production of a gene product may be completely shut down. "Gene product" refers to products such as an mRNA or a polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

There are many well-known ways to reduce the activity of a gene or gene product. This can be accomplished, for example, by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that reduce the activity of a gene or gene product include but are not limited to substitutions, partial or complete deletions, insertions, or other variations to a coding sequence or a sequence controlling the transcription or translation of a coding sequence, such as placing a coding sequence under the control of a less active promoter, etc. In some versions, a gene or coding sequence can be replaced with a selection marker or screenable marker. In some versions, the genetic modifications can include the introduction of constructs that express ribozymes or antisense sequences that target the mRNA of the gene of interest. Various other genetic modifications that reduce the activity of a gene or gene product are described elsewhere herein. Various methods for introducing genetic modifications are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). In some instances, reducing the activity of a gene or gene product can be accomplished by chemically inhibiting the activity of a gene product with a small-molecule inhibitor, by expressing a protein that interferes with the activity of the gene product, or by other means.

"Increasing expression" or grammatical variants thereof may refer to expressing a gene product not made by the corresponding microorganism or expressing more of a gene product already made by the corresponding microorganism. Modifying the recombinant microorganisms to increase expression of the gene products described herein can be performed using any methods currently known in the art or discovered in the future. Examples include genetically modifying the microorganism and culturing the microorganism in the presence of factors that increase expression of the gene product. Suitable methods for genetic modification include but are not limited to placing the coding sequence under the control of a more active promoter, increasing the copy number of genes comprising the coding sequence, introducing a translational enhancer on a gene comprising the coding sequence (see, e.g., Olins et al. *Journal of Biological Chemistry*, 1989, 264(29):16973-16976), and/or modifying factors (e.g., transcription factors or genes therefor) that control expression of a gene comprising the coding sequence. Increasing the copy number of genes comprising a coding sequence can be performed by introducing one or more additional copies of the native gene to the microorganism, introducing one or more a heterologous homologs to the microorganism, introducing one or more copies of recombinant versions of the native gene or heterologous homolog to the microorganism, etc. Genes expressing a given coding sequence may be incorporated into the microbial genome or included on an extrachromosomal genetic construct such as a plasmid. "Exogenous" used in reference to a genetic element means the genetic element is a non-native genetic element. "Heterologous" used in reference to a genetic element means that the genetic element is derived from a different species. A genetic element, such as a promoter, that controls or affects the activity of another genetic element, such as a coding sequence, is herein described as being "operationally connected" thereto.

Some of the microorganisms of the invention may include at least one recombinant nucleic acid configured to express or overexpress a particular product. "Recombinant" as used herein with reference to a nucleic acid molecule or polypeptide is one that has a sequence that is not naturally occurring. The recombinant nucleic acid molecule or polypeptide can be made, for example, by chemical synthesis or by the artificial manipulation of isolated segments of nucleic acid molecules or polypeptides using genetic engineering techniques. A recombinant cell or microorganism is one that contains a recombinant nucleic acid molecule or polypeptide. "Overexpress" as used herein means that a particular gene product is produced at a higher level in one cell, such as a recombinant cell, than in a corresponding cell. For example, a microorganism that includes a recombinant nucleic acid configured to overexpress a gene product produces the gene product at a greater amount than a microorganism of the same species that does not include the recombinant nucleic acid.

In general, proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologous sequences of the sequences described herein include coding sequences, genes, or gene products (e.g., proteins), respectively, having at least about 30%, 35%, 40%, 45%, 50%, 55%, 60%, 65%, 70%, 75%, 80%, 85%, 90%, 95%, or 99% identity to the sequences described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs." Homologs also include sequences at least 90%, 95%, or 97% or more identical to the orthologs.

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is any nucleic acid or amino acid sequence described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Exogenous, heterologous nucleic acids encoding products to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

The recombinant microorganisms of the invention may comprise any type of microorganism. The microorganism may be prokaryotic or eukaryotic. Suitable prokaryotes include bacteria and archaea. Suitable types of bacteria include α- and γ-proteobacteria, gram-positive bacteria, gram-negative bacteria, ungrouped bacteria, phototrophs, lithotrophs, and organotrophs. Suitable eukaryotes include yeast and other fungi. The microorganism in some versions can be from an order selected from the group consisting of Sphingomonadales and Pseudomonadales. The microorganism in some versions can be from a family selected from the group consisting of Sphingomonadaceae and Pseudomonadaceae. The microorganism in some versions can be from a genus selected from the group consisting of *Sphingomonas, Sphingobium, Sphingosinicella, Sphingopyxis, Novosphingobium, Pseudomonas, Erythrobacter* (e.g., sp. SG61-1L), and *Altererythrobacter*. An exemplary microorganism from the genus *Novosphingobium* is *Novosphingobium aromaticivorans. Novosphingobium aromaticivorans* DSM12444 can naturally catabolize multiple aromatic compounds containing H, G, and S units via protocatechuic acid and 3-O-methylgallic acid as central metabolites, with PDC as a common intermediate.

The recombinant microorganisms of the invention preferably exhibit enhanced PDC production with respect to the corresponding microorganism when the recombinant microorganism and the corresponding organism are grown under identical conditions. The PDC production may be enhanced by a factor of at least about 1.1, at least about 1.5, at least about 2, at least about 2.5, at least about 3, at least about 3.5, at least about 4, at least about 4.5, at least about 5, at least about 5.5, at least about 6, or at least about 6.5 and/or up to about 6.5, up to about 7, or more. Such increases may reflect an increase by mass.

The recombinant microorganisms of the invention preferably exhibit enhanced PDC yield from certain substrates with respect to the corresponding microorganism when the recombinant microorganism and the corresponding organism are grown under identical conditions. The substrates may include one or more of vanillic acid, syringic acid, p-hydroxybenzoic acid, methyl guaiacol, propyl guaiacol, dihydroconiferyl alcohol, methyl syringol, p-hydroxy benzoic acid methyl ester, dihydrop-hydroxy cinnamic acid methyl ester, dihydrosyringol alcohol, and dihydroferulic acid methyl ester, among others. The PDC yield may be enhanced by a factor of at least about 1.1, at least about 1.5, at least about 2, at least about 2.5, at least about 3, at least about 3.5, at least about 4, at least about 4.5, at least about 5, at least about 5.5, at least about 6, or at least about 6.5 and/or up to about 6.5, up to about 7, or more. Such yields are determined on a mass basis.

The recombinant microorganisms of the invention preferably exhibit a yield from vanillic acid, syringic acid, or each of vanillic acid and syringic acid of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, or at least about 98%, or at least about 99%. Such yields are determined on a mass basis.

The PDC can be produced by culturing a recombinant microorganism of the invention in a medium comprising a plant-derived phenolic. The plant-derived phenolic can comprise any of a number of phenolics obtained from processing plant lignocellulosic biomass. Exemplary plant-derived phenolics comprise syringyl phenolics, guaiacyl phenolics, and p-hydroxyphenyl phenolics. Exemplary syringyl phenolics include syringaldehyde, syringic acid, and S-diketone. Exemplary guaiacyl phenolics include vanillin, vanillic acid, and G-diketone. Exemplary hydroxyphenyl phenolics include p-coumaric acid, p-hydroxybenzaldehyde, and p-hydroxybenzoic acid.

The plant-derived phenolic can be derived and/or provided in the form of depolymerized lignin, such as chemically depolymerized lignin. Methods of depolymerizing lignin are well known in the art. See Pandey et al. 2010 (Pandey M P, Kim C S. Lignin Depolymerization and Conversion: A Review of Thermochemical Methods. *Chemical & Engineering Technology*, 2010, Vol. 34, Issue 1, pp. 3-145) and Wang et al. 2013 (Wang H, Tucker M, Ji Y. Recent Development in Chemical Depolymerization of Lignin: A Review. *Journal of Applied Chemistry*, 2013, Volume 2013, Article ID 838645).

The depolymerized lignin can be derived from pretreated lignocellulosic biomass. Methods of pretreating lignocellulosic biomass are well known in the art. See Kumar et al. 2017 (Kumar A K and Sharma S. Recent Updates on Different Methods of Pretreatment of Lignocellulosic Feedstocks: A Review. *Bioresour. Bioprocess.* (2017) 4:7); Kumar et al. 2009 (Kumar, P.; Barrett, D. M.; Delwiche, M. J.; Stroeve, P., Methods for Pretreatment of lignocellulosic Biomass for Efficient Hydrolysis and Biofuel Production. Industrial & Engineering Chemistry Research 2009, 48, (8), 3713-3729); Wang et al. 2013 (Wang H, Tucker M, Ji Y. Recent Development in Chemical Depolymerization of Lignin: A Review. (2013) *Journal of Applied Chemistry.* 2013:1-9), and Karlen et al. 2020 (Karlen S D, Fasahati P, Mazaheri M, Serate J, Smith R A, Sirobhushanam S, Chen M, Tymkhin V I, Cass C L, Liu S, Padmakshan D, Xie D, Zhang Y, McGee M A, Russell J D, Coon J J, Kaeppler H F, de Leon N, Maravelias C T, Runge T M, Kaeppler S M, Sedbrook J C, Ralph J. Assessing the viability of recovering hydroxycinnamic acids from lignocellulosic biorefinery alkaline pretreatment waste streams. *ChemSusChem.* 2020 Jan. 26). Examples include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, organosolv, ionic liquids, gamma-valerolactone, and pulsed electrical field treatment, among others.

The lignocellulosic biomass can be derived from any source, such as corn cobs, corn stover, cotton seed hairs, grasses, hardwood stems, leaves, newspaper, nut shells, paper, softwood stems, sorghum, switchgrass, waste papers from chemical pulps, wheat straw, wood, woody residues, mixed biomass species such as those produced by native prairie, and other sources.

In addition to the plant-derived phenolic, the medium in some versions also comprises a fermentable sugar. Non-limiting examples of suitable fermentable sugars include adonitol, arabinose, arabitol, ascorbic acid, chitin, cellubiose, dulcitol, erythrulose, fructose, fucose, galactose, glucose, gluconate, inositol, lactose, lactulose, lyxose, maltitol, maltose, maltotriose, mannitol, mannose, melezitose, melibiose, palatinose, pentaerythritol, raffinose, rhamnose, ribose, sorbitol, sorbose, starch, sucrose, trehalose, xylitol, xylose, and hydrates thereof, among others.

In some versions, the fermentable sugar may be replaced by other organic compounds that support growth of the recombinant microorganism. This includes but is not limited to the other organic compounds that are present in the deconstructed biomass fractions from the crops or plant species mentioned above.

A recitation herein of a microorganism "comprising" a mutation in or to a particular gene refers to a gene that would be present were it not for the mutation, e.g., the gene present in a corresponding microorganism. Thus, the recitation of a microorganism "comprising" a mutation in or to a particular gene encompasses a mutated form of the gene present in the microorganism, a partially deleted remnant of the gene present in the microorganism, a complete absence of the gene (e.g., as resulting from a complete deletion of the gene) in the microorganism, or other configurations.

The methods can further comprise isolating the 2-pyrone-4,6-dicarboxylic acid from the recombinant microorganism and/or the medium. Methods of isolating 2-pyrone-4,6-dicarboxylic acid from a medium are provided in the attached examples and otherwise known in the art.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls. U.S. Pat. No. 10,144,938, US Pub. 2019/0048329, US Pub. 2016/0312257, and US Pub. 2020/0017891 are specifically incorporated herein by reference.

It is understood that the invention is not confined to the particular construction and arrangement of parts herein illustrated and described, but embraces such modified forms thereof as come within the scope of the claims.

EXAMPLES

Funneling Aromatic Products of Chemically Depolymerized Lignin into 2-Pyrone-4-6-Dicarboxylic Acid with *Novosphingobium aromaticivorans*

Summary

Lignin is an aromatic heteropolymer found in plant biomass. Depolymerization of lignin, either through biological or chemical means, invariably produces heterogenous mixtures of low molecular weight aromatic compounds. Microbes that can metabolize lignin-derived aromatics have evolved pathways that funnel these heterogeneous mixtures into a few common intermediates before opening the aromatic ring. In this work, we engineered a previously described recombinant form of *Novosphingobium aromaticivorans* DSM12444, via targeted gene deletions, to use its native funneling pathways to simultaneously convert plant-derived aromatic compounds containing syringyl (S), guaiacyl (G), and p-hydroxyphenyl (H) aromatic units into 2-pyrone-4,6-dicarboxylic acid (PDC), a potential polyester precursor. In batch cultures containing defined media, the engineered strain converted several of these depolymerization products, including S-diketone and G-diketone (non-natural compounds specifically produced by chemical depolymerization), into PDC with yields ranging from 22% to 100%. In batch cultures containing a heterogeneous mixture of aromatic monomers derived from chemical depolymerization of poplar lignin, 59% of the measured aromatic compounds were converted to PDC. Production of PDC from other lignin sources is also shown. Our results show that *N. aromaticivorans* is an exemplary microbial platform for funneling heterogeneous mixtures of lignin depolymerization products into PDC or other commodity chemicals.

Introduction

The impact of fossil carbon utilization on the global environment has encouraged the search for sustainable strategies to convert renewable resources into fuels and chemicals. Biorefining, the industrial activity of deriving fuels and chemicals from plant biomass in a sustainable and economically viable manner, is essential to reduce the proportion of fossil fuels that power the global economy. Plant biomass, the most abundant renewable organic resource on Earth, is primarily composed of sugars and phenolic compounds.[3,4] While there are already established approaches to derive fuels from the sugar components of plant biomass,[5] effective methods for biomass deconstruction to recover and valorize the phenolic components are only starting to emerge.[6,7] One source of phenolic compounds is lignin, an alkyl-aromatic heteropolymer that is interlinked with cellulose and hemicellulose in plant cell walls and accounts for up to 30% of the total lignocellulosic biomass weight.[8] There are other sources of phenolics in plant biomass, such as arabinofuranosides in grasses[9,10] or lignin bound p-hydroxybenzoate in some hardwoods.[11] The present examples show bio-based production of valuable chemicals from the phenolic components of plant biomass.

The most abundant biomass-derived phenolics can be classified based on the number of methoxy groups attached to the main phenyl structure; these are syringyl (S; two methoxy groups), guaiacyl (G; one methoxy group), and p-hydroxyphenyl (H; no methoxy groups) units.[12] Several approaches have been recently described for biomass deconstruction and lignin depolymerization that result in recovery of S, G, and H aromatic units.[6] However, the heterogeneity of the resulting mixtures presents a major challenge for conversion into commodity chemicals because of the low quantity of valuable marketable compounds in deconstructed lignin samples and the technical limitations for their separation or purification from other components.[7]

The present examples explore microbial strategies for the conversion of deconstructed lignin into commodity chemicals since microorganisms have evolved strategies to metabolize and gain energy from the degradation of a large variety of aromatics compounds.[13,14] Such strategies could be harnessed for the valorization of aromatic mixtures if the metabolic pathways are routed towards production of desirable chemical products.[15] In general, microbial transformation of aromatic compounds occurs by a combination of upper metabolic pathways, which convert multiple compounds into key aromatic intermediates[13] in what has been called "biological funneling",[16] and a central aromatic pathway that breaks the aromaticity and renders metabolic products that enter central carbon metabolism.[13,14] Biological funneling has been recently described for the conversion of plant-derived phenolics to aromatic compounds such as vanillin[17] and benzoic acid,[18] and to non-aromatic compounds, such as cis,cis-muconate,[19] β-keto adipate,[20] muconolactone,[20] 2-pyrone-4,6-dicarboxylic acid (PDC),[21,22] pyridine-2,4-dicarb oxylic acid,[23] and polyhydroxyalkanoates.[16] Some of these approaches require extensive metabolic re-routing and introduction of foreign pathways,[19,22] while others rely on a small number of mutations that redirect aromatic metabolism to the product of interest.[17,18]

Here we show the impact of gene deletions in the central aromatic catabolic pathways of *Novosphingobium aromaticivorans* DSM12444, an organism known or predicted to degrade a wide variety aromatic compounds[24] and to break down interlinkages in lignin,[25] that allow it to funnel a large diversity of plant-derived phenolics into PDC, a potential bioplastic and epoxy adhesives precursor.[26] A complete genome sequence is available for this α-proteobacterium (GenBank NC_007794.1), and the organism is amenable to genetic and genomic techniques needed to test the role of individual genes in aromatic metabolism, and model, engineer, or improve its pathways.[25] Specifically, we show that by using a defined set of mutations, *N. aromaticivorans* can be engineered to simultaneously produce PDC from all three major types of plant-derived phenolic compounds (S, G, and H). In addition, we find that this organism can metabolize aromatics simultaneously with the use of other organic carbon sources (such as glucose or those found in deconstructed plant biomass), a feature that allows mutant strains to excrete compounds derived from the incomplete metabolism of the aromatics. We predict that implementing the defined set of mutations described herein will result in the same or similar effects in other microorganisms. The present examples represent a valuable advance in using bacteria to funnel aromatic compounds into defined single commodities and shows that *N. aromaticivorans* an exemplary microbial chassis for valorization of lignin and other plant-derived aromatics.

Materials and Methods

Bacterial Strains, Growth Media and Culturing Conditions

A variant of *N. aromaticivorans* DSM12444 (strain 12444Δ1879) that lacks the gene Saro_1879 (coding sequence, SEQ ID NO:25, protein sequence, SEQ ID NO:26) (putative sacB; SARO_RS09410 in the recently reannotated genome in NCBI)[25] was used as a parent strain to create the deletion mutant strains 12444ΔligI (lacks gene Saro_2819; SARO_RS14300), 12444ΔdesCD (lacks the genes Saro_2864 and Saro_2865; SARO_RS14525 and SARO_RS14530), 12444ΔligIΔdesCD (lacks genes Saro_2819, Saro_2864, and Saro_2865), and others described herein. All genetic modifications used a variant of the plasmid pk18mobsacB,[37] which contains sacB and a kanamycin resistance gene. A detailed procedure for constructing strains with gene deletions is contained elsewhere herein. All bacterial strains and plasmids used in the present examples are listed in Table 1. Primers used in the construction of the mutant strains are listed in Table 2.

TABLE 1

Bacterial strains and plasmids used in the examples.

| Strains | Details | Reference |
|---|---|---|
| *Novosphingobium aromaticivorans* strains | | |
| 12444Δ1879 | DSM 12444 (WT) ΔSaro1879 | (25) |
| 12444ΔligI | 12444Δ1879 ΔSaro2819 | This study |
| 12444ΔdesC/D | 12444Δ1879 ΔSaro2864/5 | This study |
| 12444ΔligIΔdesC/D | 12444Δ1879 ΔSaro2819 ΔSaro2864/5 | This study |
| *Escherichia coli* strains | | |
| DH 5α | F-Φ80lacZΔM15 Δ(lacZYA-argF) U169 recA1 endA1 hsdR17 (rK-, mK+) phoA supE44λ-thi-1 gyrA96 relA1 | Bethesda Research Laboratories (44) |
| S17-1 | recA pro hsdR RP4-2-Tc::Mu-Km::Tn7 | (45) |
| Plasmids | | |
| pK18mobsacB | pMB1ori sacB kanR mobT oriT(RP4) lacZα | (37) |
| pK18msB/ ΔSaro2819 | pK18mobsacB containing genomic regions flanking Saro2819 | This study |
| pK18msB/ ΔSaro2864/5 | pK18mobsacB containing genomic regions flanking Saro2864/5 | This study |

TABLE 2

Primers used in the examples.

| Name | Sequence* | SEQ ID NO |
|---|---|---|
| Saro2819_Del-R | 5'-GCGCCAATCCATACCACGGATTATGCGAATACTACT CCATCCATCAGCTTG-3' | 27 |

TABLE 2-continued

Primers used in the examples.

| Name | Sequence* | SEQ ID NO |
|---|---|---|
| Saro2819-pK18_Amp-F | 5'-CGATTCATTAATGCAGCTGGCACGACAGGAGCGAATGGCATGAGTTCACATTCAGC-3' | 28 |
| Saro2819_Del-F | 5'-GCTGATGGATGGAGTAGTATTCGCATAATCCGTGGTATGGATTGGCGCATG-3' | 29 |
| Saro2819-pK18_Amp-R | 5'-GTTTCTGCGGACTGGCTTTCTAGATGTTCCTGCATGGTCTGGTCCTGTTCAAGCAG-3' | 30 |
| Saro2864-5Del R | 5'-GGGTAGTCTGGATCATTCAGACTCGCATGGTGCCGAG-3' | 31 |
| Saro2864-5-pK18_Amp_F | 5'-CGATTCATTAATGCAGCTGGCACGACAGCAGGTCGGCTTCAAGGAGGAAGTTCTG-3' | 32 |
| Saro2864-5_Del_F | 5'-CCATGCGAGTCTGAATGATCCAGACTACCCGCCGTTATC-3' | 33 |
| Saro2864-5-pK18_Amp_R | 5'-GTTTCTGCGGACTGGCTTTCTAGATGTTCGACCACTATGCAATGGAATGGAACCTGC-3' | 34 |
| Saro2865_Start-SNP_F | 5'-GGCATGCTCGGCACCATGCG-3' | 35 |
| Saro2865_Start-SNP_R2 | 5'-GCCGTCGACCGCGAGAGCTTG-3' | 36 |

*Regions in bold match sequence in pK18msB.

*Escherichia coli* cultures were grown in LB media containing 50 μg mL$^{-1}$ kanamycin at 37° C. *N. aromaticivorans* cultures were grown in SISnc-V0 media supplemented with the indicated carbon source at 30° C. SISnc-V0 media is a modification of Sistrom's minimal media[38] in which succinate, L-glutamate, L-aspartate, and vitamins were omitted. For routine culture and storage, the growth media was supplemented with 1 g L$^{-1}$ glucose. For gene modifications, the growth media was supplemented with 1 g L$^{-1}$ glucose and 50 μg mL$^{-1}$ kanamycin, or 1 g L$^{-1}$ glucose and 10% sucrose.

*N. aromaticivorans* Growth Experiments

Cell cultures were grown overnight in SISnc-V0 media supplemented with 1 g L$^{-1}$ glucose, then diluted 1:1 with fresh SISnc-V0 containing 1 g L$^{-1}$ glucose and incubated for one hour. Then, 2 ml of the growing culture was spun for 5 min at 5000 rpm, and the cell pellets were resuspended into fresh SISnc-V0 media containing no added carbon source. The resuspended cells were diluted 1:100 into SISnc-V0 media supplemented with the indicated carbon source, then shaken at 200 rpm and 30° C. Cell growth was monitored by measuring cell density using a Klett-Summerson photoelectric colorimeter with a red filter. For *N. aromaticivorans*, 1 Klett unit (KU) is equal to ~8×10$^6$ cfu ml$^{-1}$.[25] Culture samples (1 mL) were collected at various time points, spun for 5 min at 5000 rpm and 4° C., and the supernatants were filtered through 0.22 μM nylon syringe tip filters (Fisher Scientific), then stored at −20° C. Each culture was grown at least three times and the data shown corresponds to the results obtained from a representative culture. Conversion efficiency of aromatics to product was calculated by dividing the total amount of product by the total amount of aromatic substrates consumed. Conversion efficiencies reported correspond to the average and standard deviation of the efficiencies calculated for all replicates.

Production of PDC in a Fed-Batch Bioreactor

A 250 ml bioreactor (Infors, model Multifors 2) containing 130 ml minimum media with 12 mM glucose was inoculated with 2 ml of *N. aromaticivorans* strain 12444ΔligIΔdesCD culture that had been pre-grown overnight with glucose. After 7.5 h of batch incubation, the bioreactor was intermittently fed media containing 226 mM vanillic acid, 34 mM vanillin, 550 mM glucose, 15 g L$^{-1}$ ammonium sulfate, and 5% (v/v) DMSO. Culture pH was controlled by the addition of 1 M KOH when needed, to maintain pH 7. Temperature was maintained at 30° C. and the stirrer speed between 250 and 320 rpm. Air was used to deliver oxygen at a flow rate of 1 L min$^{-1}$. During 50 hours of operation, a total of 29 ml of feed solution was added.

Analysis of Extracellular Metabolites

Metabolite identification was performed by gas chromatography-mass spectrometry (GC-MS) of filtered culture supernatants. Sample aliquots (150 μL) were combined with 70 μL of 1 mM m-coumaric acid in water (internal standard), acidified with HCl to pH<2, and ethyl acetate extracted (3×500 μL). The three ethyl acetate extractions were combined, dried under a stream of N$_2$ at 40° C., and derivatized by the addition of 150 μL of pyridine and 150 μL of N,O-bis(trimethylsilyl)trifluoro-acetamide with trimethylchlorosilane (99:1, w/w, Sigma) and incubated at 70° C. for 45 min. The derivatized samples were analyzed on an Agilent GC-MS (GC model 7890A, MS Model 5975C) equipped with a (5% phenyl)-methylpolysiloxane capillary column (Agilent model HP-5MS). The injection port temperature was held at 280° C. and the oven temperature program was held at 80° C. for 1 min, then ramped at 10° C. min$^{-1}$ to 220° C., held for 2 min, ramped at 20° C. min$^{-1}$ to 310° C., and held for 6 min. The MS used an electron impact (EI) ion source (70 eV) and a single quadrupole mass selection scanning at 2.5 Hz, from 50 to 650 m/z. The data was analyzed with Agilent MassHunter software suite, using m-coumaric acid as internal standard.

Quantitative analysis of glucose and formic acid were performed on an Agilent 1260 infinity HPLC equipped with a refractive index detector (HPLC-RID) (Agilent Technologies, Inc., Palo Alto, Calif.) and an Aminex HPX-87H with Cation-H guard column (BioRad, Inc. Hercules, Calif.). The mobile phase was 0.02 N sulfuric acid at a flow rate of 0.5 ml min$^{-1}$.

Quantitative analysis of aromatic compounds and PDC were performed on a Shimadzu triple quadrupole liquid chromatography mass spectrometer (LC-MS) (Nexera XR HPLC-8045 MS/MS). The mobile phase was a binary gradient consisting of solvent A (water) and solvent B (0.1% formic acid in a 2:1 mixture of acetonitrile and methanol, v/v). The stationary phase was a Phemonenex Kinetex F5 column (2.6 µm pore size, 2.1 mm ID, 150 mm length, P/N: H18-105937). All compounds were detected by multiple-reaction-monitoring (MRM) and quantified using the strongest MRM transition (Table 3).

lower threshold of the column and confirmed that some of them interact with the stationary phase in the alkaline-water mobile phase, these were: rosmarinic acid (360 g mol$^{-1}$, 21.49 min), ferulic acid (194 g mol$^{-1}$, 26.63 min), p-coumaric acid (164 g mol$^{-1}$, 24.96 min), vanillic acid (168 g mol$^{-1}$, 24.22 min), p-hydroxybenzoic acid (138 g mol$^{-1}$, 24.87 min), and guaiacol (124 g mol$^{-1}$, 39.82 min). Compounds eluting from 17.0-22.7 min correspond to oligomeric lignin, while compounds eluting after 22.7 min, correspond to dimeric and monomeric compounds. It should be noted that no $M_w$ values were calculated for peaks detected after 22.7 min, as they were outside the calibration range of the GPC column. In the control samples there were strong monomer signals eluting after 26.0 min, especially a pair of signals at ~30 min with an absorption band at 375 nm. Most of these monomer signals were not present, or were much weaker, in the inoculated samples after 78 hours of incubation.

TABLE 3

Multiple reaction module (MRM) conditions for HPLC-MS quantification of compounds used in the present examples.

| Compound | MW (g/mol) | Parent (—) m/z | Transition 1 | Transition 2 | Transition 3 |
|---|---|---|---|---|---|
| PDC | 184.103 | 183 | 183 -> 139.05 CE11 | 183 -> 111 CE14 | 183 -> 94.95 CE12 |
| Protocatechuic acid | 154.12 | 153 | 153 -> 108.95 CE14 | 153 -> 107.95 CE25 | 153 -> 90.95 CE27 |
| p-hydroxybenzoic acid | 138.12 | 137 | 137 -> 93 CE15 | 137 -> 65 CE30 | |
| Vanillic acid | 168.15 | 167 | 167 -> 123.05 CE15 | 167 -> 108 CE21 | 167 -> 152.05 CE18 |
| p-hydroxybenzaldehyde | 122.12 | 121.2 | 121.2 -> 92.05 CE26 | 121.2 -> 93,10 CE22 | 121.2 -> 41 CE49 |
| Syringic acid | 198.17 | 197 | 197 -> 121.05 CE18 | 197 -> 153.10 CE15 | 197 -> 182.10 CE15 |
| Vanillin | 152.15 | 151 | 151 -> 136 CE17 | 151 -> 92 CE22 | 151 -> 108 CE24 |
| p-Coumaric acid | 164.16 | 163 | 163 -> 119.05 CE15 | 163 -> 93 CE31 | 163 -> 116.95 CE33 |
| Syringaldehyde | 182.18 | 181 | 181 -> 166.10 CE16 | 181 -> 151 CE22 | 181 -> 123 CE28 |
| Ferulic acid | 194.19 | 193 | 193 -> 149 CE13 | 193 -> 134 CE16 | 193 -> 133 CE27 |
| G-diketone | 194.19 | 193 | 193 -> 178.10 CE20 | 193 -> 136 CE21 | 193 -> 107 CE31 |
| S-diketone | 224.21 | 223 | 223 -> 208.10 CE19 | 223 -> 193.10 CE20 | 223 -> 165.10 CE27 |

$^1$H-NMR Analysis

Nuclear magnetic resonance (NMR) spectroscopy was performed on a Bruker Biospin (Billerica, Mass.) Avance 500 MHz spectrometer equipped with a 5 mm quadruple-resonance $^1$H/$^{31}$P/$^{13}$C/$^{15}$N QCI gradient cryoprobe with inverse geometry (proton coils closest to the sample). Samples were prepared as ~1 mg in 600 µL acetone-$d_6$.

Gel Permeation Chromatography (GPC) Analysis

Analytical GPC was performed on a Shimadzu LC20 with a photodiode array detector (SPD-M20A). Separation was performed using a PSS PolarSil linear S column (7.8 mm×30 cm, 5 µm) at 35° C. The mobile phase was 5.2 mM sodium phosphate buffer at pH 8, pumped at 0.5 mL min$^{-1}$, 60 min run time. The molecular weight distribution was calibrated at λ=254 nm using PDC (184 g mol$^{-1}$, 23.55 min) and poly(styrene sulfonate) sodium salts, Mp (retention time): 976 kDa (13.20 min), 258 kDa (13.55 min), 65.4 kDa (14.78 min), 47 kDa (16.07 min), 9.74 kDa (17.96 min), 4.21 kDa (19.433 min), and 2.18 kDa (20.35 min) from the PSS-psskit (Polymer Standards Service-USA, Inc, Amherst, Mass., USA). Monomer standards were also ran to establish the Preparation of Media Containing Depolymerized Lignin Products Lignin was isolated by acid precipitation from pretreatment liquor of poplar biomass that had been pretreated by the copper alkaline hydrogen peroxide method (AHP-Cu).[39-41] The lignin was depolymerized using an adaptation of the oxidative methods described previously.[4] Depolymerization products were recovered by ethyl acetate extraction, followed by solvent evaporation. This material was re-dissolved in water while adjusting the pH to 7.0 to favor solubilization of aromatic compounds. Consistent with reported products of oxidative depolymerization,[4] quantitative HPLC-MS analysis showed concentrations of 1 mM G-diketone, 0.35 mM S-diketone, 0.37 mM syringic acid, 0.12 mM syringaldehyde, 0.44 mM vanillic acid, 0.1 mM vanillin, and 0.93 mM p-hydroxybenzoic acid in the final aqueous solution. For experiments with N. aromaticivorans, aliquots of this solution (25 mL) were mixed with concentrated (5x) SISnc-V0 media containing 1 g L$^{-1}$ glucose (20 mL) and water (55 mL).

Chemicals

Syringic acid, syringaldehyde, ferulic acid, vanillic acid, vanillin, p-coumaric acid, p-hydroxybenzoic acid, p-hydroxybenzaldehyde, and protocatechuate were purchased from Sigma-Aldrich (St Louis, Mo.). G- and S-diketones were synthesized according to the methods described elsewhere herein. PDC was produced by culturing N. aromaticivorans 12444ΔligI in 1 L of SISnc-V0 media supplemented with 3 mM vanillic acid and 0.5 g $L^{-1}$ (2.8 mM) glucose, and purified following a simplified version of published methods,[42] obtaining a >97% pure chemical standard for GC-MS and LC-MS quantifications. Specific details of these procedures are detailed elsewhere herein. The identity of PDC was confirmed by comparing the GC-MS spectrum of TMS derivatives and the $^1$H-NMR spectrum with those reported previously.[43]

Construction of Deletion Mutants of N. aromaticivorans

Construction of plasmids for deleting genes Saro_2819 or Saro_2864/5. Regions of N. aromaticivorans genomic DNA containing ~1100 bp upstream and downstream of Saro_2819 or Saro_2864/5 were PCR amplified separately using the pairs of primers Saro2819_Del-R/Saro2819-pK18_Amp-F and Saro2819_Del-F/Saro2819-pK18_Amp-R for Saro_2819, and Saro2864-5_Del_R/Saro2864-5-pK18_Amp_F and Saro2864-5_Del_F/Saro2864-5 pK18_Amp_R for Saro_2864/5 (Table S2). The pairs of DNA amplified flanking regions for each gene were combined with linearized pK18msB using NEBuilder® HiFi DNA Assembly Master Mix (New England Biolabs, Ipswich, Mass.) to produce the plasmids pK18msB/ΔSaro2819 and pK18msB/ΔSaro2864/5, respectively. A 32 bp region of Saro_2865 (including the start codon) is predicted to overlap with Saro_2866. To prevent transcription of this region of Saro_2865, this putative start codon of Saro_2865 was mutated by replacing a T by a C at position 3088561 in the genome (in addition to deleting the sequence of Saro_2865 downstream of the Saro_2866 stop codon). To mutate the Saro_2865 start site, PCR was performed on plasmid pK18msB/ΔSaro2864/5 using the primers Saro2865_Start-SNP_F and Saro2865_Start-SNP_R2, which were previously phosphorylated with polynucleotide kinase from Promega (Madison, Wis.). The amplified product was circularized with T4 DNA ligase from New England Biolabs to obtain the circular plasmid pK18msB/ΔSaro2864/5. The plasmids were then transformed into NEB 5-alpha competent E. coli (New England Biolabs). The transformed E. coli cells were then cultured in LB media+ kanamycin and the plasmids purified using a Qiagen® Plasmid Maxi Kit (Qiagen, Germany).

Deletion of genes Saro_2819 and Saro_2864/5. The purified plasmids were then transformed into competent E. coli S17-1 and subsequently mobilized into N. aromaticivorans strain 12444Δ1879 or 12444ΔligI cells via conjugation. Transconjugant cells of N. aromaticivorans (single cross overs) were isolated on SISnc-V0 plates containing 1 g/L glucose and 50 ug/mL kanamycin. To select for cells that eliminated the plasmid via a second instance of homologous recombination (double crossovers), single crossover cells were cultured on SISnc-V0 media containing 1 g/L glucose and 10% sucrose. Double crossover cells were isolated on SISnc-V0 plates containing 1 g/L glucose and 10% sucrose. PCR amplified regions of the target genes were sequenced to verify the deletions.

Purification of PDC

PDC was biologically produced by culturing Novosphingobium aromaticivorans strain 12444ΔligI in SISnc-V0 media supplemented with 3 mM vanillic acid and 3 mM glucose. Cells were grown to stationary phase and the culture media spun at 5000 RPM for 10 minutes and then filtered using a 500 ml Rapid-Flow bottle top filter with 0.2 µM SFCA membrane (Thermo Scientific). The filtrate (~900 mL) was transferred to a large 2 L separatory funnel and prepared for extraction of the acidic PDC by dilution with 50 mL brine (saturated sodium chloride) and 20 mL concentrated hydrogen chloride. The acidified PDC was extracted with ethyl acetate (4×100 mL). The combined ethyl acetate fraction (~400 mL) was extracted with 0.1 M sodium hydroxide (4×50 mL). The combined sodium hydroxide fraction was acidified with 2 M hydrogen chloride (20 mL) and brine (50 mL), then extracted with ethyl acetate (3×100 mL). The combined ethyl acetate fraction was dried using anhydrous sodium sulfate, filtered through a qualitative cellulose filter (VWR 28320-100), and the solvent removed on a rotatory evaporator giving 297 mg of PDC as a light orange solid. A TMS derivatized sample of the isolated PDC was characterized by GC-MS (method described in materials and methods section), which showed that PDC was the only peak, indicating a fairly high purity. The identity and purity of the PDC was confirmed by comparison of the $^1$H NMR data to previously published values. The NMR and GC-MS spectra indicated the purity of PDC to be approximate 97%.

Steps in the Synthesis of S Diketone

Synthesis of 4-acetyl Syringaldehyde

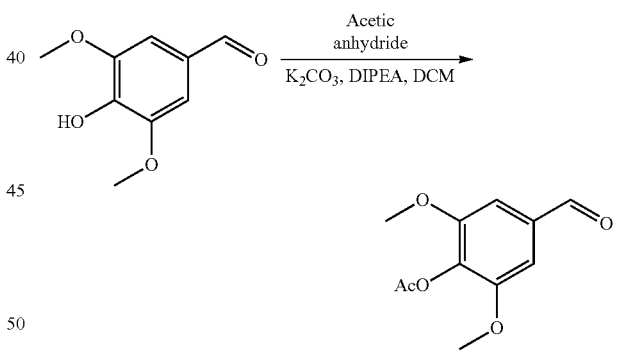

To a 100 mL round bottom flask with stir bar were added syringaldehyde (3.296 g, 18.09 mmol), acetic anhydride (3.2 mL, 33.85 mmol), diisopropyl ethyl amine (1 mL, 5.74 mmol), potassium carbonate (793 mg, 5.74 mmol), and dichloromethane (50 mL). The solution was allowed to stir at room temperature. After 24 hours, the reaction was added to a separatory funnel, washed with saturated sodium bicarbonate (3×100 mL), and concentrated in vacuo to yield 4-acetyl syringaldehyde as an off-white solid (3.812 g, 17.00 mmol, 94% yield). $^1$H NMR (400 MHz, Chloroform-d) δ 9.91 (s, 1H), 7.16 (s, 2H), 3.91 (s, 6H), 2.37 (s, 3H). See Figure S6 of Perez et al.[46] for the $^1$H NMR spectra of synthesized 4-acetyl syringaldehyde.

Synthesis of 1-(4-acetoxy-3,4-dimethoxyphenyl)-1-propene

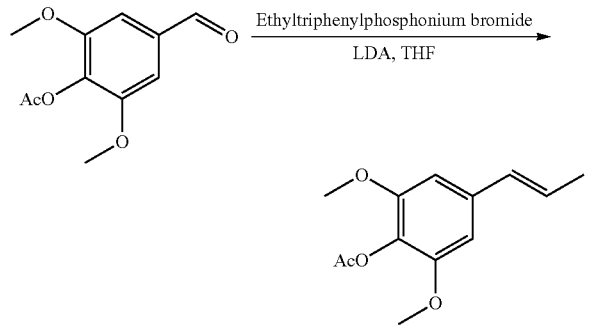

An oven dried, 100 mL round bottom flask with stir bar was charged with ethyltriphenylphosphonium bromide (7.0 g, 18.85 mmol), outfitted with a rubber septum, and the atmosphere within it purged with nitrogen. Freshly distilled THF (50 mL) was added via syringe and cooled to −78° C. While stirring, a solution of 2.0 M lithium diisopropyl amide (9.5 mL, 19 mmol) was added to generate ethenyltriphenylphosphonium bromide. While this solution stirred for 30 minutes, an oven dried, 250 mL round bottom flask with stir bar was charged with 4-acetyl-syringaldehyde (3.812 g, 17.0 mmol), sealed with a rubber septum, and purged with nitrogen. Freshly distilled THF (50 mL) was added via syringe and cooled to −78° C. Once the aldehyde was fully dissolved, the ethenyltriphenylphosphonium bromide solution was transferred by cannula and positive pressure to the 4-acetyl-syringaldehyde solution in a dropwise manner over the course of 45 minutes. Upon completion, the reaction was allowed to stir at −78° C. for an hour. The reaction was then brought to room temperature and stirred for two hours. The solution was quenched with saturated aqueous ammonium chloride and concentrated under reduced pressure. The remaining solution was diluted with water and extracted with ethyl acetate (3×100 mL). The organic layer was then evaporated leaving behind a pale yellow solid. The crude was purified by flash silica chromatography (5:1 hexanes/ethyl acetate). Fractions corresponding to the desired product were combined and evaporated, leaving behind 1-(4-acetoxy-3,4-dimethoxyphenyl)-1-propene as a white powder (1.2 g, 5.36 mmol, 32% yield, 1.08:1 cis/trans). $^1$H NMR (400 MHz, Chloroform-d) δ 6.54 (s, 2H), 6.35 (dq, J=11.6, 1.9, 1H), 5.79 (dq, J=11.6, 7.2 Hz, 1H), 3.82 (s, 6H), 2.34 (s, 3H), 1.92 (dd, J=7.2, 1.9 Hz, 3H). See Figure S7 of Perez et al.[46] for the $^1$H NMR spectra of synthesized 1-(4-acetoxy-3,4-dimethoxyphenyl)-1-propene.

Synthesis of 1-(4-acetoxy-3,4-dimethoxyphenyl)-1,2-propane dione

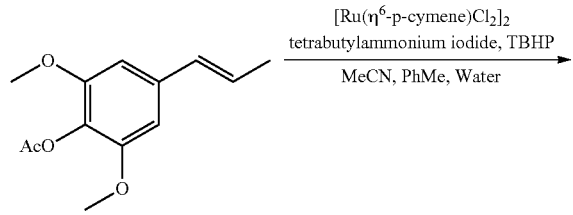

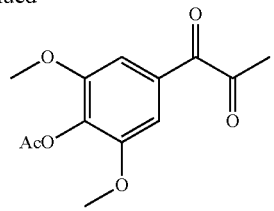

To a 100 mL round bottom flask with stir bar were added 1-(4-acetoxy-3,4-dimethoxyphenyl)-1 propene (720 mg, 3.05 mmol), dichloro(p-cymene)Ru(II) dimer (69.2 mg, 0.042 mmol), tetrabutylammonium iodide (336.4 mg, 0.91 mmol), tert-butyl hydroperoxide (70% solution in water, 3.6 mL), toluene (20 mL), acetonitrile (20 mL), and water (2.2 mL). The solution was allowed to stir at room temperature for 30 minutes then quenched with an excess of saturated aqueous sodium thiosulfate. The organic layer was isolated, concentrated in vacuo to a thick residue, and then purified by flash silica chromatography (4:1 hexanes/ethyl acetate). The resulting bright yellow fractions corresponding to the product were combined and evaporated to yield 1-(4-acetoxy-3,4-dimethoxyphenyl)-1,2-propane dione as a bright yellow solid (445 mg, 1.67 mmol, 55% yield). $^1$H NMR (400 MHz, Chloroform-d) δ 7.33 (s, 2H), 3.88 (s, 6H), 2.53 (s, 3H), 2.36 (s, 3H). See Figure S8 of Perez et al.[46] for the $^1$H NMR spectra of synthesized 1-(4-acetoxy-3,4-dimethoxyphenyl)-1,2-propane dione.

Synthesis of 1-(4-hydroxy-3,4-dimethoxyphenyl)-1,2-propane dione (S-diketone)

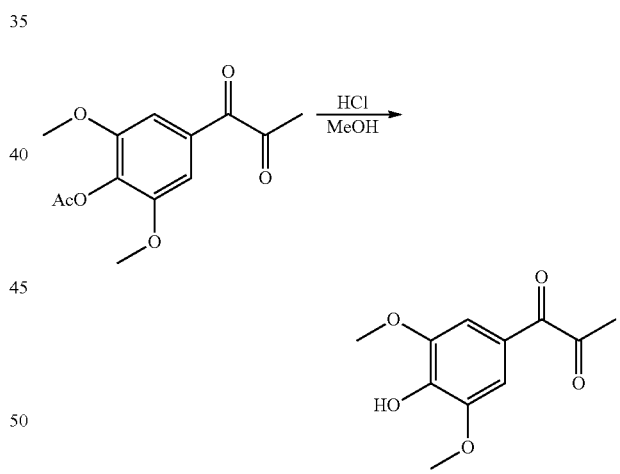

To a 250 mL round bottom flask were added 1-(4-acetoxy-3,4-dimethoxyphenyl)-1,2-propane dione (445 mg, 1.67 mmol), 3 M HCl (35 mL), and methanol (75 mL). The solution stirred at room temperature and reaction progress was monitored by TLC. Upon completion, the reaction was concentrated, diluted with saturated sodium bicarbonate, and washed with ethyl acetate. The aqueous layer was acidified with dilute ammonium chloride and extracted with ethyl acetate (3×50 mL). The resulting organic layer was concentrated and purified by flash silica chromatography (4:1 hexanes/ethyl acetate). The desired fractions were combined and evaporated to yield 1-(4-hydroxy-3,4-dimethoxyphenyl)-1,2-propane dione (S-diketone) as a bright yellow solid (259 mg, 1.16 mmol, 69% yield). $^1$H NMR (400 MHz, Chloroform-d) δ 7.34 (s, 2H), 6.11 (s, 1H), 3.95 (s, 3H), 2.53 (s, 3H). See Figure S9 of Perez et al.[46] for the ¹H NMR spectra of synthesized 1-(4-hydroxy-3,4-dimethoxyphenyl)-1,2-propane dione (S-diketone).

Steps in the Synthesis of G Diketone

Synthesis of Isoeugenyl Acetate

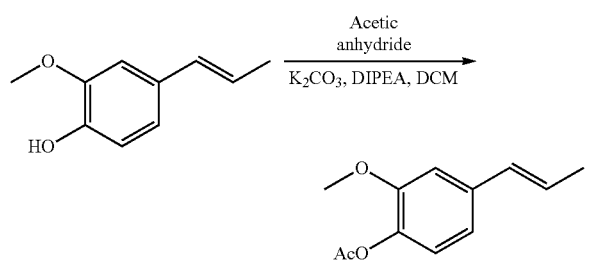

To a 100 mL round bottom flask with stir bar were added isoeugenol (2.6 mL, 17.10 mmol), acetic anhydride (3.00 mL, 31.73 mmol), diisopropyl ethyl amine (1 mL, 5.74 mmol), potassium carbonate (793 mg, 5.74 mmol), and dichloromethane (500 mL). The solution was allowed to stir at room temperature. After 24 hours, the reaction was added to a separatory funnel, washed with saturated sodium bicarbonate (3×100 mL), and concentrated in vacuo. The resulting off white powder was recrystallized from hot acetone to yield isoeugenyl acetate as white crystals (2.292 g, 11.11 mmol, 65% yield). ¹H NMR (400 MHz, Chloroform-d) δ 6.95 (d, J=8.1 Hz, 1H), 6.92 (d, J=1.8 Hz, 1H), 6.89 (dd, J=8.1, 1.9 Hz, 1H), 6.36 (dq, J=15.6, 1.7 Hz, 1H), 6.18 (dq, J=15.7, 6.6 Hz, 1H), 3.84 (s, 3H), 2.30 (s, 3H), 1.88 (dd, J=6.6, 1.6 Hz, 3H). See Figure S10 of Perez et al.[46] for the ¹H NMR spectra of synthesized isoeugenyl acetate.

Synthesis of 1-(4-acetoxy-3-methoxyphenyl)-1,2-propane dione

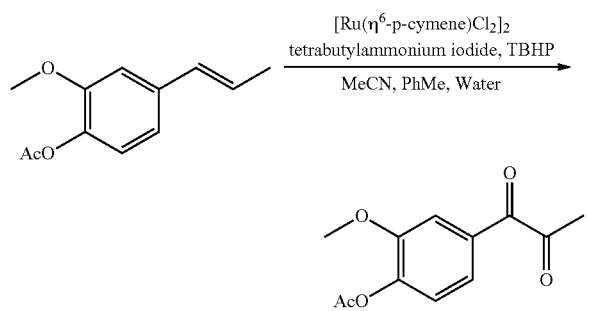

To a 250 mL round bottom flask with stir bar were added isoeugenyl acetate (2.060 g, 9.99 mmol), dichloro(p-cymene)Ru(II) dimer (69.2 mg, 0.11 mmol), tetrabutylammonium iodide (1.12 g, 3.03 mmol), tert-butyl hydroperoxide (70% solution in water, 10 mL), toluene (30 mL), acetonitrile (30 mL), and water (7 mL). The solution was allowed to stir at room temperature for 45 minutes then quenched with an excess of saturated aqueous sodium thiosulfate. The organic layer was isolated, concentrated in vacuo to a thick residue, and then purified by flash silica chromatography (4:1 hexanes/ethyl acetate). The resulting bright yellow fractions corresponding to the product were combined and evaporated to yield 1-(4-acetoxy-3-methoxyphenyl)-1,2-propane dione as a bright yellow solid (1.28 g, 5.42 mmol, 54% yield). ¹H NMR (400 MHz, Chloroform-d) δ 7.66 (d, J=1.9 Hz, 1H), 7.64 (dd, J=8.1, 1.9 Hz, 1H), 7.16 (d, J=8.2 Hz, 1H), 3.90 (s, 3H), 2.52 (s, 3H), 2.34 (s, 3H). See Figure S11 of Perez et al.[46] for the ¹H NMR spectra of synthesized 1-(4-acetoxy-3-methoxyphenyl)-1,2-propane dione.

Synthesis of 1-(4-hydroxy-3-methoxyphenyl)-1,2-propane dione (G-diketone)

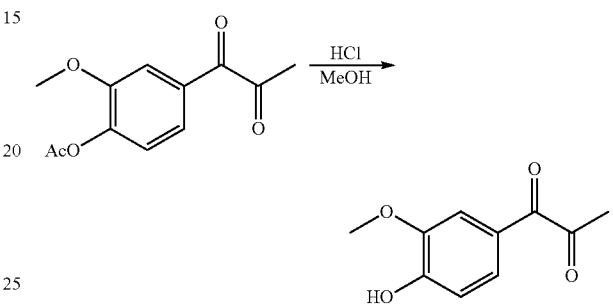

To a 500 mL round bottom flask were added 1-(4-acetoxy-3-methoxyphenyl)-1,2-propane dione (1.00 g, 4.23 mmol), 3 M HCl (90 mL), and methanol (190 mL). The solution was stirred at room temperature and reaction progress was monitored by TLC. Upon completion, the reaction was concentrated, diluted with saturated sodium bicarbonate, and washed with ethyl acetate. The aqueous layer was acidified with dilute ammonium chloride and extracted with ethyl acetate (3×100 mL). The resulting organic layer was concentrated and purified by flash silica chromatography (4:1 hexanes/ethyl acetate). The desired fractions were combined and evaporated to yield 1-(4-hydroxy-3-methoxyphenyl)-1,2-propane dione as a bright yellow, viscous oil (526 mg, 2.71 mmol, 64% yield). ¹H NMR (400 MHz, Chloroform-d) δ 7.61 (dd, J=8.3, 1.9 Hz, 1H), 7.58 (d, J=1.9 Hz, 1H), 6.98 (d, J=8.3 Hz, 1H), 6.21 (s, 1H), 3.97 (s, 3H), 2.51 (s, 3H). See Figure S12 of Perez et al.[46] for the ¹H NMR spectra of synthesized 1-(4-hydroxy-3-methoxyphenyl)-1,2-propane dione (G-diketone).

Results

Model of Aromatic Metabolism By *N. aromaticivorans* DSM12444 and Justification of Experimental Approach

*N. aromaticivorans* DSM12444, a bacterium isolated from a polyaromatic hydrocarbon-contaminated sediment in the deep subsurface, aerobically utilizes a variety of aromatic compounds as sole carbon and energy sources for growth.[24] Based on its genome content, a recent analysis of *N. aromaticivorans* aromatic metabolism using a transposon library,[2] and the known metabolism of lignin-derived aromatics in the related α-proteobacterium *Sphingobium* sp. SYK-6,[1] we propose a model for the degradation pathways of plant-derived aromatic compounds in this organism (FIG. 1). Consistent with the predicted pathways in *N. aromaticivorans* and *Sphingobium* sp. SYK-6, we propose that G and H aromatic units are degraded via protocatechuic acid (FIG. 1), with ring opening by LigAB, a 4,5 extradiol dioxygenase that yields 4-carboxy-2-hydroxy-cis,cis-muconate-6-semialdehyde (CHMS). CHMS is then oxidized to PDC by the dehydrogenase LigC. LigI is predicted to hydrolyze PDC to produce 4-oxalomesaconate (OMA),[27]

which is further transformed to the central carbon metabolites pyruvate and oxaloacetate (FIG. 1).

Dimethoxylated aromatics (S aromatics) are predicted to be degraded via a separate pathway, with demethylation of syringic acid to 3-methylgallate (3-MGA) carried out by the O-demethylase DesA (FIG. 1). In *N. aromaticivorans*, LigAB has been proposed to catalyze ring opening to produce a mixture of stereoisomers of 4-carboxy-2-hydroxy-6-methoxy-6-oxohexa-2,4-dienoate (CHMOD); a cis-trans isomerase, DesD, isomerizes one of the stereoisomers, and the methylesterase DesC completes demethylation of CHMOD to OMA.[2] Two other routes of 3-MGA degradation are proposed in *Sphingobium* sp. SYK-6, one requiring ring opening by the 3,4-dioxygenase DesZ and cyclization to PDC and another one requiring O-demethylation to gallate by LigM followed by ring opening by the dioxygenase DesB.[1] While LigM is present in *N. aromaticivorans*, homologues of DesZ and DesB are not encoded in its genome.[2] In addition, the LigAB of *Sphingobium* sp. SYK-6 has been shown to produce a combination of CHMOD and PDC when 3-MGA is the substrate,[28] and there are reports of slow abiotic transformation of CHMOD to PDC.[29] Therefore, in our model (FIG. 1), we hypothesize that the main enzymatic route of 3-MGA degradation in *N. aromaticivorans* is via CHMOD to OMA, but that PDC may also be a product of enzymatic or abiotic CHMOD transformation.

We used the above model to hypothesize which disruptions in the aromatic degradation pathways in *N. aromaticivorans* would lead to accumulation of specific pathway intermediates. We chose to focus on creating mutations that could lead to accumulation of PDC (FIG. 1), which is of particular interest since this dicarboxylic acid has been shown to be a suitable precursor for polyesters.[30] We hypothesized that a disruption of the proposed G and H degradation pathway via the deletion of the ligI gene (FIG. 1) would prevent PDC degradation and lead to its accumulation in cultures fed G and H aromatics as substrates.

Furthermore, we predicted that this metabolic disruption would result in strains with limited ability to grow on G and H aromatics, since most of the carbon in these compounds would remain in the PDC molecule. If this latter prediction is correct, then the addition of another substrate would be needed to support growth of cells on G or H aromatics lacking a functional ligI gene. In addition, given the possibility of PDC production from CHMOD (FIG. 1), we also hypothesized that deleting the desCD genes would result in accumulation of upstream intermediates and redirection of metabolism via PDC (FIG. 1).

Below we describe how we tested these hypotheses and how the defined mutations lead to PDC accumulation from (i) G and H units, (ii) S, G, and H units, and (iii) aromatics that are present in depolymerized lignin.

Figure 2:
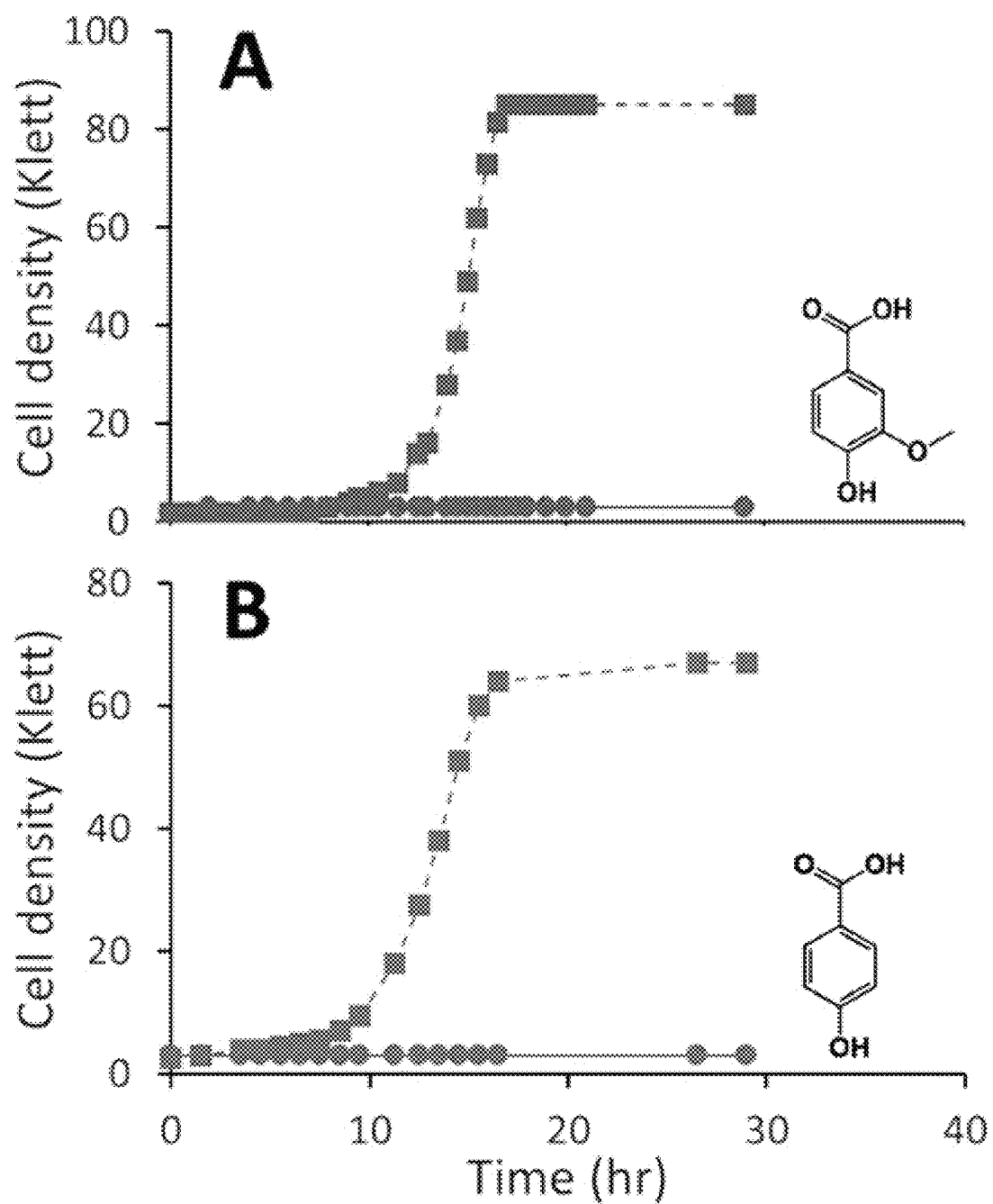
FIG. 2. Cell density of representative *N. aromaticivorans* cultures grown on 3 mM vanillic acid (panel A) or 3 mM p-hydroxybenzoic acid (panel B). Parent strain 12444Δ1879 represented by squares and dashed line; strain 12444ΔligI represented by circles.
Figure 3:
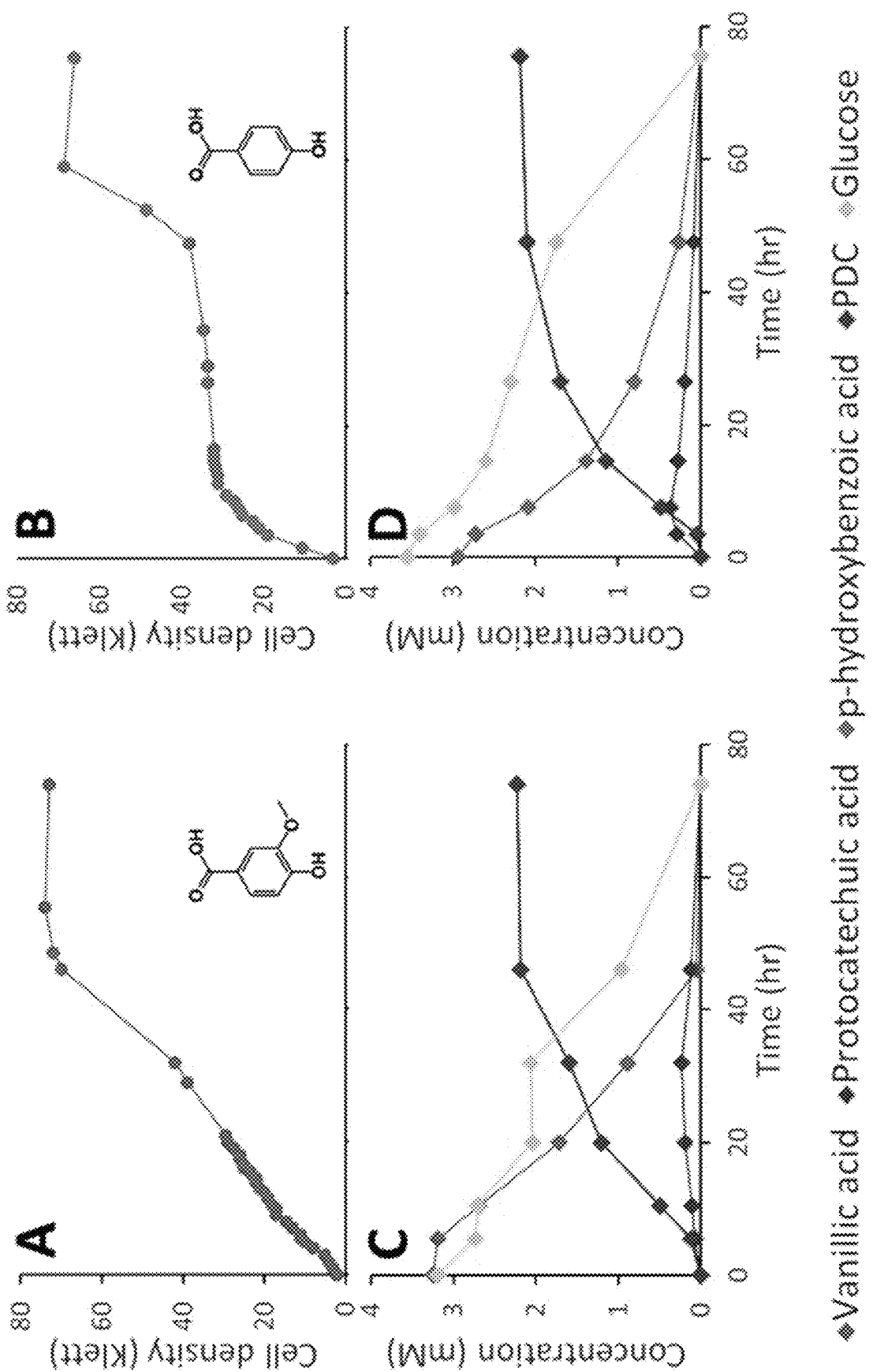
FIG. 3. Cell density and extracellular metabolite concentration of representative *N. aromaticivorans* strain 12444ΔligI cultures grown on a combination of 3 mM vanillic acid and 3 mM glucose (panels A and C) or a combination of 3 mM p-hydroxybenzoic acid and 3 mM glucose (panels B and D).

Construction of a *N. aromaticivorans* Mutant that Accumulates PDC from G and H Aromatics We constructed strain 12444ΔligI by deleting the ligI gene and cultured it initially in minimal media containing glucose since this gene was not predicted to be necessary for glucose metabolism. To test the role of this gene in metabolism of aromatic compounds, we attempted to grow strain 12444ΔligI on minimal media containing 3 mM vanillic acid or 3 mM p-hydroxybenzoic acid as representative of G and H aromatics, respectively. As expected, strain 12444ΔligI was unable to grow on either of these substrates as sole carbon sources (FIG. 2). When glucose was provided in addition to vanillic acid or p-hydroxybenzoic acid, strain 12444ΔligI was able to grow (FIG. 3 panels A and B), and, in both cases, glucose and the aromatic substrate were removed from the media, a small amount of protocatechuic acid transiently accumulated, and PDC accumulated as the final product of the transformations (FIG. 3 panels C and D). The PDC yield from vanillic acid and p-hydroxybenzoic acid by strain 12444ΔligI in these cultures were 81% (±17%) and 73% (±1.7%), respectively (Table 4).

TABLE 4

PDC yield from different aromatic compounds by N. aromaticivorans strains 12444ΔligI (p-coumaric acid, p-hydroxybenzaldehyde, p-hydroxybenzoic acid, ferulic acid, vanillin, and vanillic acid) and 12444ΔligIΔdesCD (G-diketone, syringaldehyde, syringic acid, and S-diketone) into PDC. Numbers in parenthesis represent one standard deviation of the average from 3 replicate cultures.

| Compound | | | Yield (%) |
|---|---|---|---|
| 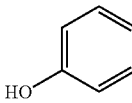 | p-Coumaric acid | 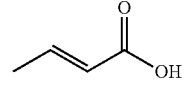 | 84 (±5.4) |
| | p-Hydroxybenzaldehyde | 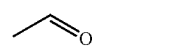 | 79 (±2.0) |
| | p-Hydroxybenzoic acid | 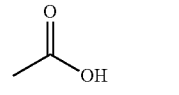 | 73 (±1.7) |
| 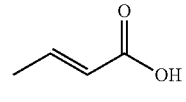 | Ferulic acid | 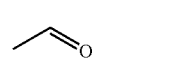 | 76 (±10.0) |
| | Vanillin | | 100 (±0.1) |

TABLE 4-continued

PDC yield from different aromatic compounds by N. aromaticivorans strains 12444ΔligI (p-coumaric acid, p-hydroxybenzaldehyde, p-hydroxybenzoic acid, ferulic acid, vanillin, and vanillic acid) and 12444ΔligIΔdesCD (G-diketone, syringaldehyde, syringic acid, and S-diketone) into PDC. Numbers in parenthesis represent one standard deviation of the average from 3 replicate cultures.

The compounds below share a common aromatic core structure (3,5-dimethoxy-4-hydroxyphenyl with R substituent):

| Compound | R | Yield (%) |
|---|---|---|
| Vanillic acid | –C(=O)OH | 81 (±17.0) |
| G-diketone | –C(=O)C(=O)CH₃ (methylglyoxal-type) | 107 (±1.6) |
| Syringaldehyde | –CH=O | 90 (±7.2) |
| Syringic acid | –C(=O)OH | 66 (±13.2) |
| S-diketone | –C(=O)C(=O)CH₃ | 22 (±0.7) |

Figure 4:
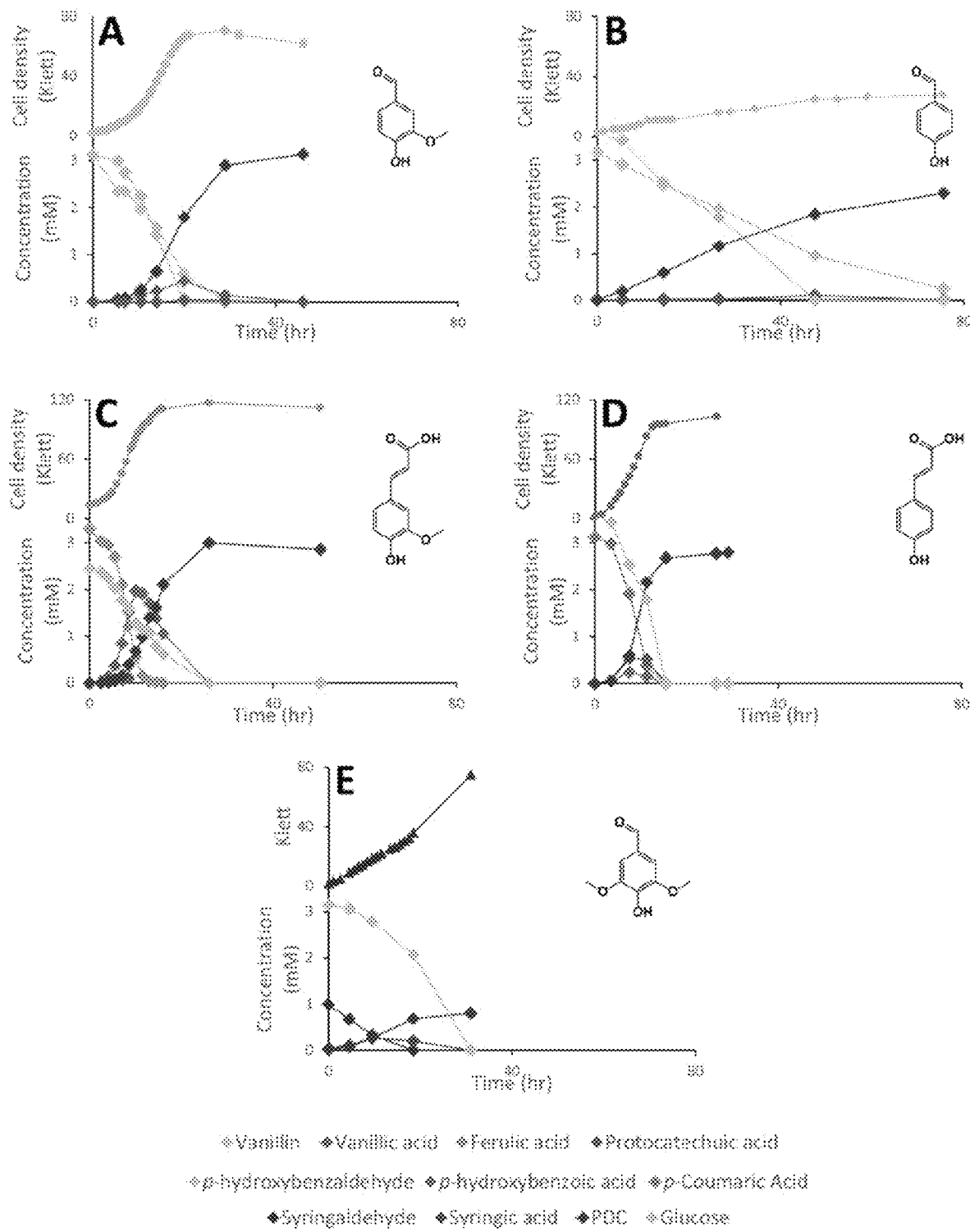
FIG. 4. Cell density and extracellular metabolite concentrations of *N. aromaticivorans* strains 12444ΔligI (solid circles) or 12444ΔligIΔdesCD (solid triangles) grown on a combination of glucose and vanillin (A), p-hydroxybenzaldehyde (B), ferulic acid (C), p-coumaric acid (D), and syringaldehyde (E).

In theory, other G and H aromatics metabolized by *N. aromaticivorans* would also produce PDC when fed to strain 12444ΔligI (FIG. 1). We tested this prediction with the G aromatics vanillin and ferulic acid and the H aromatics p-hydroxybenzaldehyde and p-coumaric acid (FIG. 4 and Table 4). Cultures grown on minimum media with 3 mM vanillin plus 3 mM glucose showed transient accumulation of vanillic acid (FIG. 4 panel A), then a nearly stoichiometric accumulation of PDC. In the cultures grown with glucose and p-hydroxybenzaldehyde (FIG. 4 panel B), a transient accumulation of extracellular p-hydroxybenzoic acid and protocatechuic acid was observed, then accumulation of PDC with a 79% (±2%) yield (Table 4). Cultures grown on ferulic acid plus glucose showed a transient accumulation of vanillic acid and protocatechuic acid (FIG. 4 panel C), then accumulation of PDC with a 76% (±10%) yield (Table 4). Similarly, the cultures grown with p-coumaric acid and glucose transiently accumulated extracellular p-hydroxybenzoic and protocatechuic acids (FIG. 4 panel D), then accumulated PDC with an efficiency of 84% (±5.4%) (Table 4).

These results are consistent with transformation of G and H aromatics via the predicted pathway of FIG. 1. The observed PDC yields (Table 4) suggest that PDC is the main intermediate that accumulates, and that disruption of the ligI gene is sufficient to prevent PDC catabolism.

Figure 5:
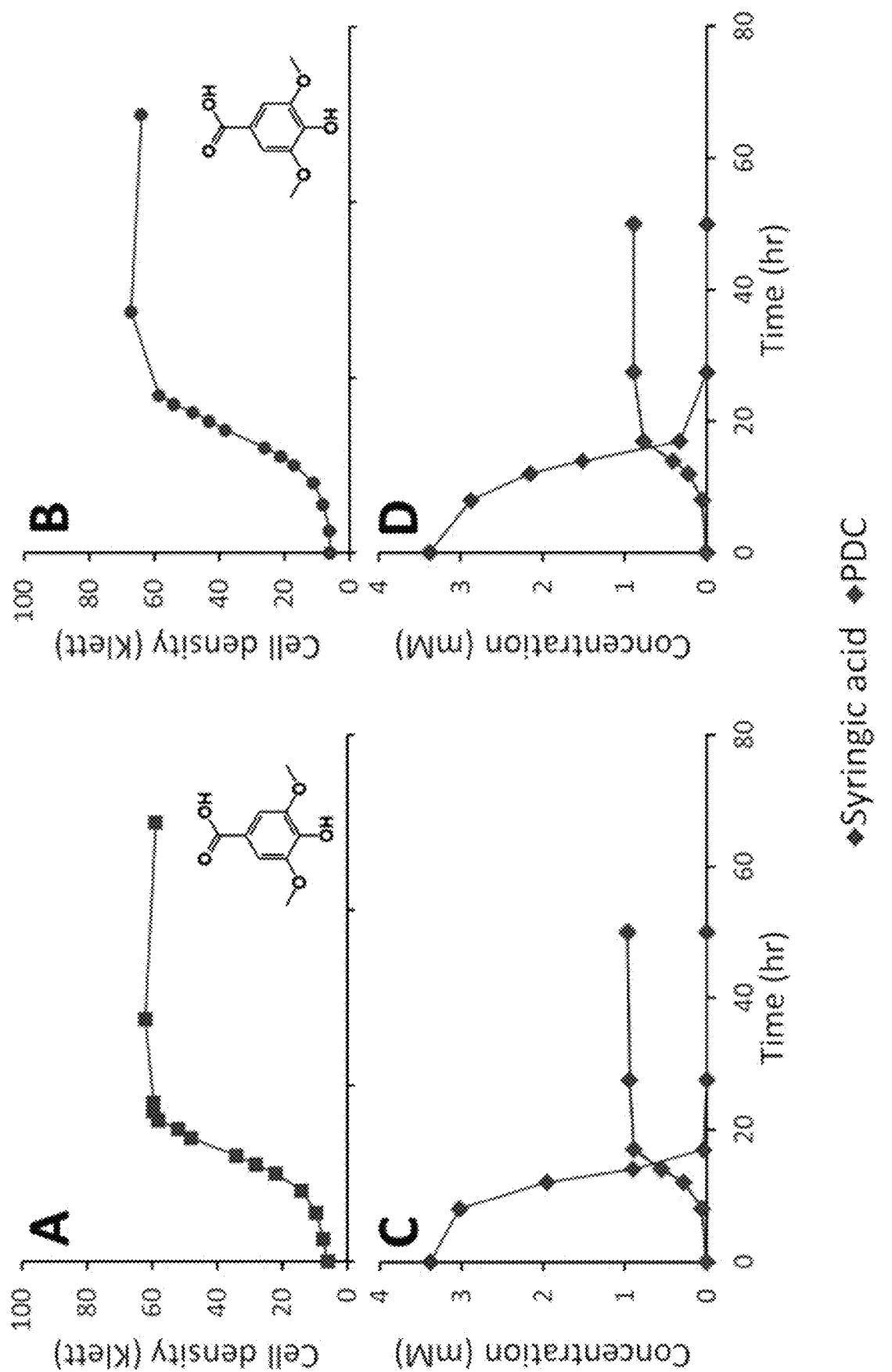
FIG. 5. Cell density and extracellular metabolite concentrations of representative cultures of *N. aromaticivorans* strains 12444Δ1879 (panels A and C) and 12444ΔligI (panels B and D) grown in media containing syringic acid.

The inability of 12444ΔligI to metabolize PDC is not predicted to affect the degradation of aromatics containing S units, since the metabolism of these compounds would follow the 3-MGA, CHMOD, OMA pathway (FIG. 1). In agreement with this hypothesis, when strain 12444ΔligI was fed 3 mM syringic acid as the sole carbon source, growth of this mutant reached final cell densities similar to those of parent strain 12444Δ1879 and this aromatic was metabolized to a similar extent in both strains (FIG. 5). This observation confirms that LigI is not necessary for syringic acid degradation. However, these experiments also showed that PDC accumulates in the growth media in both cases, representing 28% (0.97 mM) and 26% (0.89 mM) of the initial concentration of syringic acid for strains 12444Δ1879 and 12444ΔligI, respectively.

Construction of an *N. aromaticivorans* Mutant that Accumulates PDC from S Aromatics Dimethoxylated phenolics, such as syringic acid, are predicted to be degraded by *N. aromaticivorans* via the 3-MGA, CHMOD, OMA pathway (FIG. 1). Based on this prediction, we hypothesize that deleting the desCD genes would disrupt the degradation of S aromatics (FIG. 1), leading to the accumulation of the intermediate CHMOD. However, this mutation may not be sufficient to prevent growth of *N. aromaticivorans* on S aromatics because CHMOD may undergo abiotic or enzymatic transformation to PDC,[29] which could then be hydrolysed by LigI. Thus, to test these hypotheses, we constructed strain 12444ΔdesCD by deleting the desCD genes from strain 12444Δ1879.

Figure 6:
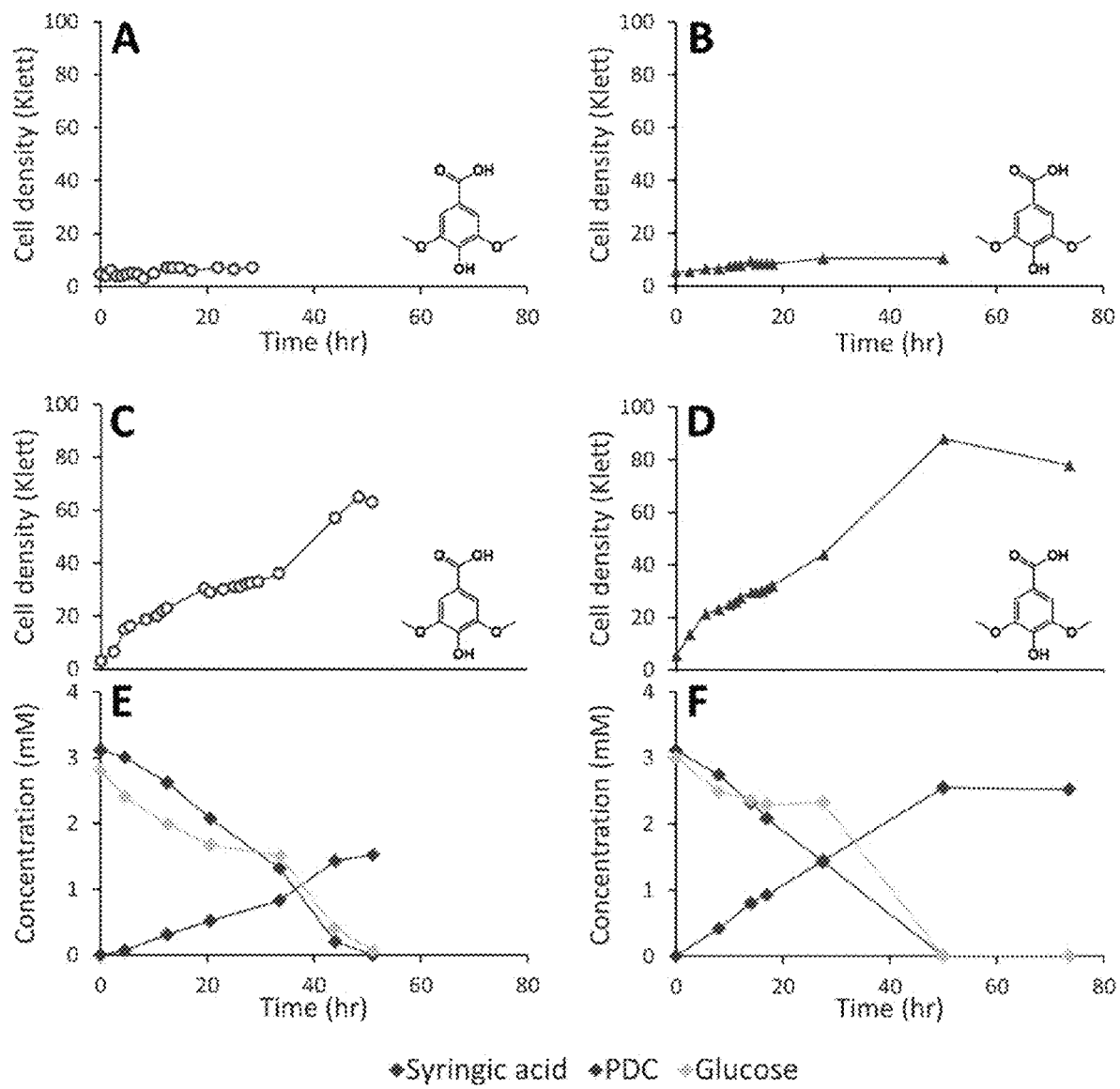
FIG. 6. Cell densities and extracellular metabolite concentrations of *N. aromaticivorans* strains 12444ΔdesCD (left-hand side panels) and 12444ΔligIΔdesCD (right-hand side panels) grown on 3 mM syringic acid (panels A and B) or a combination of 3 mM syringic acid and 3 mM glucose (panels C to F).
Figure 7:
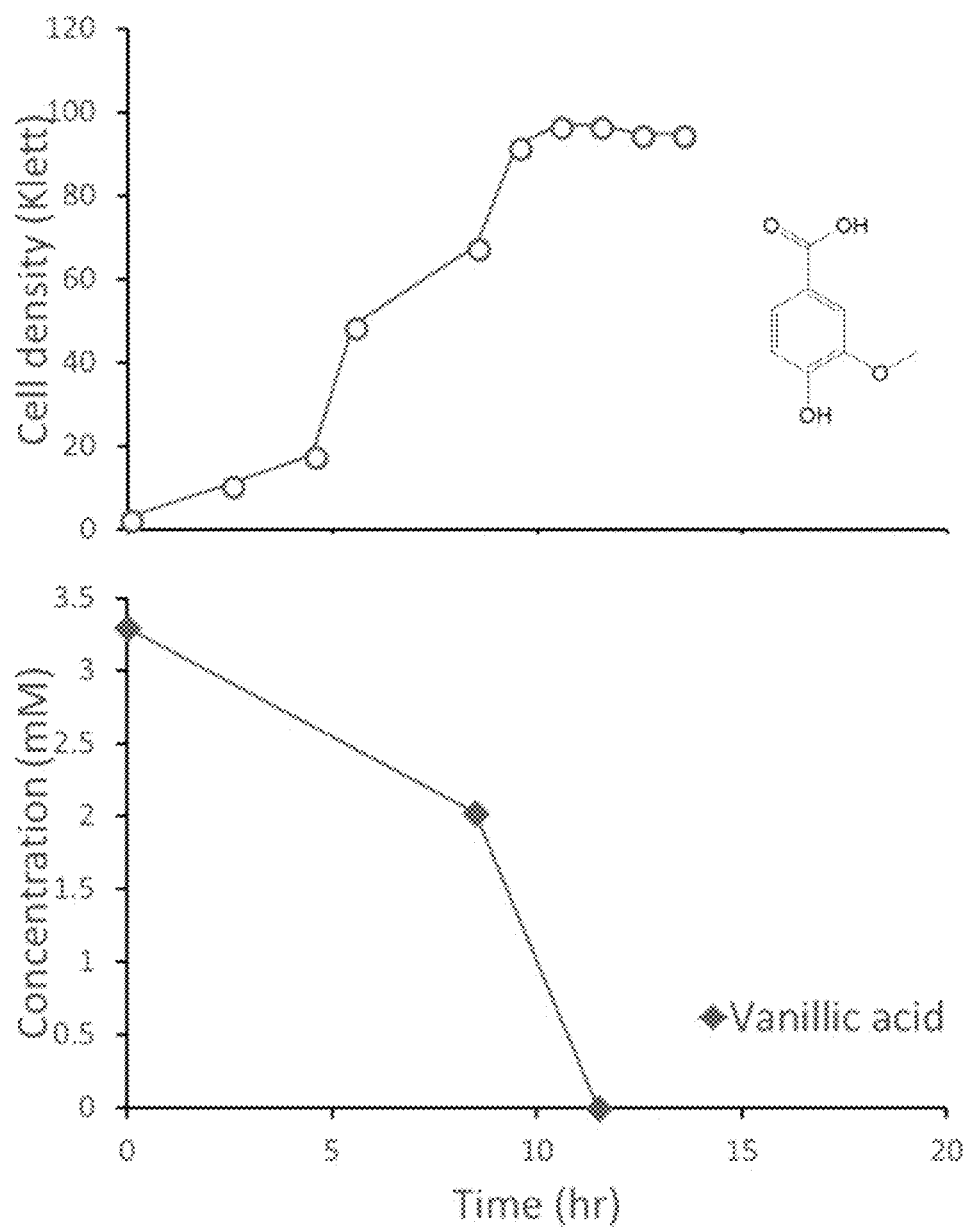
FIG. 7. Cell density and extracellular metabolite concentrations of representative *N. aromaticivorans* strain 12444ΔdesCD cultured on 3 mM vanillic acid.

Growth was not observed when strain 12444ΔdesCD was cultured in minimal media with 3 mM syringic acid as the sole carbon source (FIG. 6 panel A), indicating that either desC, desD or both genes are essential for growth on syringic acid, in agreement with observations reported previously.[2] To test the 12444ΔdesCD strain for a defect in S aromatic metabolism when growth was occurring, we inoculated the strain into media containing both 3 mM glucose and 3 mM syringic acid (FIG. 6 panel C). The 12444ΔdesCD strain grew, with consumption of both syringic acid and glucose, and with increased PDC accumulation compared to strain 12444Δ1879, converting 49% (±0.9%) of the syringic acid into PDC (versus 28% for 12444Δ1879; FIG. 5 panel C). This suggests that increased cyclization of CHMOD to PDC took place, although this observation is not sufficient to determine whether the reaction is abiotic or enzymatic. Growth of 12444ΔdesCD on vanillic acid as the only carbon source demonstrated that the disruption in desCD does not affect the catabolism of G units and does not lead to detectable PDC accumulation (FIG. 7).

Construction of an *N. aromaticivorans* Mutant that Accumulates PDC from S, G, and H Aromatics Based on the observations with strains 12444ΔligI and 12444ΔdesCD, we hypothesized that a mutant missing ligI and desCD would be able to produce a higher yield of PDC from S aromatics. We generated this strain (12444ΔligIΔdesCD) and found that when it was cultured in minimal media with 3 mM syringic acid as the sole carbon source, it did not grow, as expected from previously presented data (FIG. 6 panel B). When glucose was added to the growth media, strain 12444ΔligIΔdesCD grew (FIG. 6 panel D), glucose and syringic acid were removed from the media, and PDC accumulated (FIG. 6 panel F). Indeed, the PDC yield of 12444ΔligIΔdesCD (66%±13%), was higher than that of 12444ΔdesCD (49%±0.9%) (Table 4).

PDC production from syringaldehyde by strain 12444ΔligIΔdesCD was also tested. When this strain was grown on 1 mM syringaldehyde plus 3 mM glucose (FIG. 4 panel E), syringaldehyde disappeared from the growth media, syringic acid was transiently detected, and PDC accumulated with a 90% (±7%) yield (Table 4).

The Fate of Unconverted Aromatic Carbon

Since PDC yields were typically less than 100%, it is possible that some aromatic compounds are degraded via alternative routes not blocked by the ΔligI and ΔdesCD mutations, and therefore, a fraction of aromatics may be still used as carbon and energy sources for growth in strain 12444ΔligIΔdesCD. To evaluate this hypothesis, we compared cell yields in 12444ΔligIΔdesCD cultures grown on either 3 mM glucose or 3 mM glucose plus 3 mM protocatechuic acid. The cultures grown on glucose reached a final density of 165 (±1) Klett units and no glucose or PDC was detected in the culture media (Table 5). The cultures receiving glucose plus protocatechuic acid reached a final cell density of 202 (±2) Klett units (Table 5). In these cultures, all glucose was consumed and 0.2 mM (±0.03) protocatechuic acid remained in the growth media (Table 5). The calculated yield of PDC based on the consumed protocatechuic acid was 85% (±1%) (Table 5). Since in both conditions the same amount of glucose was provided, the higher cell density observed in the cultures containing glucose plus protocatechuic acid can be explained by the use of a fraction of protocatechuic as a carbon and energy source for cell growth, presumably via a less efficient alternative pathway. The absence of PDC in the cultures containing only glucose shows that strain 12444ΔligIΔdesCD does not produce PDC from glucose.

TABLE 5

Comparison of cell densities and extracellular concentrations at stationary phase of *N. aromaticivorans* strain 12444ΔligIΔdesCD cultures grown on glucose or glucose plus protocatechuic acid. Data shown represents the average of 3 biological replicates. Error bars represent ± one standard deviation.

|  | Glucose | Glucose + protocatechuic acid |
|---|---|---|
| Maximum cell density (Klett) | 165.3 (±0.58) | 201.7 (±2.08) |
| Metabolites concentration immediately after inoculation | | |
| Glucose (mM) | 3.1 (±0.02) | 3.1 (±0.04) |
| Protocatechuic acid (mM) | 0.0 | 2.9 (±0.02) |
| PDC (mM) | 0.0 | 0.0 |
| Metabolites concentration at stationary phase | | |
| Glucose (mM) | 0.0 | 0.0 |
| Protocatechuic acid (mM) | 0.0 | 0.2 (±0.03) |
| PDC (mM) | 0.0 | 2.3 (±0.04) |
| PDC yield (%) | 0.0 | 85 (±1.10) |

Production of PDC from Chemically Depolymerized Lignin

Figure 9:
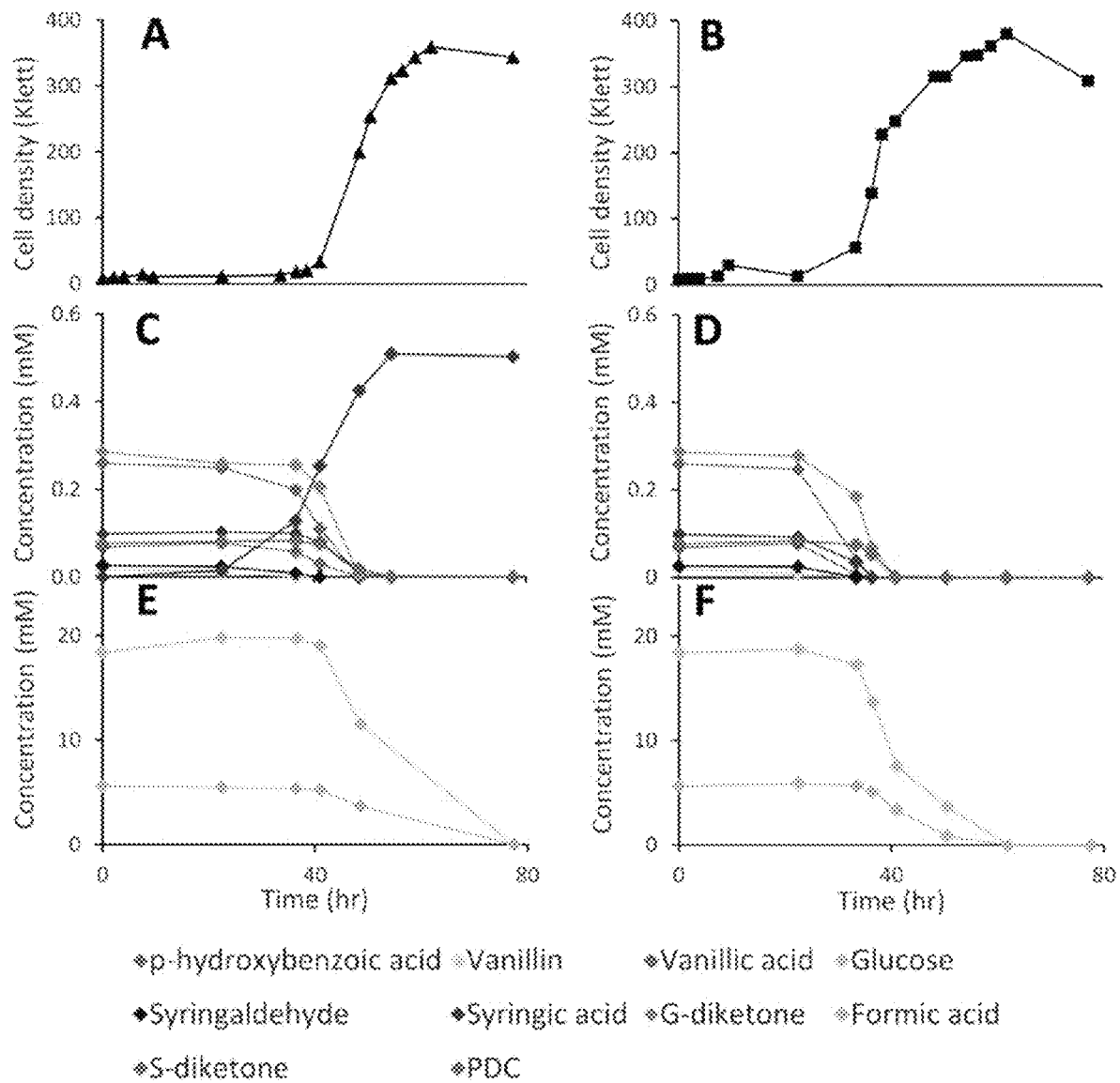
FIG. 9. Cell density (panels A and B) and extracellular metabolite concentrations (panels C to F) of representative cultures of N. aromaticivorans strains 12444ΔligIΔdesCD (left-hand side panels) and 12444Δ1879 (right-hand side panels) grown on formic-acid-induced depolymerized poplar lignin supplemented with glucose. Panels C and D show extracellular concentrations of lignin-derived aromatic compounds and PDC as a product, and panels E and F show extracellular concentrations of glucose and formic acid. Formic acid is present in the low molecular weight products of chemical depolymerization, whereas glucose was added to enhance bacterial cell growth.
Figure 10A:
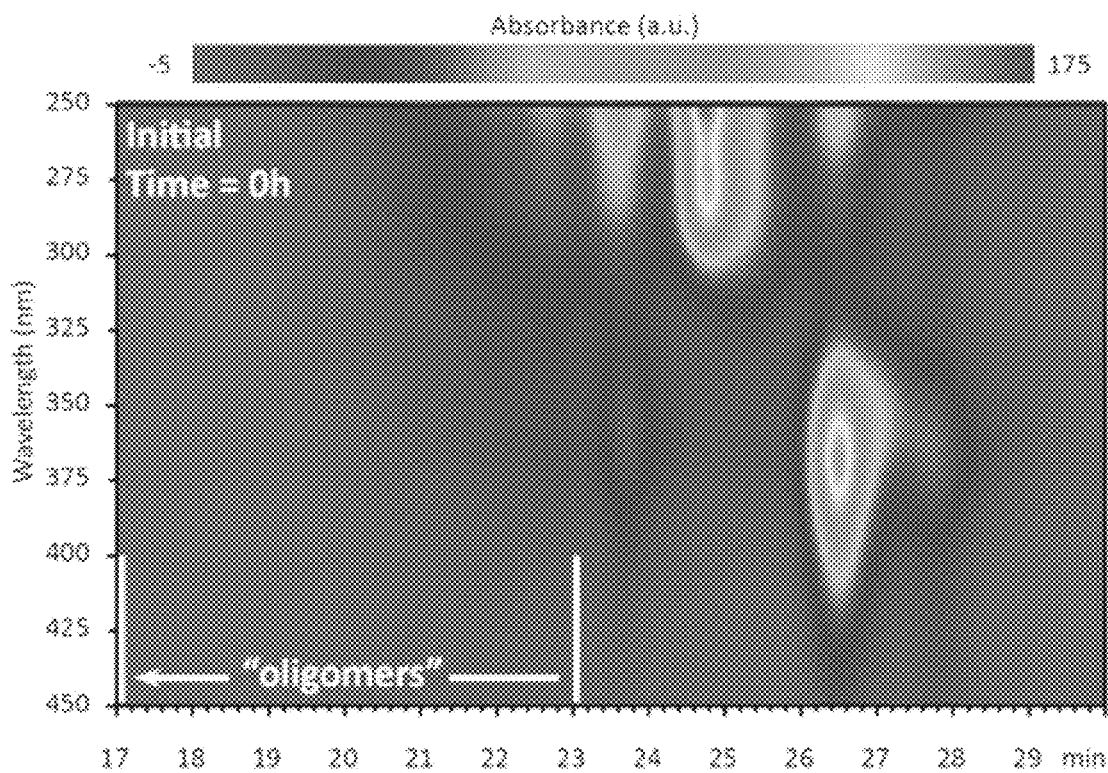
FIGS. 10A-10D. GPC chromatograms of media containing glucose plus the products of formic-acid-induced depolymerization of oxidized poplar lignin; before inoculation (FIG. 10A), abiotic control after 78 hours of incubation (FIG. 10B), after growth of N. aromaticivorans strain 12444Δ1879 (FIG. 10C), after growth of N. aromaticivorans strain 12444ΔligIΔdesCD (FIG. 10D).
Figure 10B:
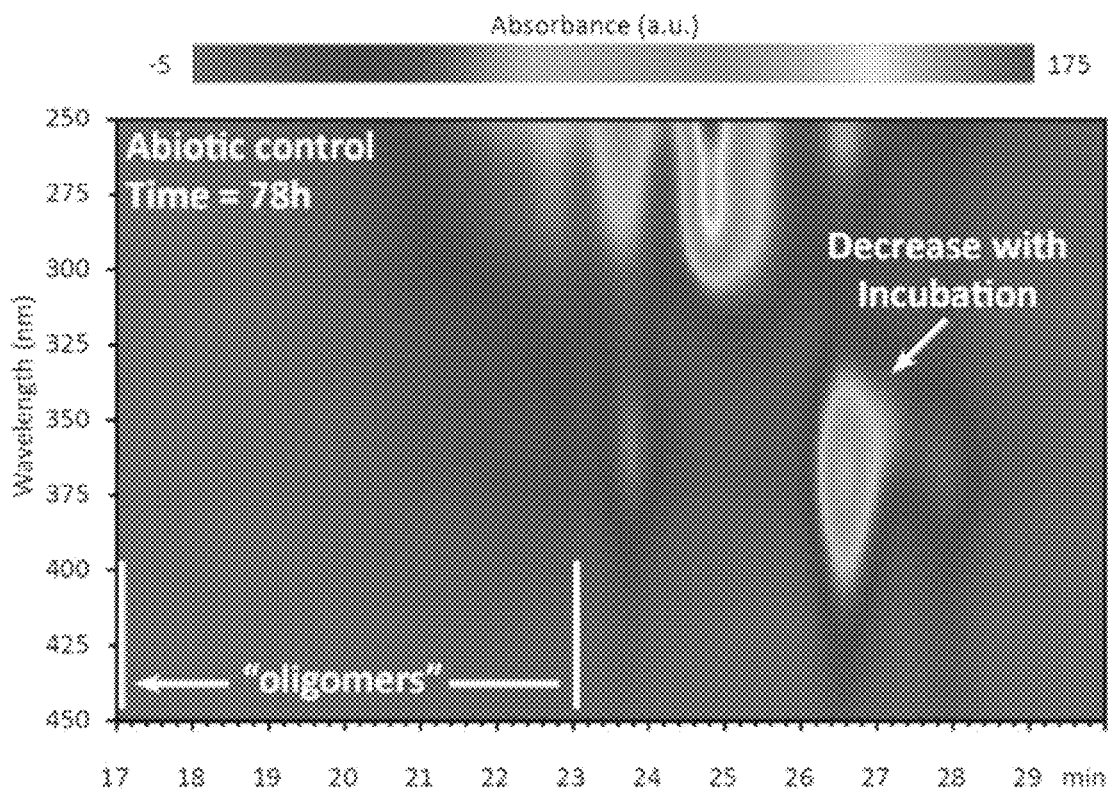
Figure 10C:
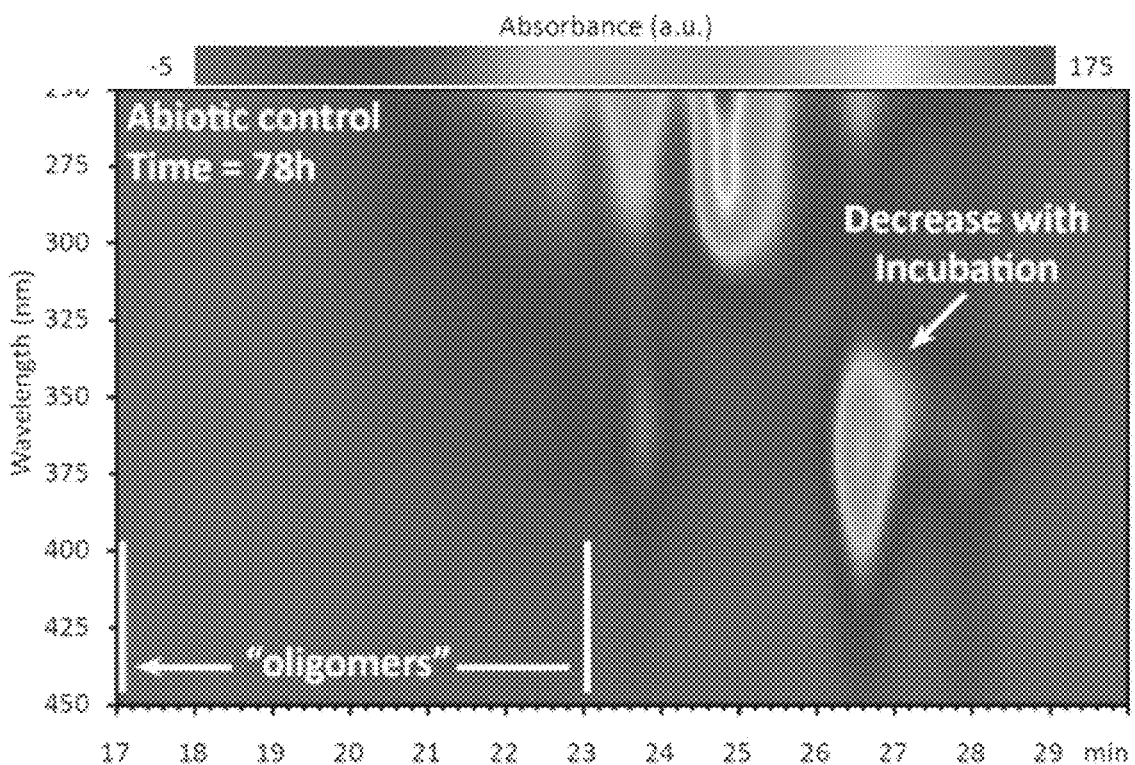
Figure 10D:
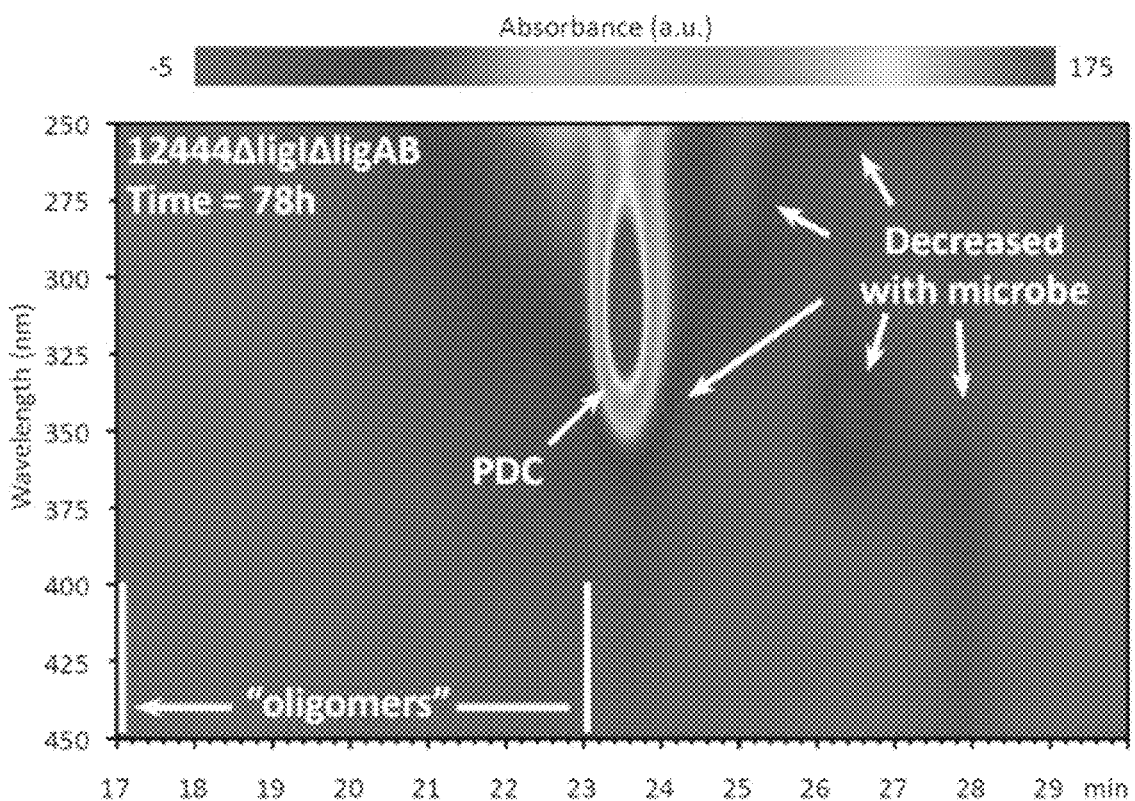

Lignocellulosic biomass pretreatment and chemical depolymerization of lignin typically result in heterogeneous mixtures of aromatics with variable molar yields of monomers recovered.[6,7] Based on the above results, a strain lacking both LigI and DesCD activity might also be able to simultaneously convert all three classes (S, G, and H) of plant-derived aromatics into PDC. To test the ability of strain 12444ΔligIΔdesCD to produce PDC simultaneously from multiple S, G, and H aromatic compounds, we cultured it in glucose-containing media supplemented with the products of depolymerized poplar lignin,[4] which contained a mixture of S, G, and H aromatic compounds (FIG. 9). For comparison, strain 12444Δ1879 was cultured in the same media. In addition, a flask containing the same media without cells was incubated as an abiotic control. A large proportion of the aromatic compounds present in this type of depolymerized lignin are S and G type diketones[4] and no information has been previously reported about the ability of bacteria to degrade them. Thus, in the experiments below we also tested for metabolism of the S and G diketones and their potential conversion into PDC.

Figure 8:
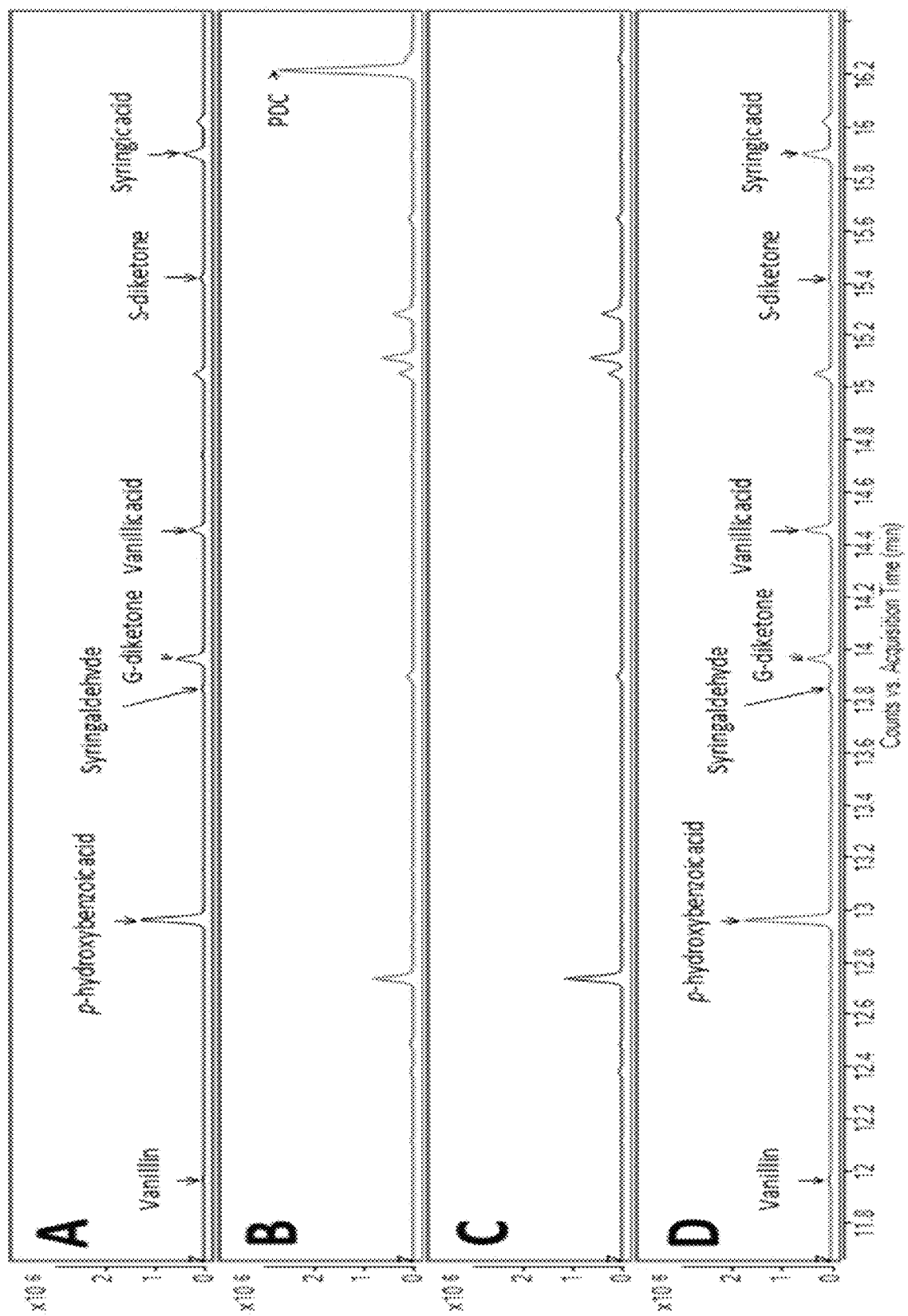
FIG. 8. GC-MS peaks of compounds identified in media containing glucose plus the products of formic-acid-induced depolymerization of oxidized poplar lignin; before inoculation (A), after growth of *N. aromaticivorans* strain 12444ΔligIΔdesCD (B), after growth of *N. aromaticivorans* strain 12444Δ1879 (C). Only strain 12444ΔligIΔdesCD accumulates PDC in the growth medium. Panel D shows the absence of additional peaks in an abiotic control experiment.

In the abiotic control, none of the aromatic compounds were transformed after 77.5 h of incubation (FIG. 8 panel D, FIGS. 10A-10D, and FIG. 11). In the inoculated cultures, both strains grew, and, in both cases, all the major aromatic compounds (G-diketone, S-diketone, p-hydroxybenzoic acid, vanillin, vanillic acid, syringaldehyde, and syringic acid) disappeared from the growth media (FIG. 9 and FIG. 8 panels B and C). PDC only accumulated in the 12444ΔligIΔdesCD cultures, reaching a concentration of 0.49 mM (±0.02), which corresponds to a molar yield of 59% (±1.9%) assuming that all of the above aromatics were used as a source of this compound (FIG. 9).

Figure 11:
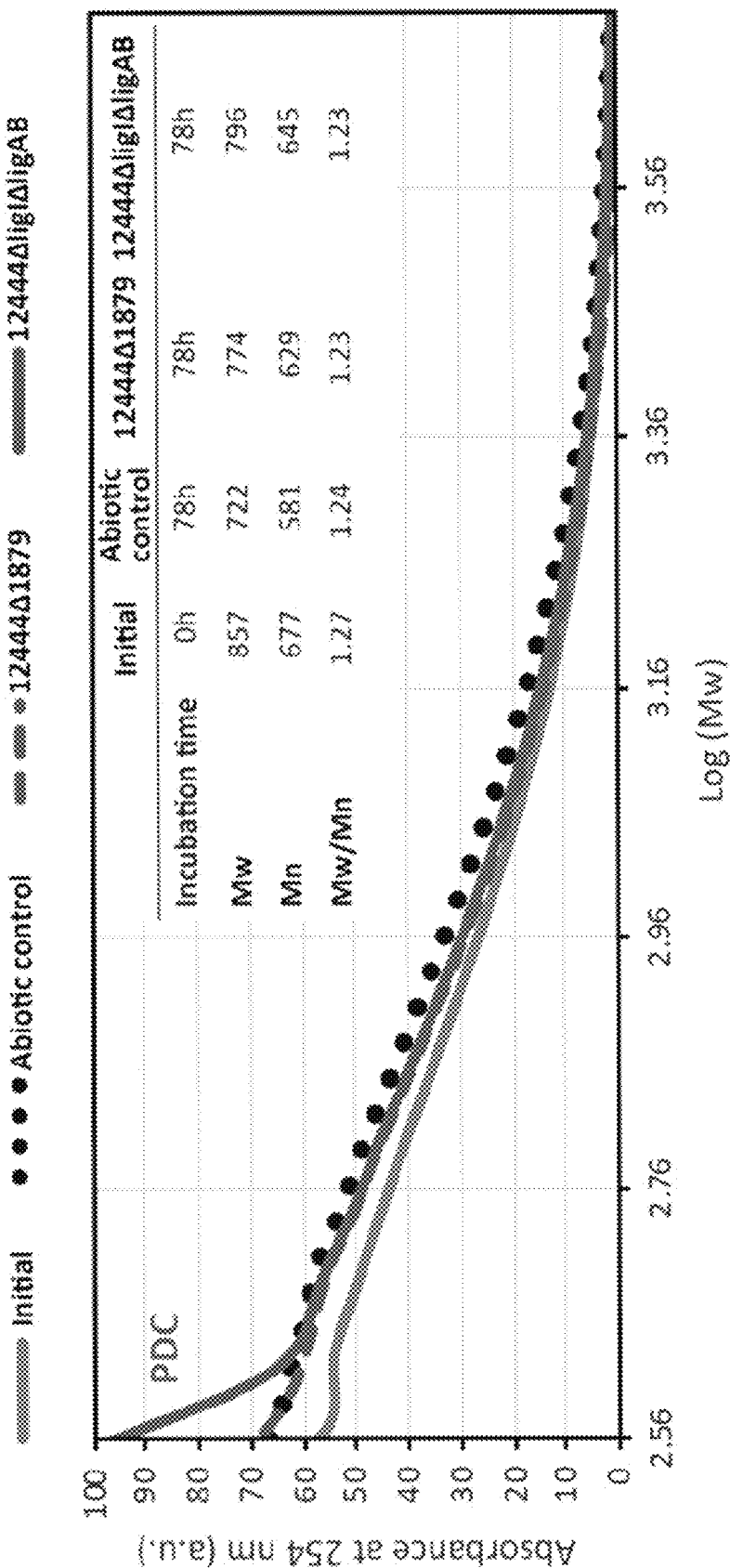
FIG. 11. GPC chromatogram of the "oligomers" range at λ=254 of media containing glucose plus the products of formic-acid-induced depolymerization of oxidized poplar lignin. Mw: weight average molecular weight; Mn: number average molecular weight; Mw/Mn: dispersity index.

Gel permeation chromatography (GPC) was performed to determine the presence of, and evaluate changes in, oligomeric lignin fragments found in these depolymerized lignin samples (FIGS. 10A-10D and 11). This analysis showed presence of compounds with a wide range of molecular weights ($M_w$), which we grouped in 2 ranges (see Materials and methods). Based on the analysis of standards, compounds eluting between 17.0 and 22.7 min corresponded to oligomeric lignin fragments, while compounds eluting after 22.7 min are dimeric and monomeric compounds. An abiotic control showed that during 78 hours of incubation there was an observable increase in low $M_w$ oligomers, likely from reactive monomer condensation, that resulted in an average $M_w$ decrease from 857 to 722 Da (FIG. 11). Both microbial cultures showed a decrease in the dimeric and monomeric compounds (signals eluting after 22.7 min) compared to the abiotic control sample. As with the sample before incubation, both microbial cultures showed the decrease in oligomer $M_w$ attributed to reactive monomer condensation, but not as much as in the abiotic control (FIG. 11). Accumulation of PDC in experiments with 12444ΔligIΔdesCD was observable by a peak at 23.55 min (FIGS. 10A-10D), corresponding to that of the PDC standard, which was not observed in the abiotic control or the experiment with the parent strain 12444Δ1879.

Figure 12:
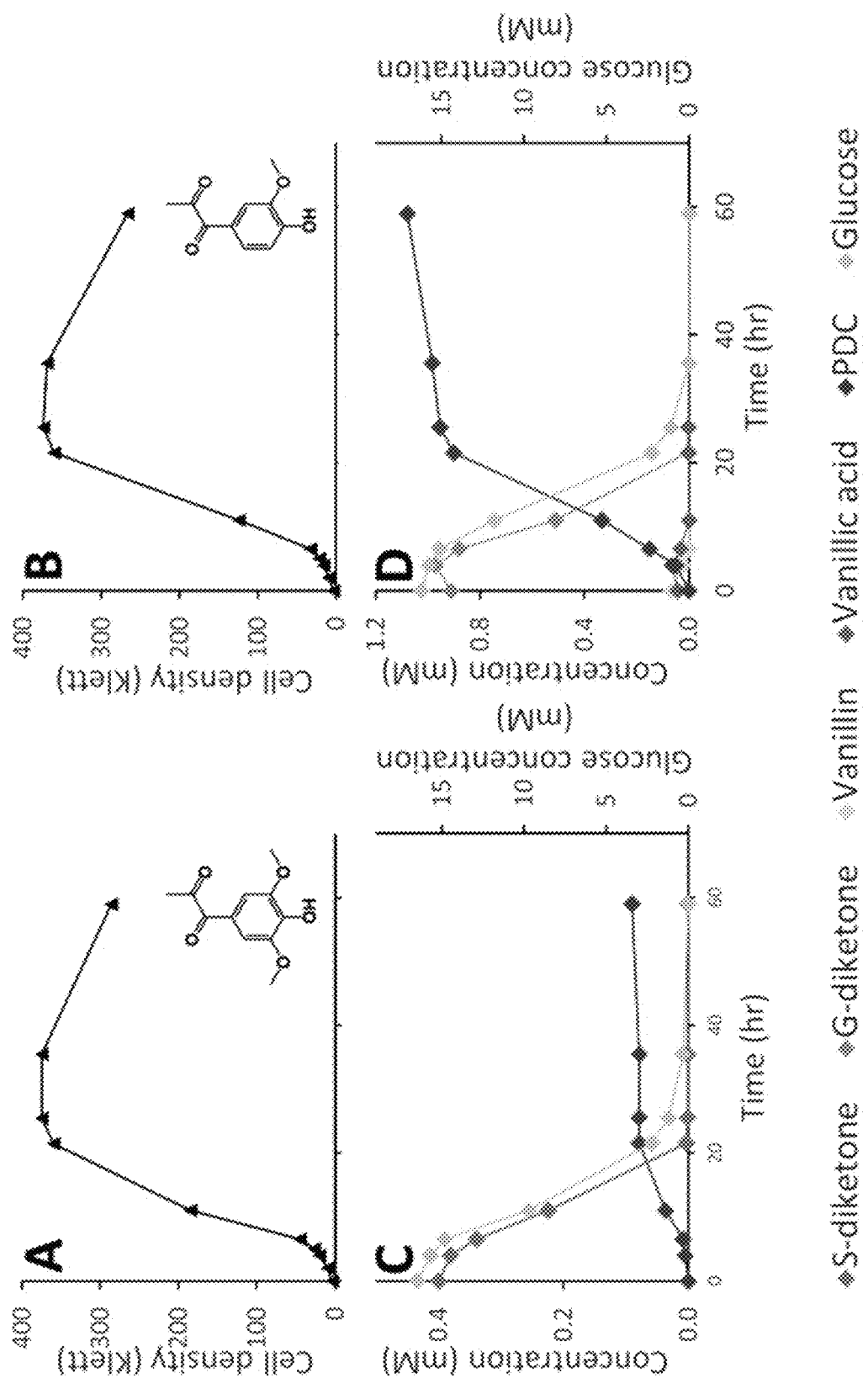
FIG. 12. Cell density and extracellular metabolite concentrations of representative N. aromaticivorans strain 12444ΔligIΔdesCD cultures grown on minimal media supplemented with S-diketone and glucose (panels A and C) or G-diketone and glucose (panels B and D).

While the above data suggest that 12444ΔligIΔdesCD is able to convert the G, S, and H units found in depolymerized lignin into PDC, the lack of stoichiometric conversion into PDC makes it difficult to assess how well each substrate is metabolized and converted into this product. To specifically test PDC production from the S and G aromatic diketones, we grew cultures of *N. aromaticivorans* strain 12444ΔligIΔdesCD on minimum media supplemented with chemically synthesized S-diketone plus glucose or G-diketone plus glucose (see elsewhere herein for aromatic diketone synthesis procedures). In the cultures containing S-diketone, 12444ΔligIΔdesCD grew, glucose and the aromatic diketone disappeared from the growth media, and PDC accumulated with a yield of 22.0% (±0.7%) (Table 4, FIG. 12 panels A and C). On the other hand, in the cultures supplemented with G-diketone (which contained small amounts of vanillic acid and vanillin as impurities from the synthesis method) both glucose and the aromatic substrates disappeared and PDC accumulated (FIG. 12 panels B and D), with a nearly stoichiometric yield (107%±1.6%, Table 4) for G-diketone (assuming a 100% yield from the vanillic acid and vanillin impurities). From this, we conclude that strain 12444ΔligIΔdesCD metabolizes these S and G diketones, using pathways that are also involved in degradation of the S, G and H aromatics normally found in lignin, and converts them into PDC, albeit at different efficiencies.

Production of PDC from Vanillic Acid and Vanillin in a Fed-Batch Reactor

Figure 13:
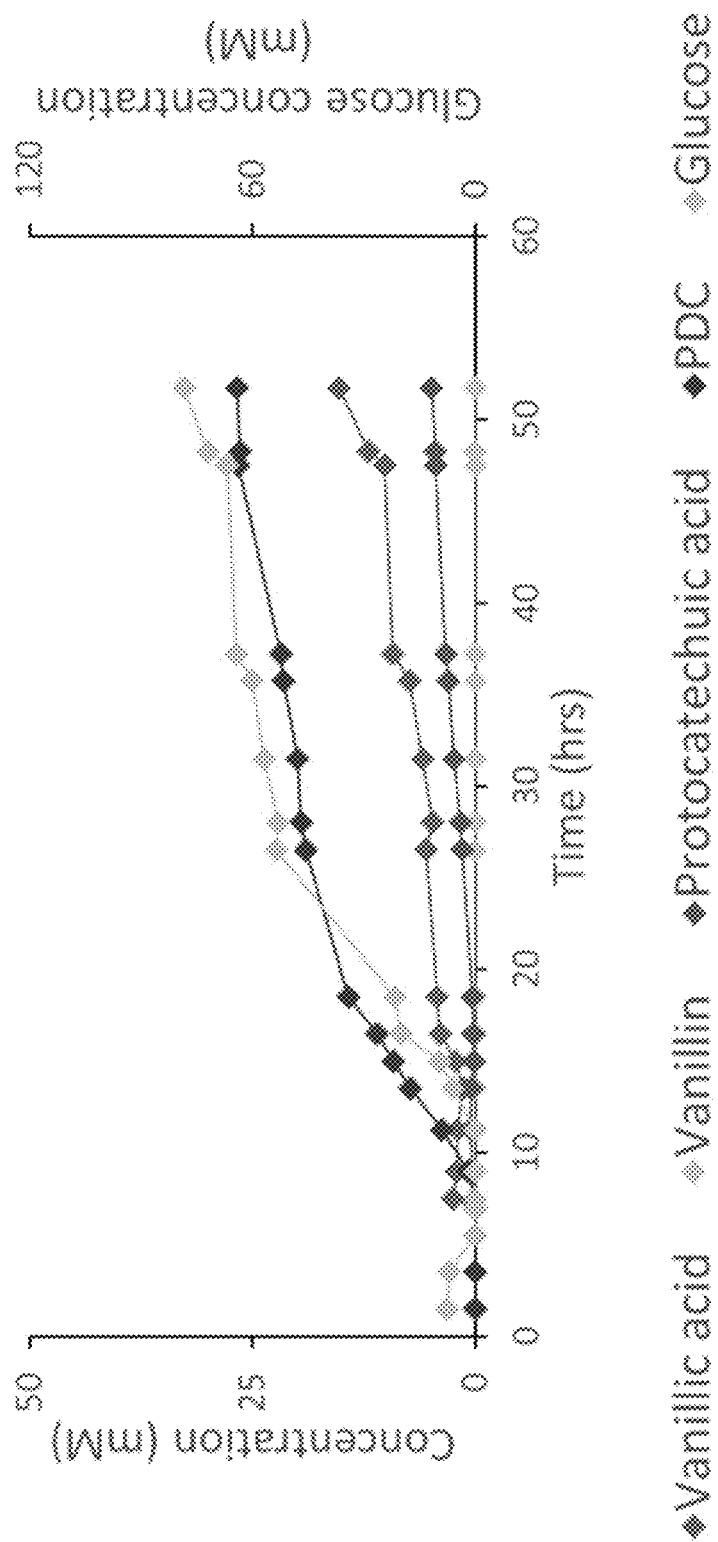
FIG. 13. Extracellular metabolite concentrations of a N. aromaticivorans strain 12444ΔligIΔdesCD culture fed with a concentrated mixture of vanillic acid, vanillin, and glucose. A maximum PDC concentration of 26.7 mM was observed after 48 hours of cultivation.

To study the feasibility of PDC production by strain 12444ΔligIΔdesCD at titers higher than those observed in batch cultures, we cultured the mutant strain in a pH-controlled fed-batch reactor in which a concentrated solution containing vanillic acid, vanillin, and glucose was intermittently fed. In this experiment, a maximum concentration of 26.7 mM (4.9 g L$^{-1}$) of PDC was reached after 48 hours of incubation (FIG. 13), which represents a more than 8 times higher concentration than observed in the batch experiments reported here. As the reaction progressed, an accumulation of glucose, vanillic, and protocatechuic acid was observed.

Production of PDC from Various Lignocellulosic Biomass Preparations

The ability of the *N. aromaticivorans* 12444ΔligIΔdesCD strain to produce PDC from different lignocellulosic biomass preparations was tested.

Figure 14A:
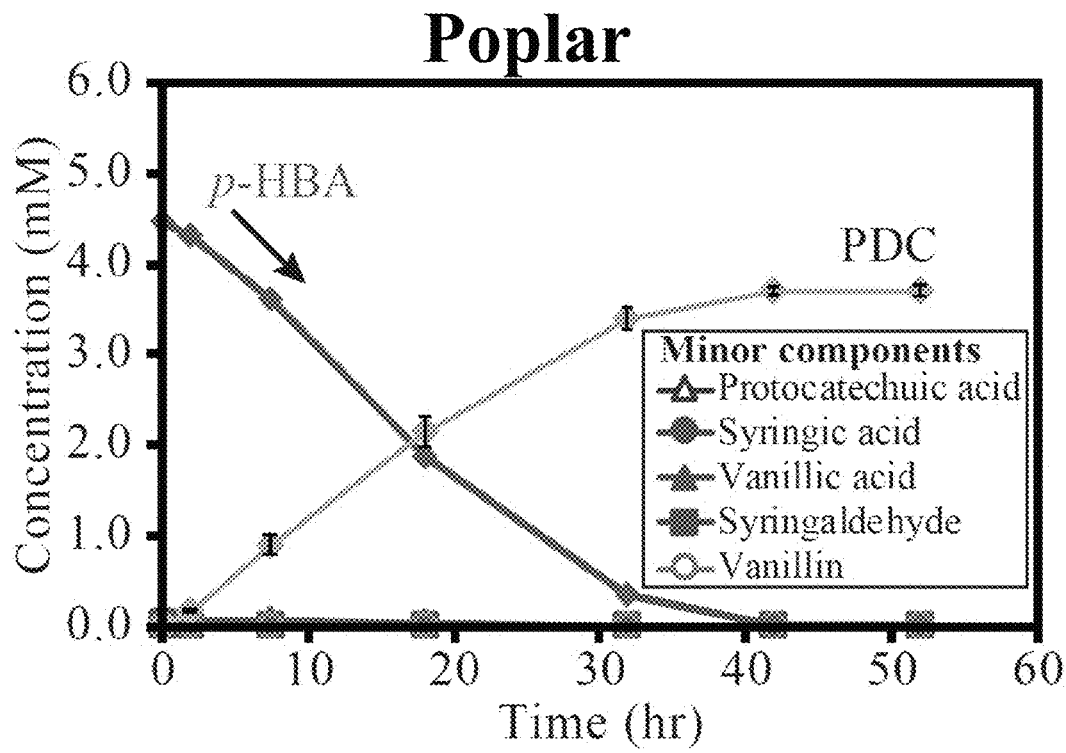
FIGS. 14A and 14B. Production of PDC from mild alkaline-pretreated poplar (FIG. 14A) and sorghum (FIG. 14B) lignocellulosic biomass with the N. aromaticivorans 12444ΔligIΔdesCD strain.
Figure 14B:
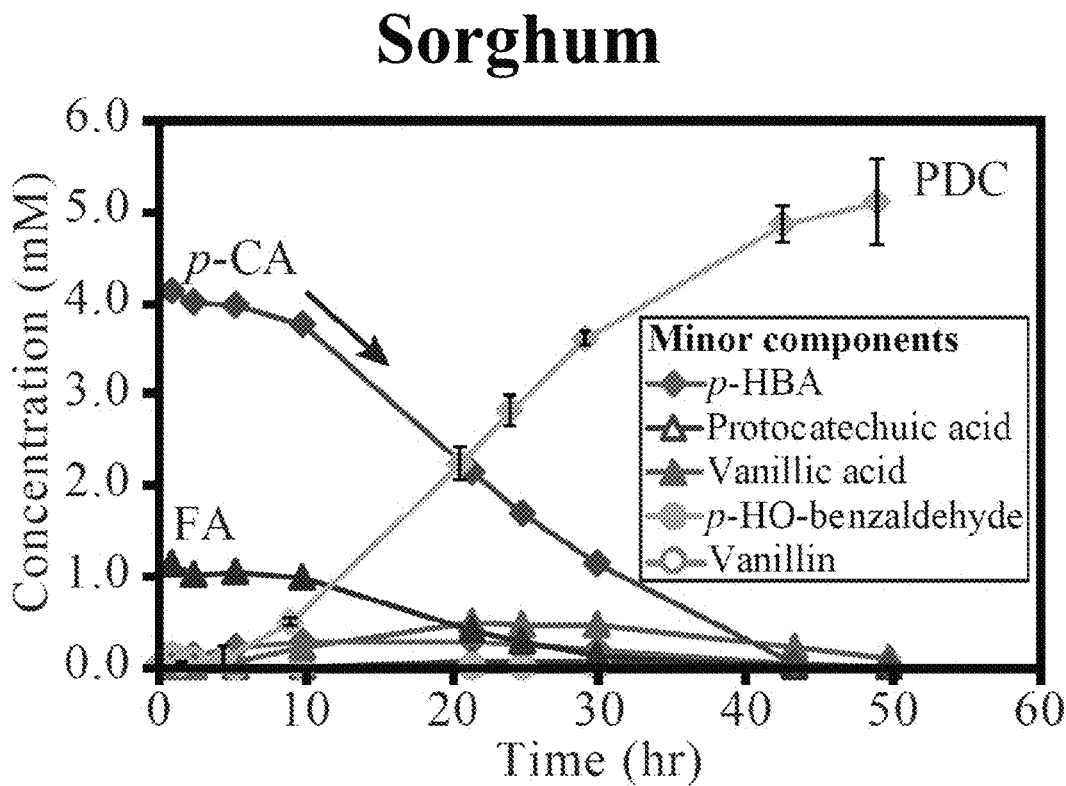

The production of PDC from poplar and sorghum lignocellulosic biomass prepared using mild alkaline pretreatment[47] was tested with the *N. aromaticivorans* 12444ΔligIΔdesCD strain. High amounts of PDC from both of these lignocellulosic biomass preparations was produced (FIGS. 14A and 14B).

Figure 15A:
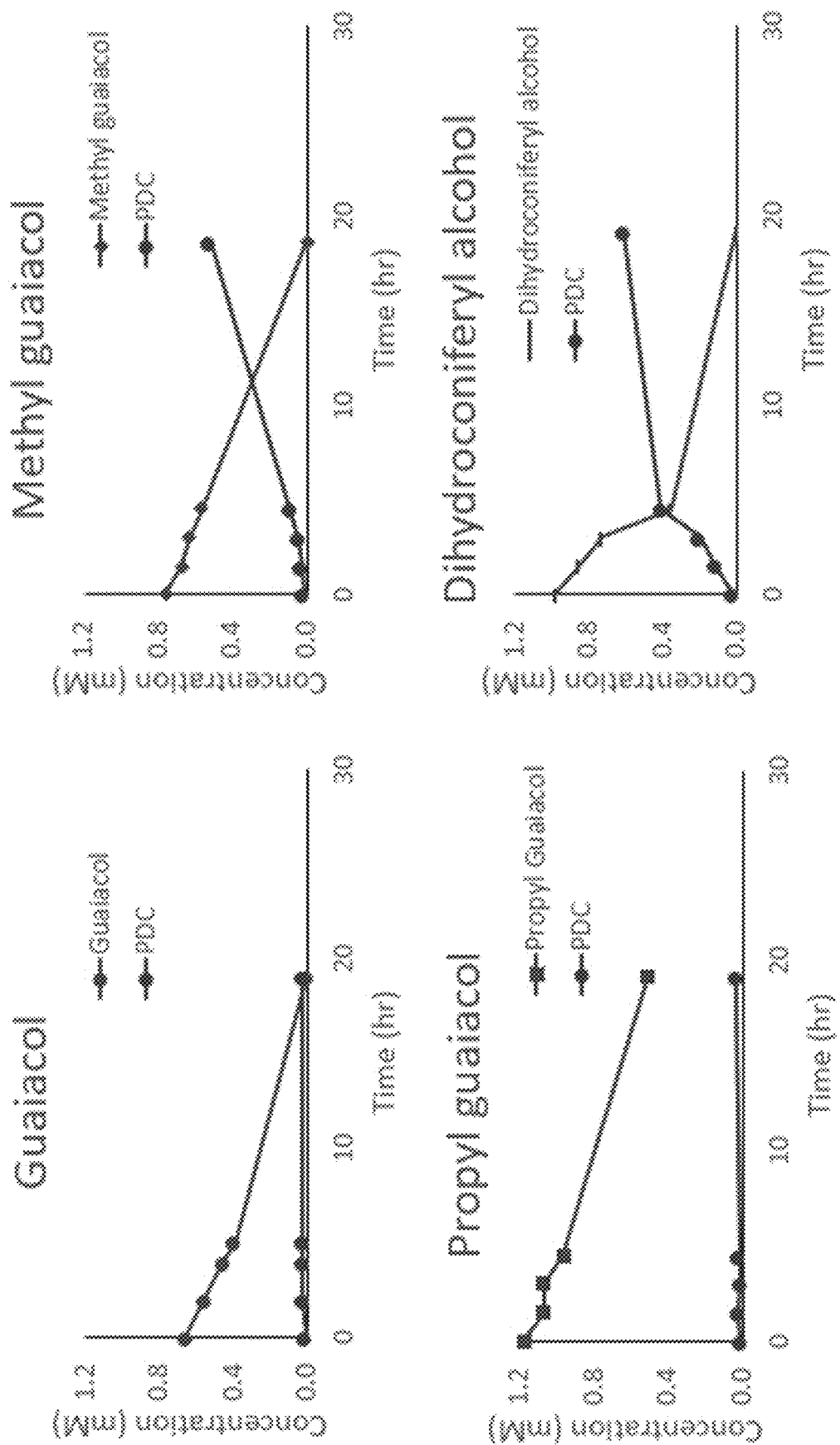
FIGS. 15A-15C. Production of PDC from isolated compounds found in depolymerized lignocellulosic biomass pretreated with γ-valerolactone (GVL) and subjected to hydrogenolysis, using the N. aromaticivorans 12444ΔligIΔdesCD strain.
Figure 15B:
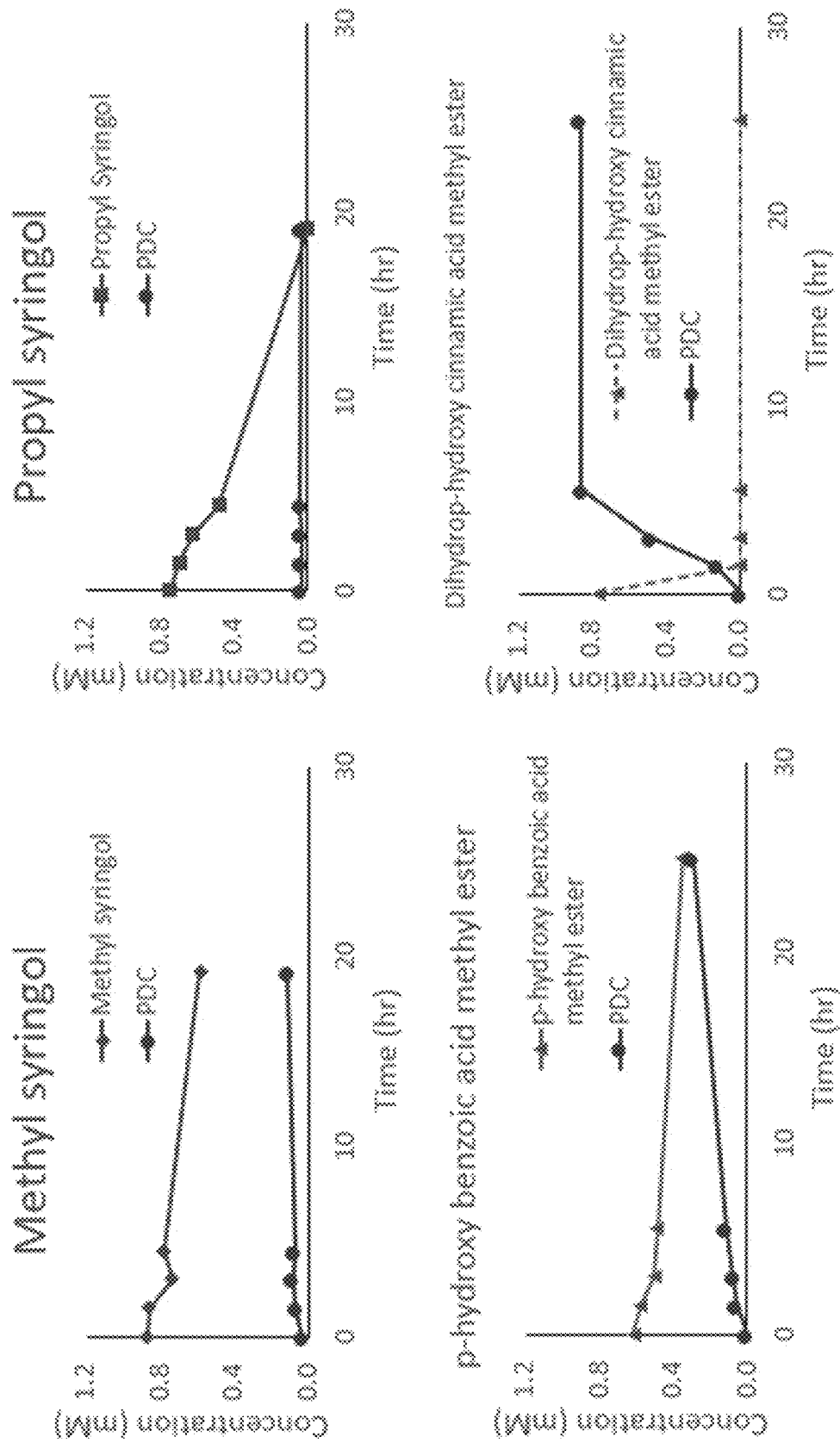
Figure 15C:
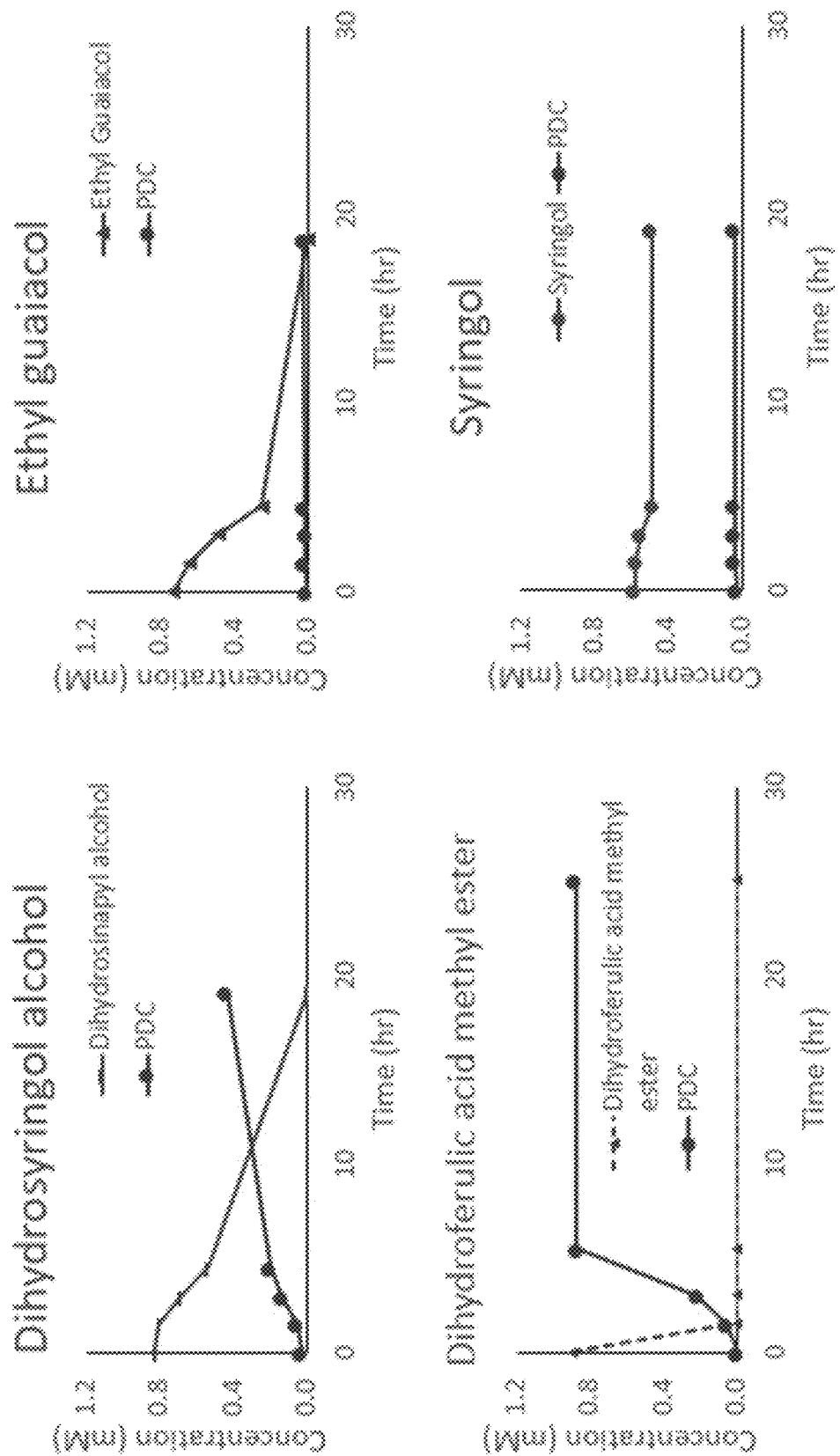
Figure 16A:
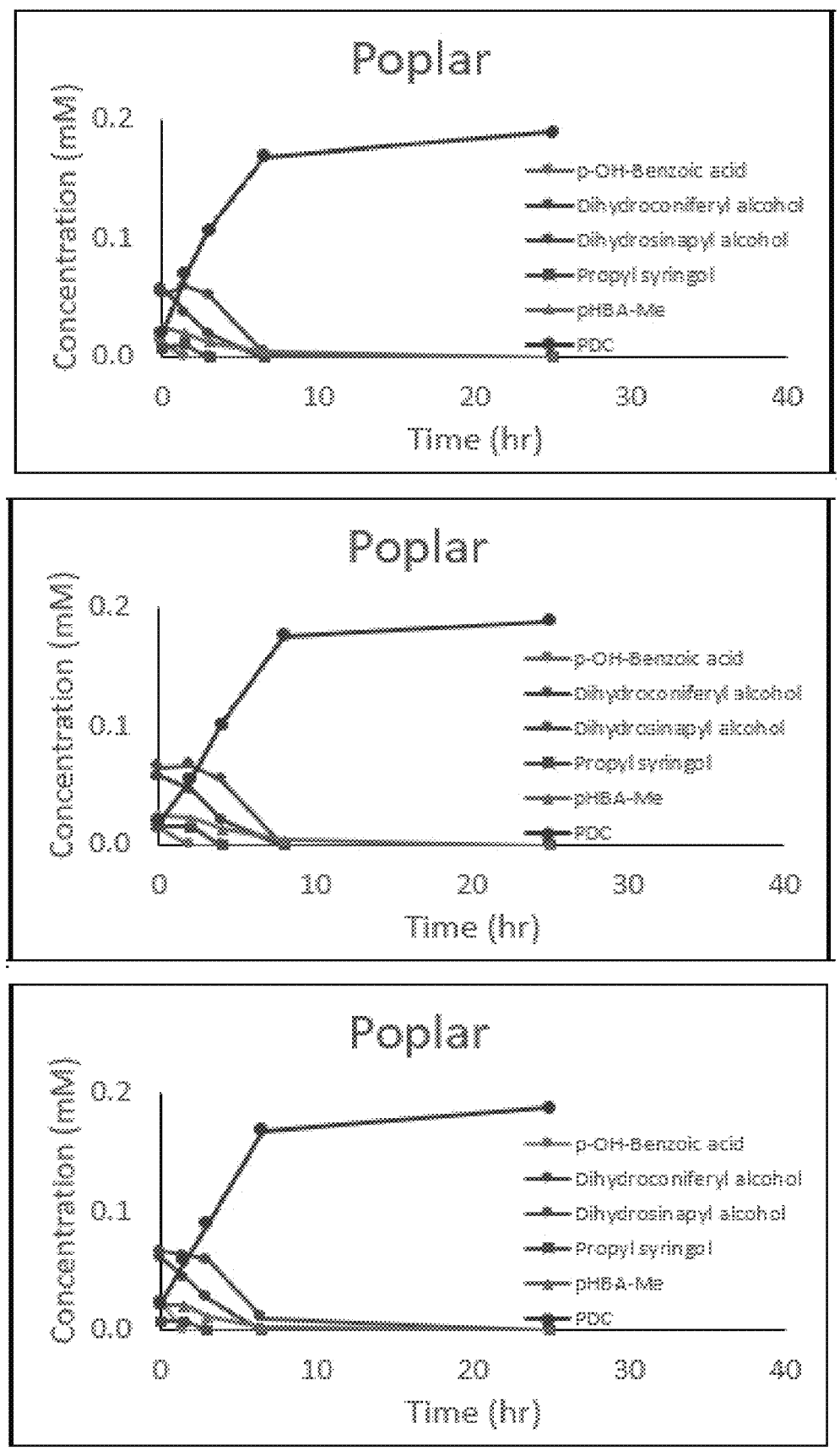
FIGS. 16A-16D. Production of PDC from poplar (FIG. 16A), switchgrass (FIG. 16B), sorghum (FIG. 16C), and maple (FIG. 16D) lignin isolated from lignocellulosic biomass pretreated with γ-valerolactone (GVL) and subjected to hydrogenolysis, using the N. aromaticivorans 12444ΔligIΔdesCD strain. Triplicate experiments with each biomass substrate are shown.
Figure 16B:
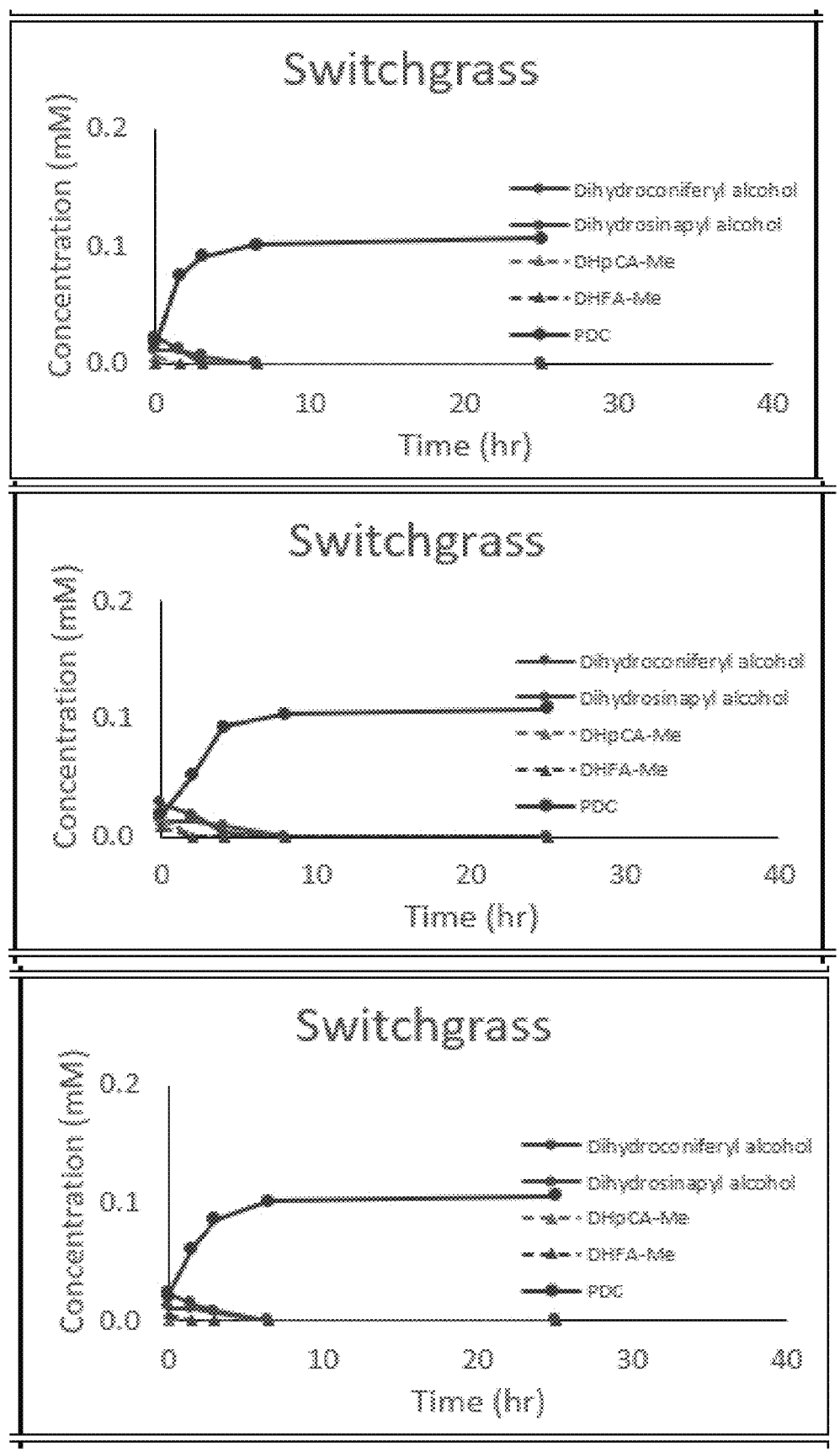
Figure 16C:
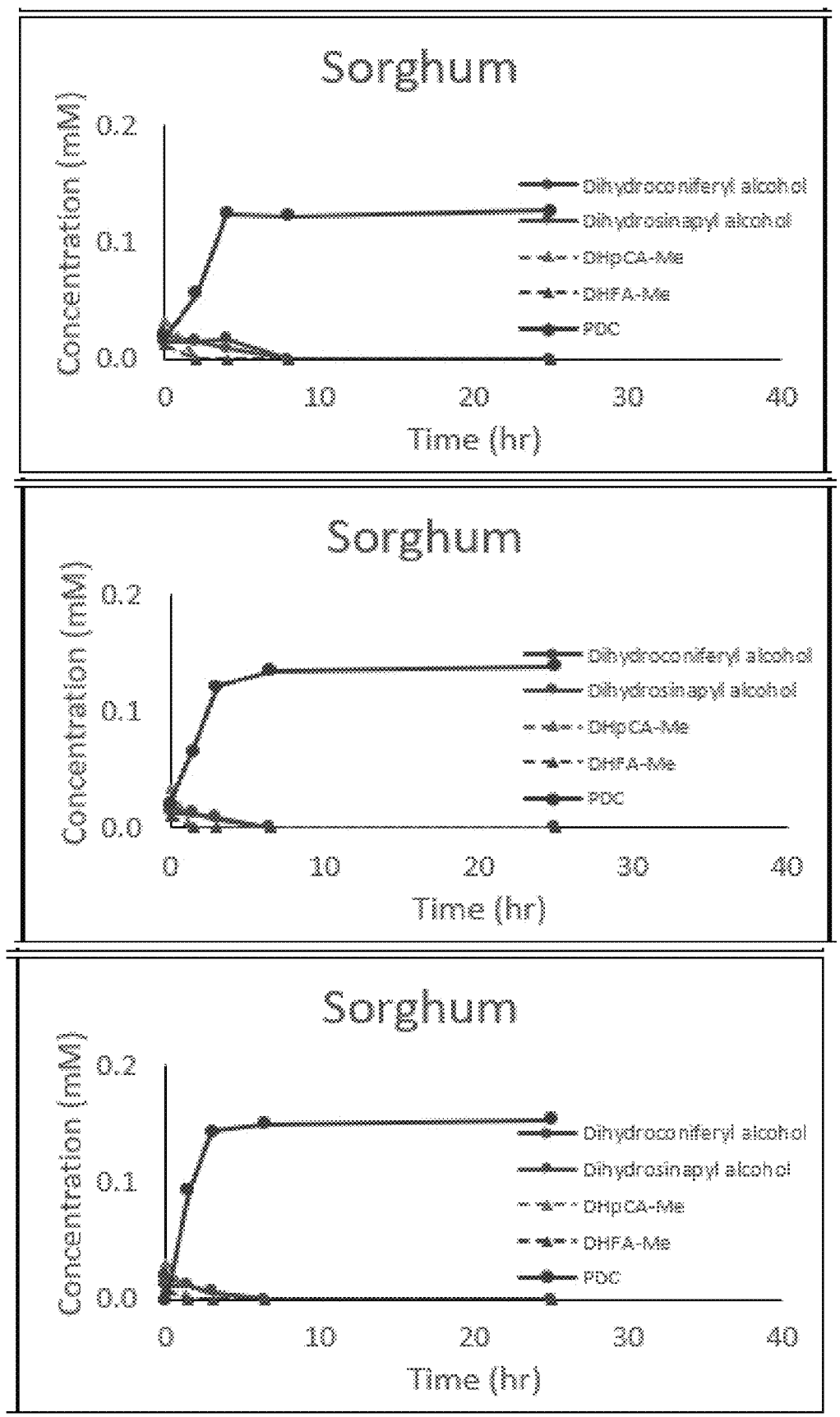
Figure 16D:
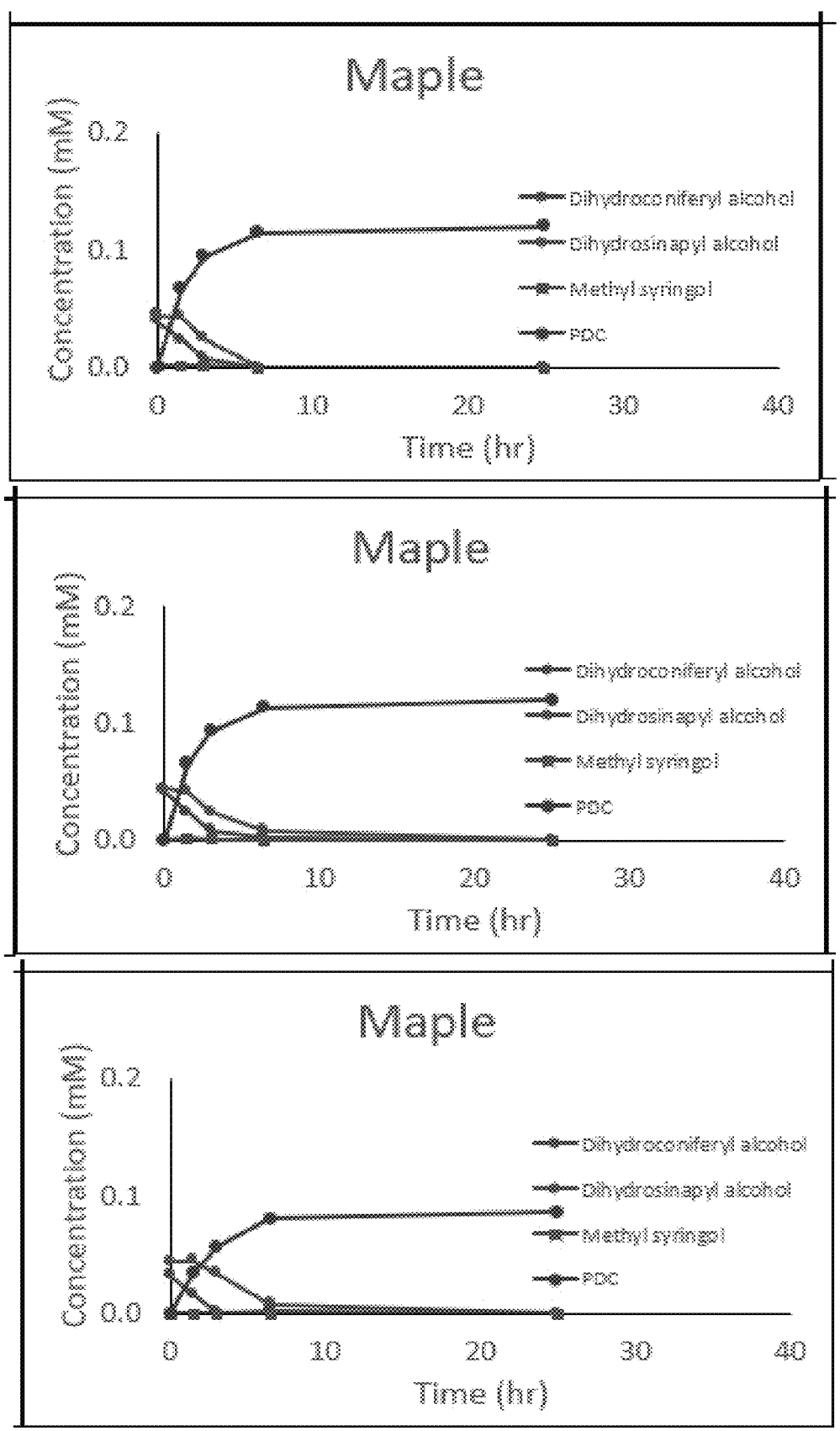
Figure 17A:
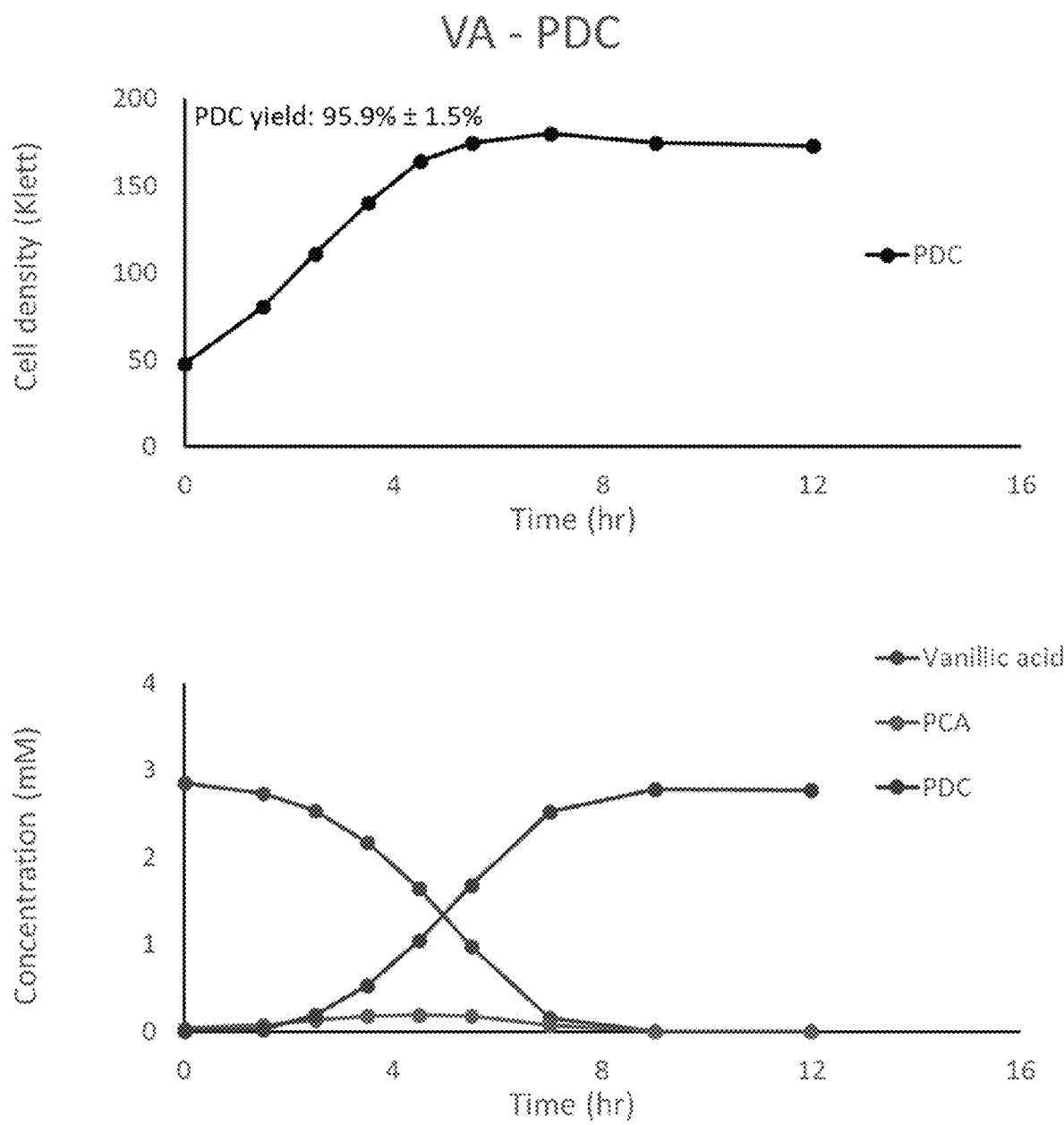
FIGS. 17A-17H. Cell growth and production of PDC from vanillic acid ("VA") with the N. aromaticivorans 12444ΔligIΔdesCD strain (labeled as the "PDC" strain) (FIG. 17A) and variants comprising additional deletions (FIGS. 17B-17H). The additional deletions include ΔligM (ΔSaro_2861) (FIG. 17B), ΔdesA (ΔSaro_2404) (FIG. 17C), ΔvanA (ΔSaro_1872) (FIG. 17D), ΔligMΔdesA (ΔSaro_2861ΔSaro_2404) (FIG. 17E), ΔligMΔvanA (ΔSaro_2861ΔSaro_1872) (FIG. 17F), ΔdesAΔvanA (ΔSaro_2404ΔSaro_1872) (FIG. 17G), and ΔligMΔdesAΔvanA (ΔSaro_2861ΔSaro_2404ΔSaro_1872) (FIG. 17H).
Figure 17B:
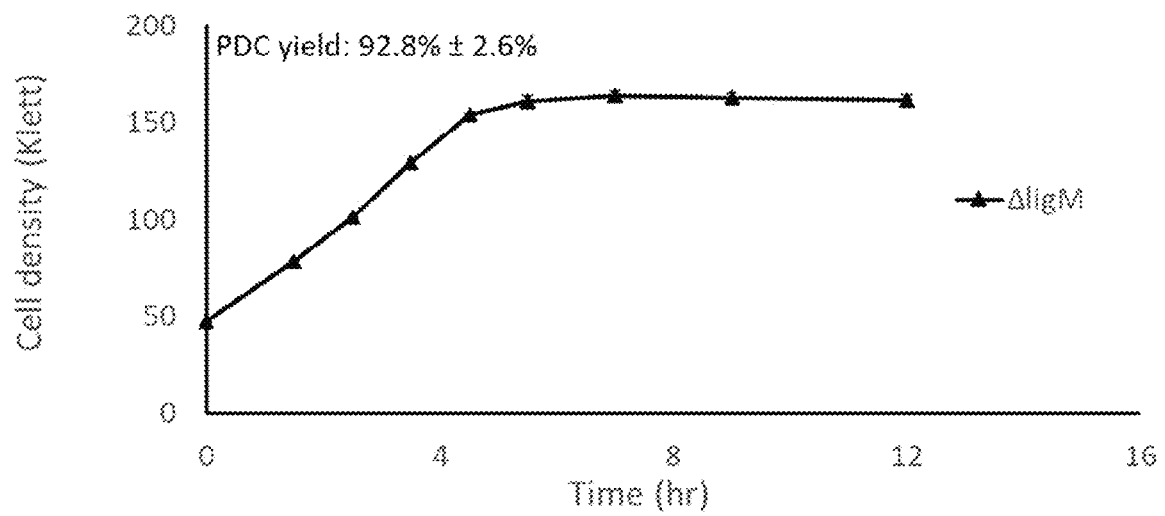
Figure 17B:
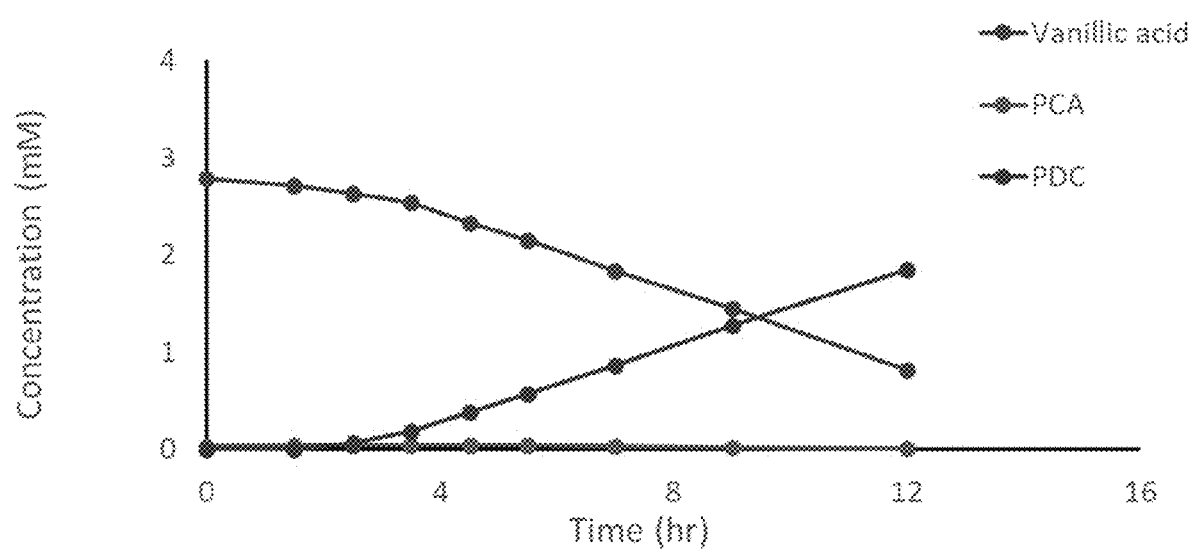
Figure 17C:
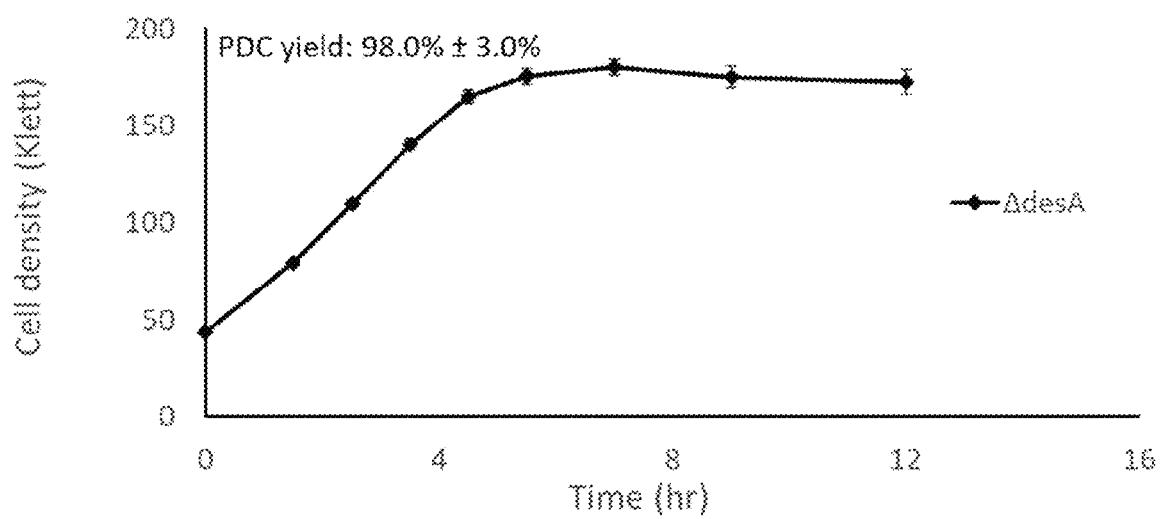
Figure 17C:
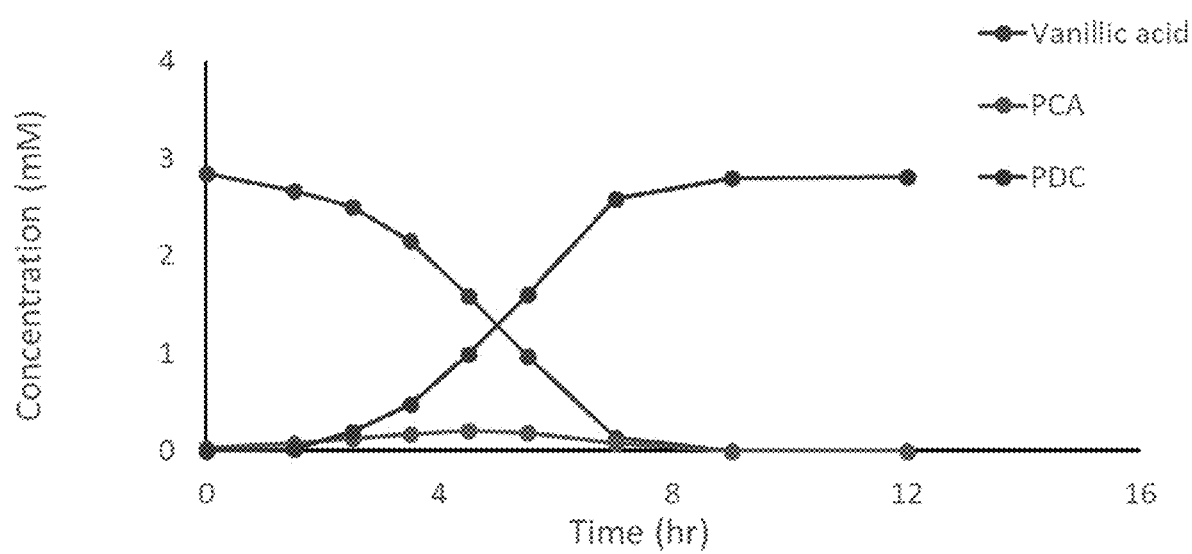
Figure 17D:
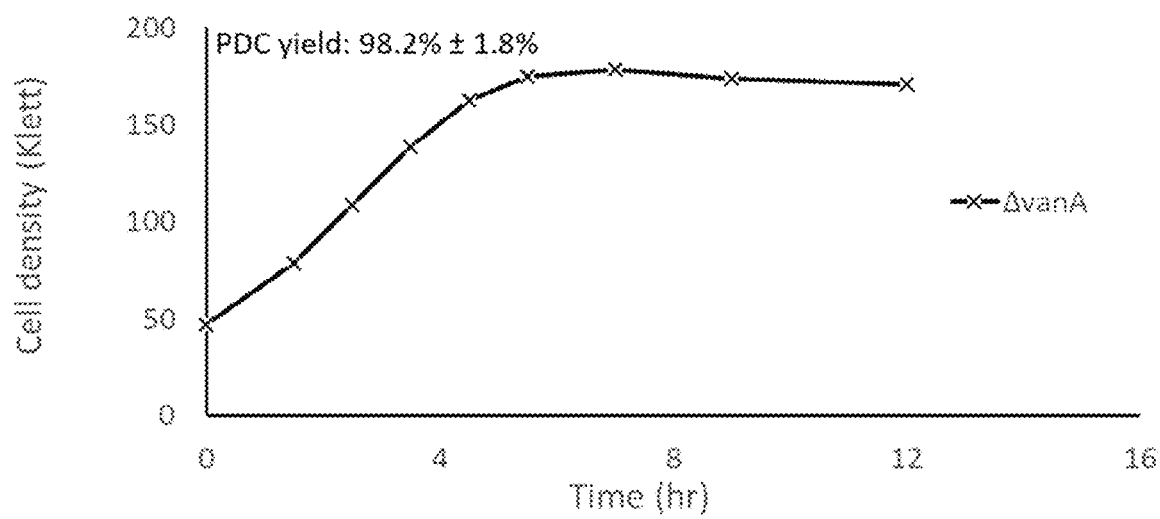
Figure 17D:
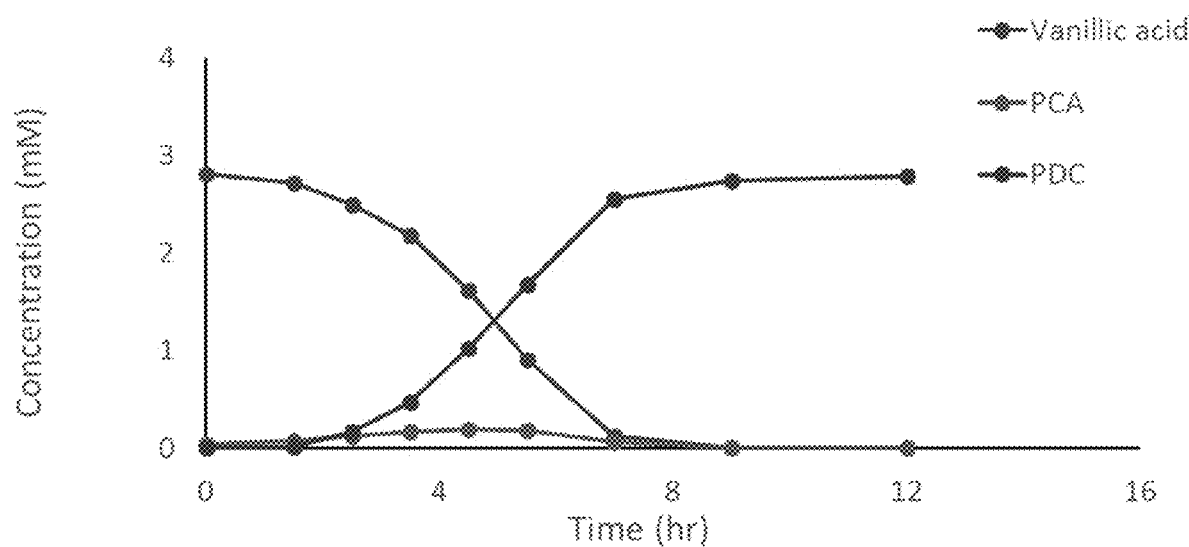
Figure 17E:
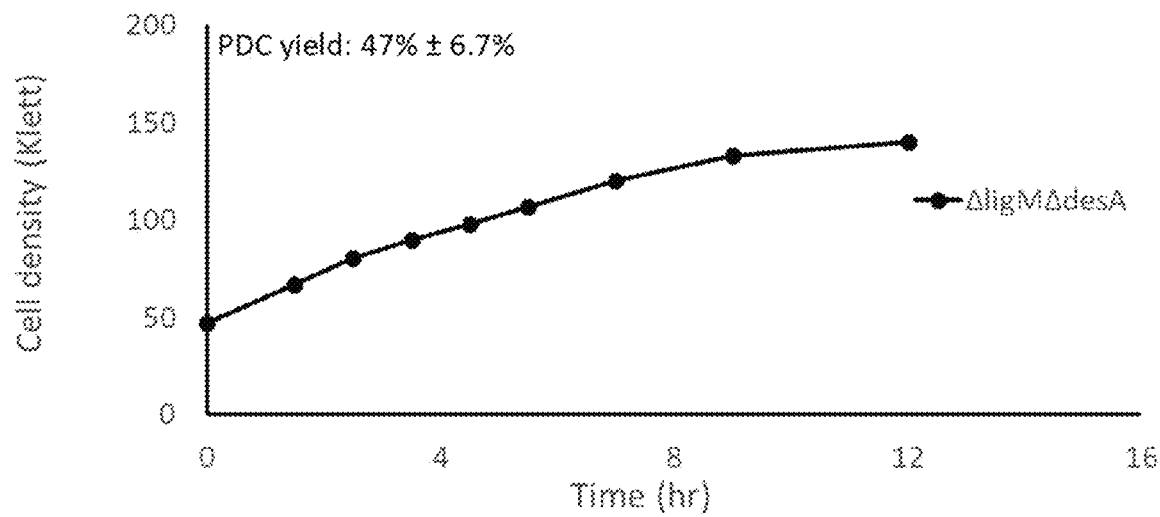
Figure 17E:
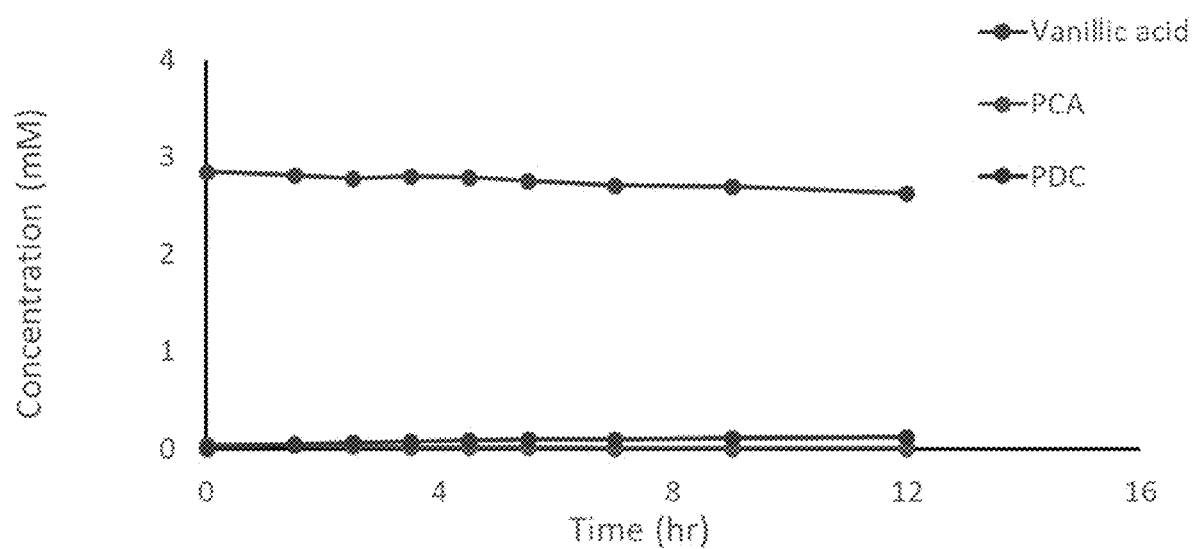
Figure 17F:
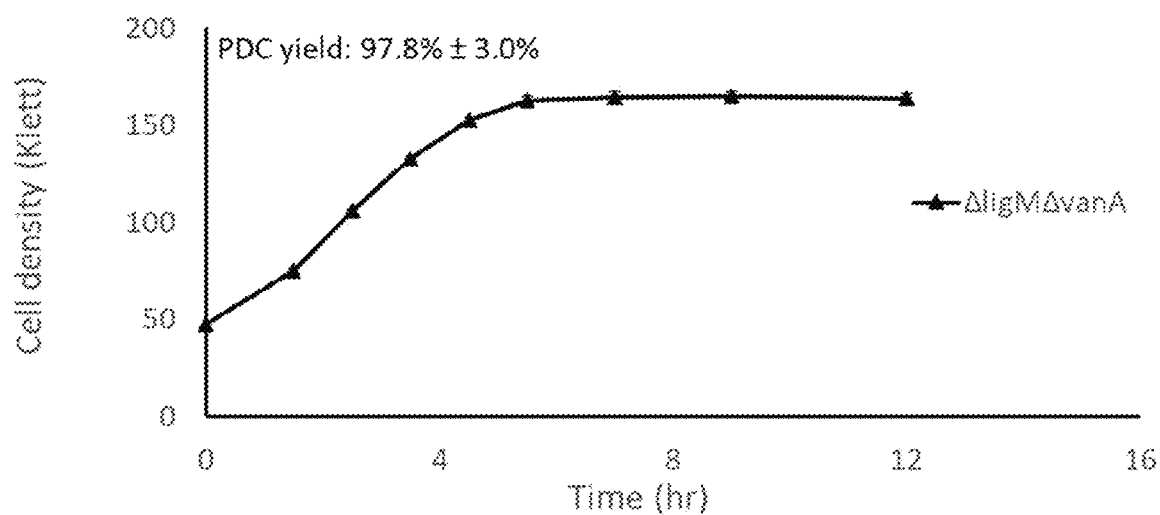
Figure 17F:
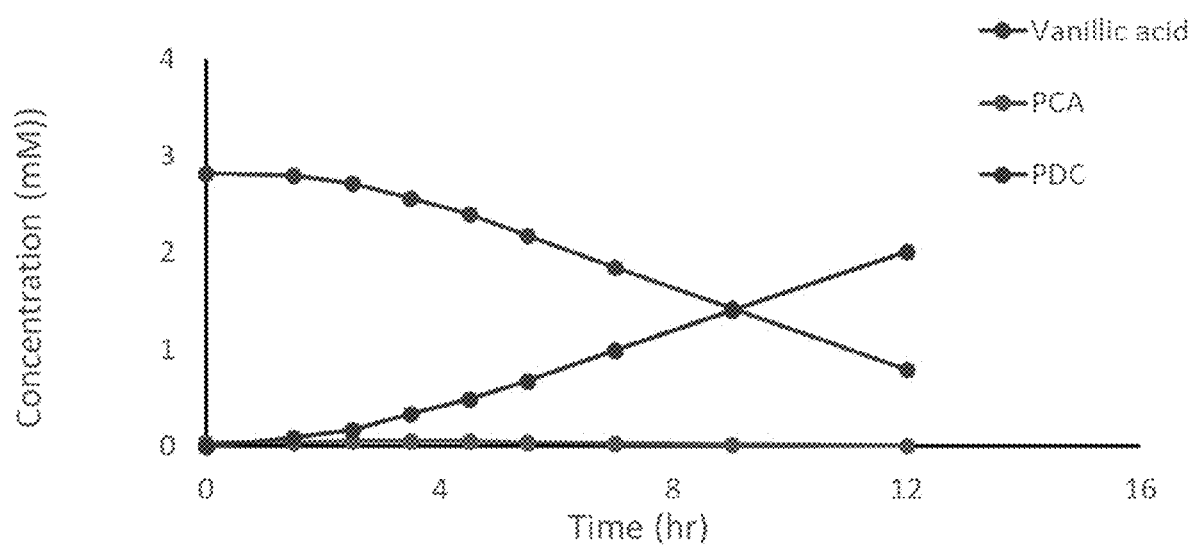
Figure 17G:
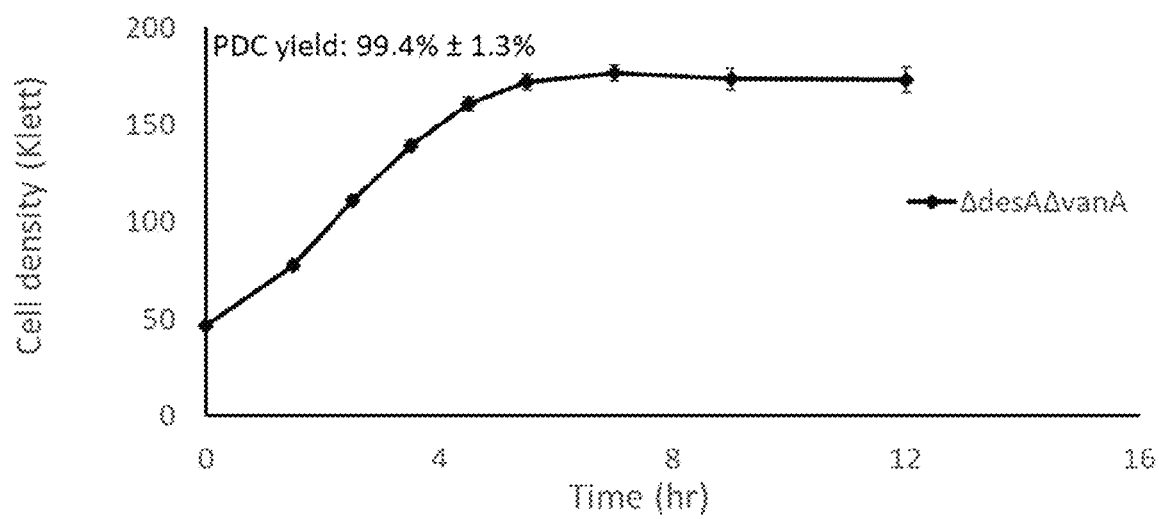
Figure 17G:
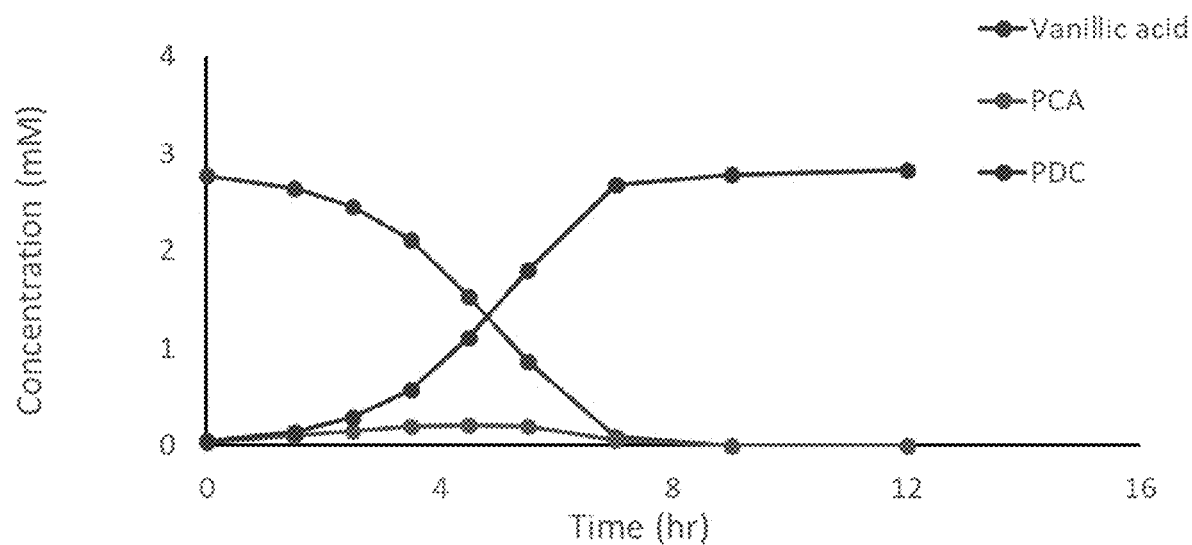
Figure 17H:
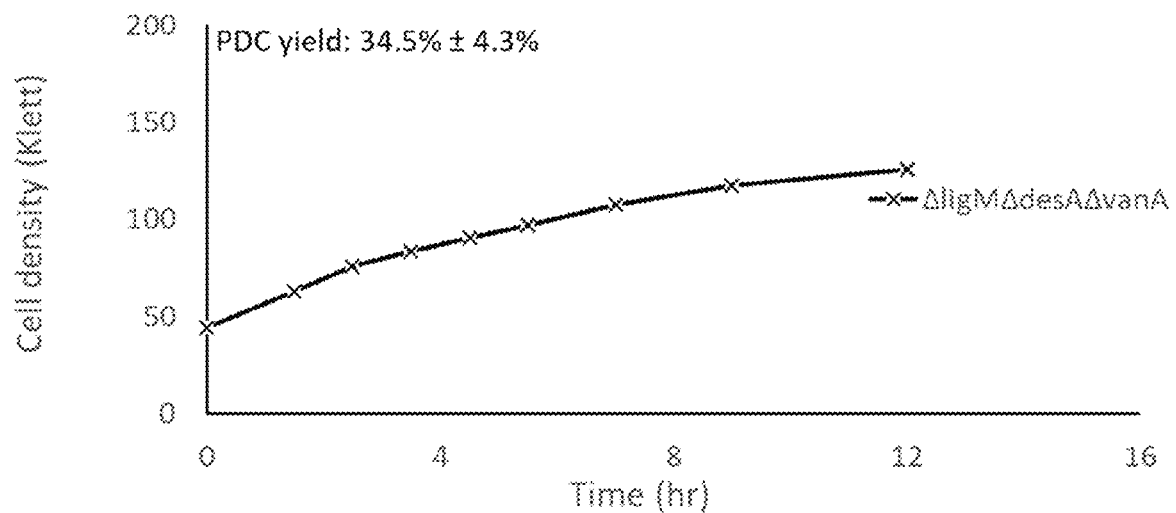
Figure 17H:
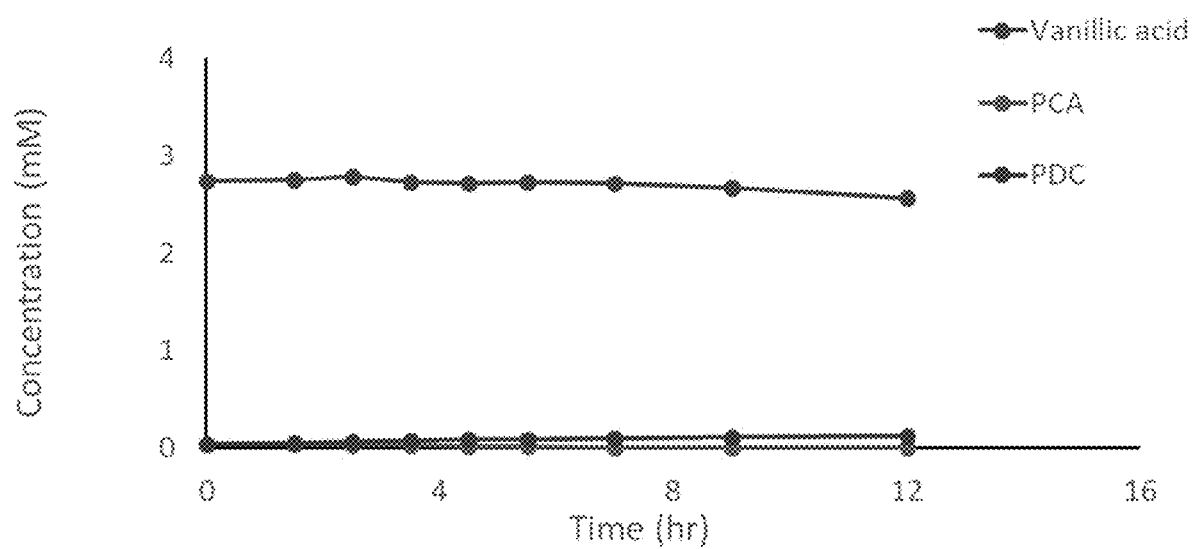
Figure 18A:
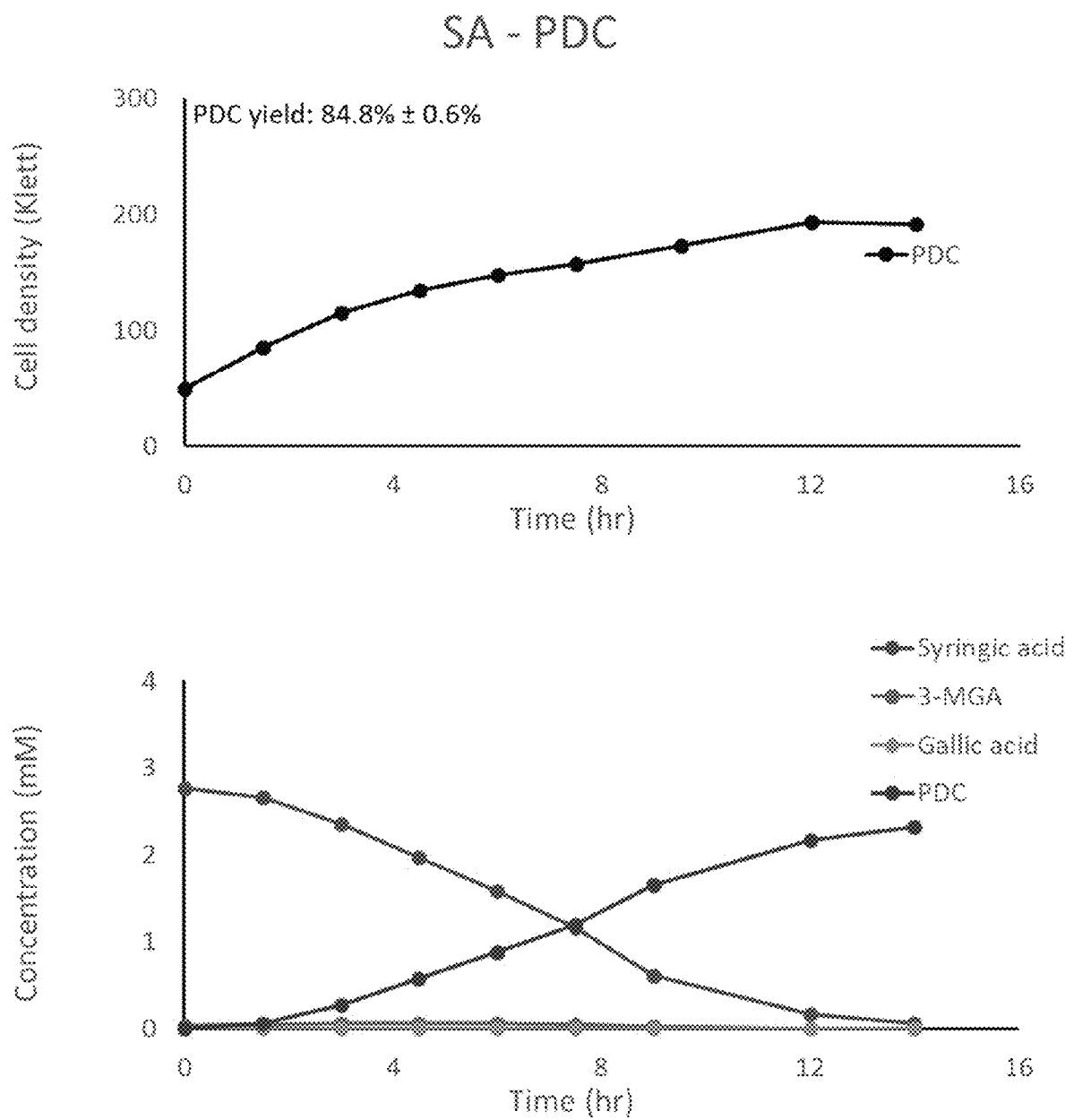
FIGS. 18A-18H. Cell growth and production of PDC from syringic acid ("SA") with the N. aromaticivorans 12444ΔligIΔdesCD strain (labeled as the "PDC" strain) (FIG. 18A) and variants comprising additional deletions (FIGS. 18B-18H). The additional deletions include ΔligM (ΔSaro_2861) (FIG. 18B), ΔdesA (ΔSaro_2404) (FIG. 18C), ΔvanA (ΔSaro_1872) (FIG. 18D), ΔligMΔdesA (ΔSaro_2861ΔSaro_2404) (FIG. 18E), ΔligMΔvanA (ΔSaro_2861ΔSaro_1872) (FIG. 18F), ΔdesAΔvanA (ΔSaro_2404ΔSaro_1872) (FIG. 18G), and ΔligMΔdesAΔvanA (ΔSaro_2861ΔSaro_2404ΔSaro_1872) (FIG. 18H).
Figure 18B:
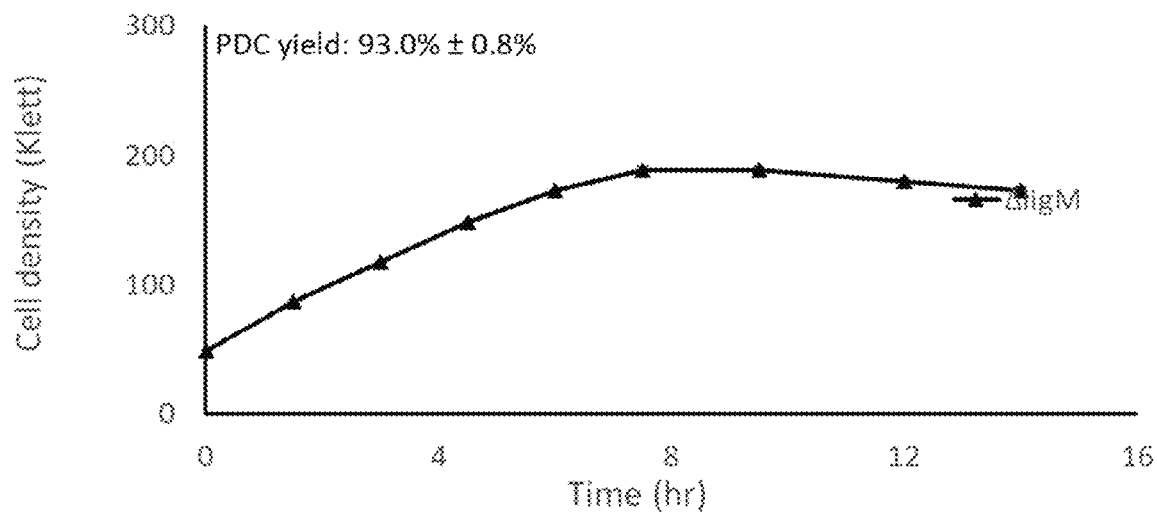
Figure 18B:
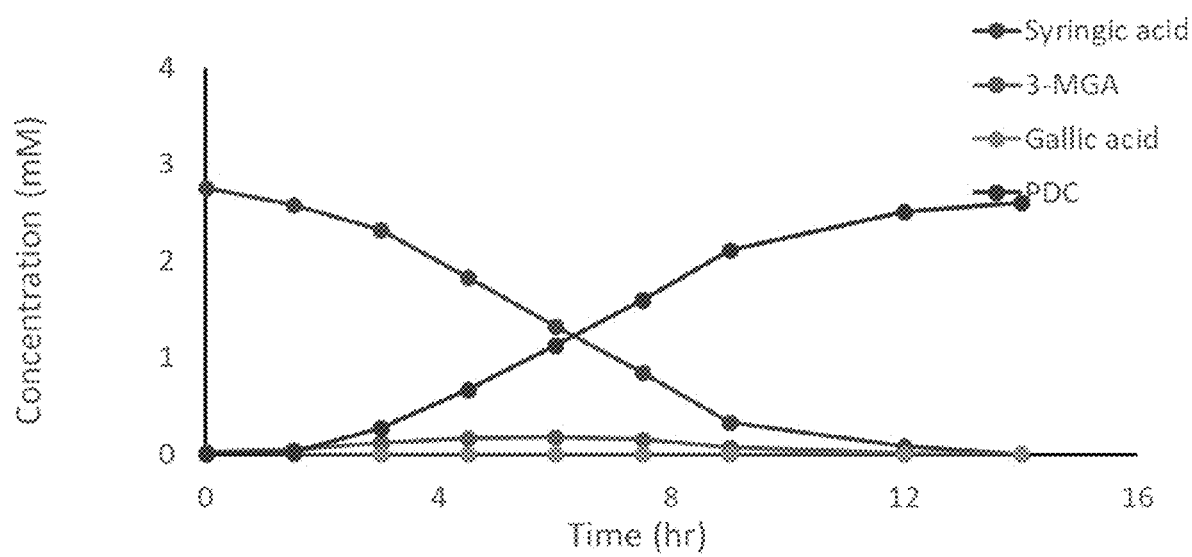
Figure 18C:
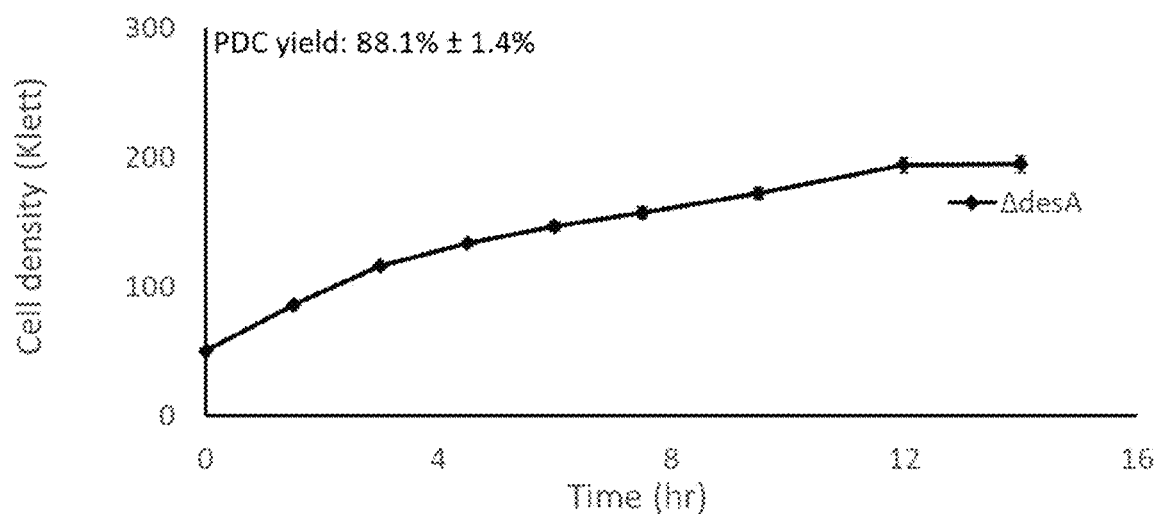
Figure 18C:
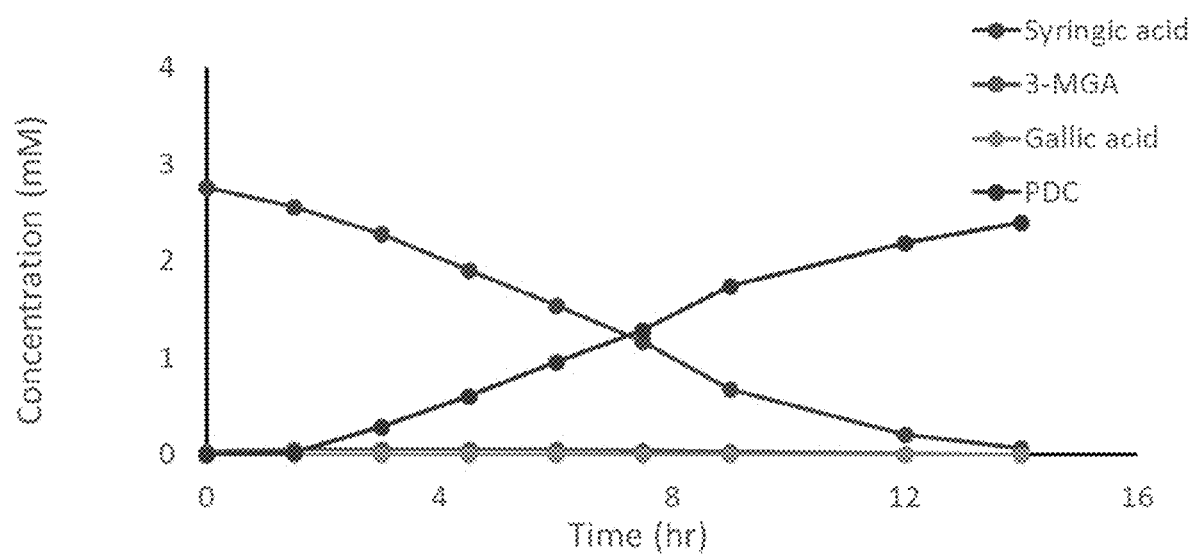
Figure 18D:
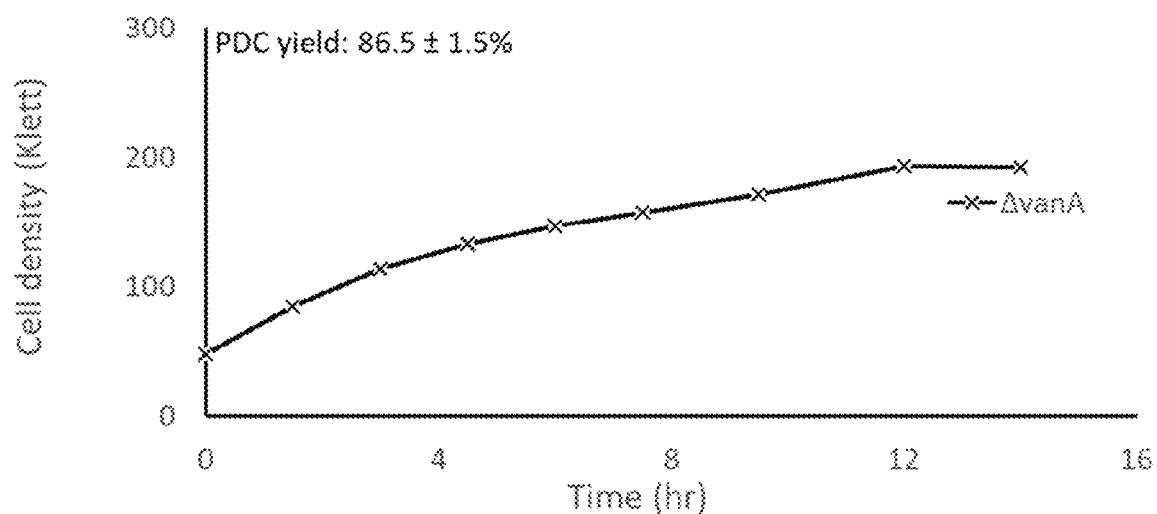
Figure 18D:
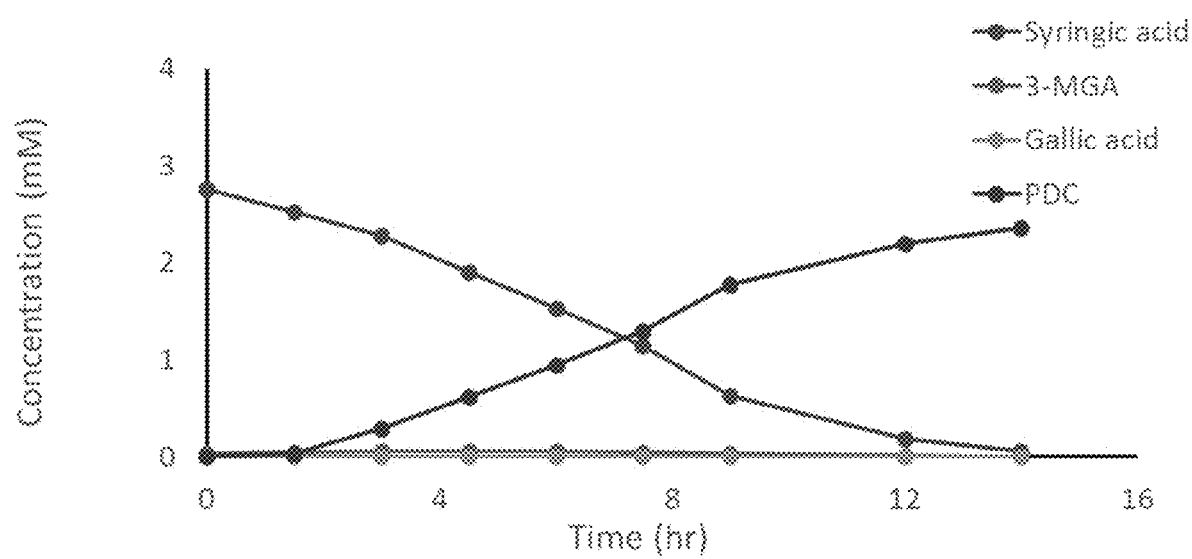
Figure 18E:
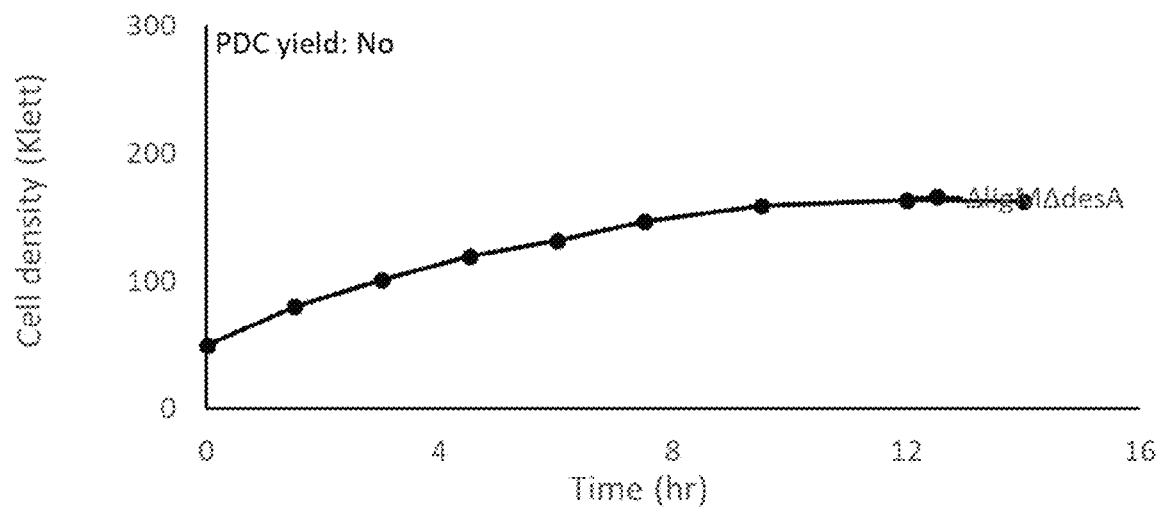
Figure 18E:
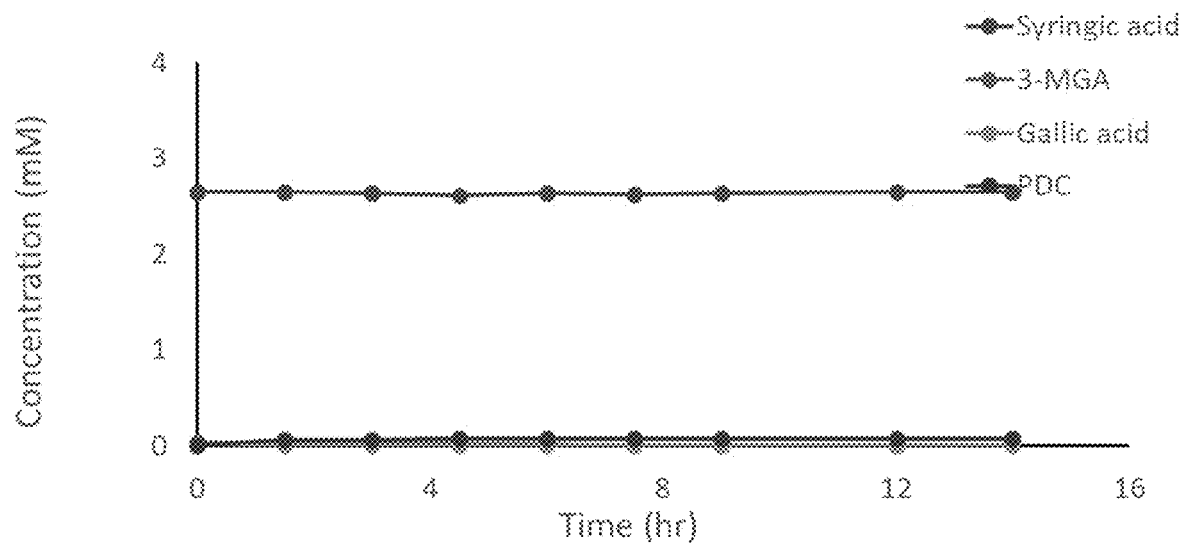
Figure 18F:
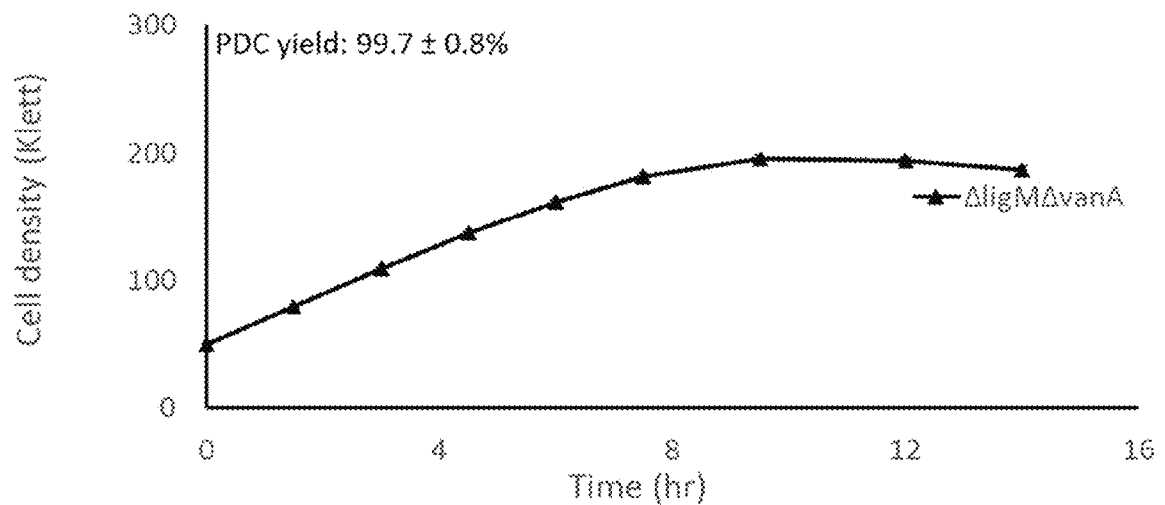
Figure 18F:
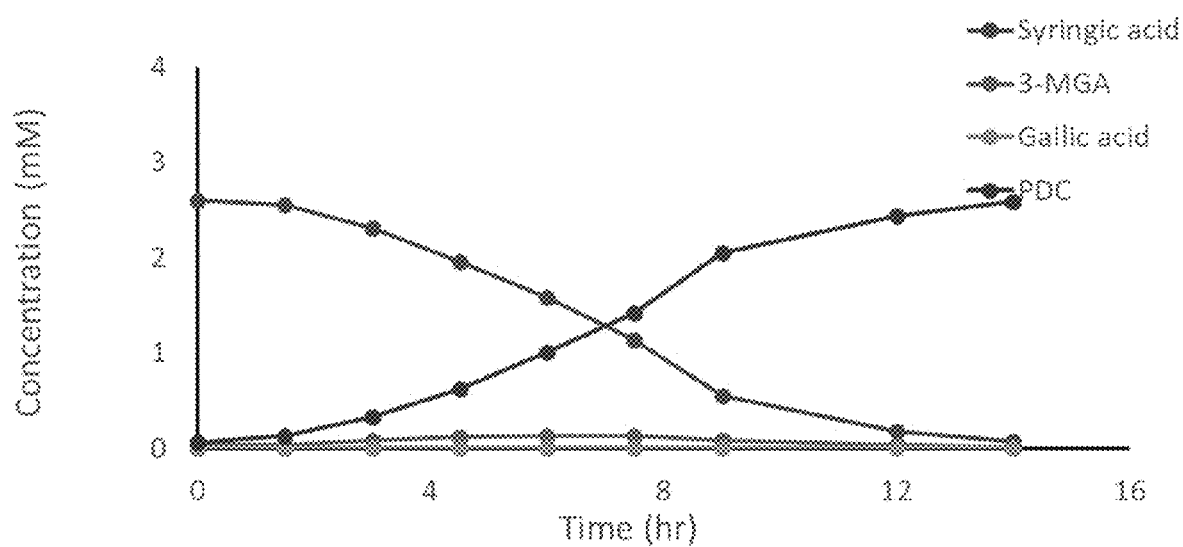
Figure 18G:
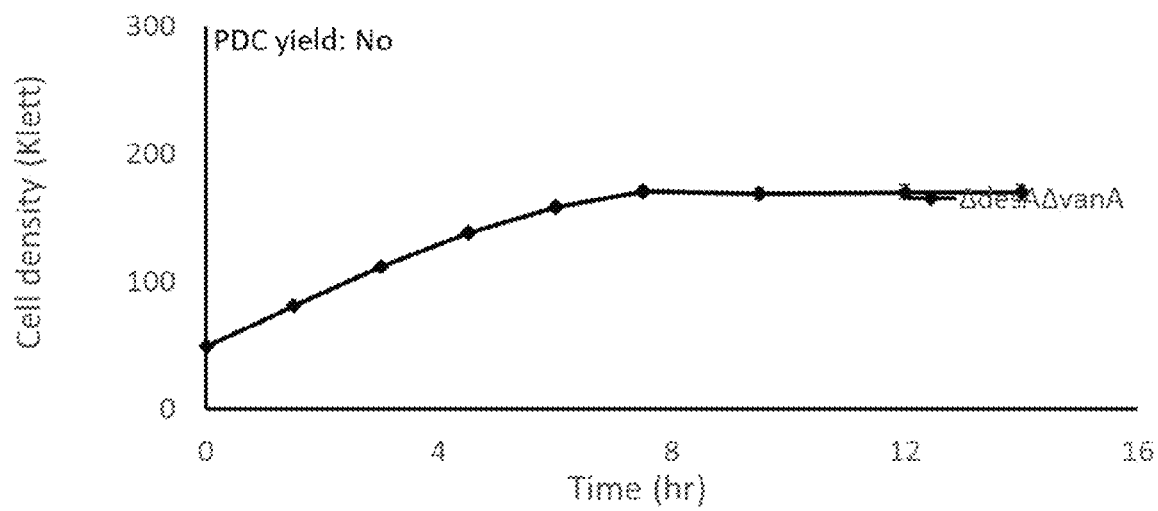
Figure 18G:
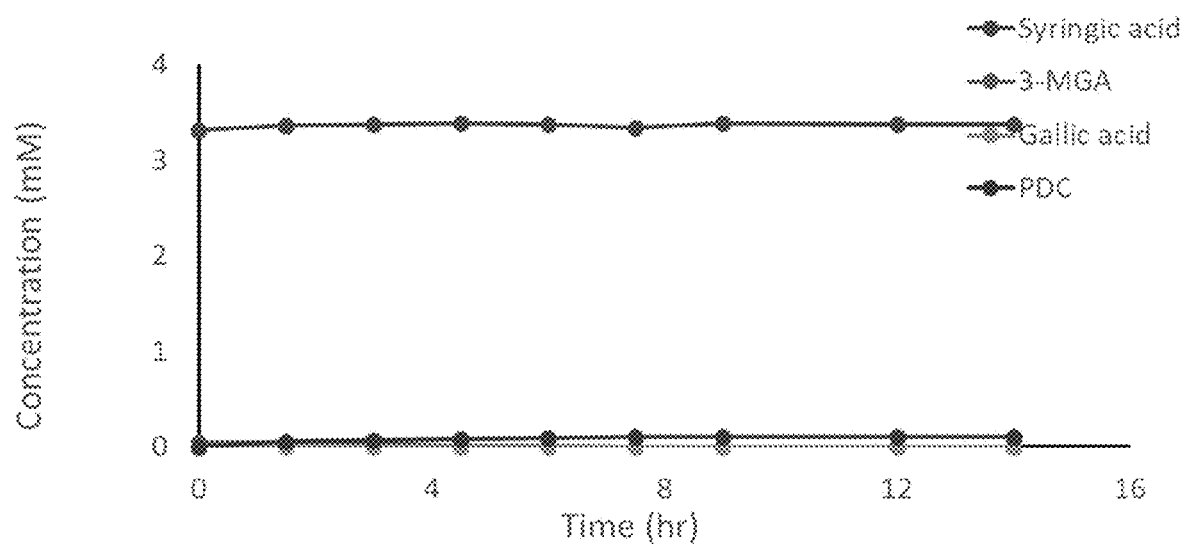
Figure 18H:
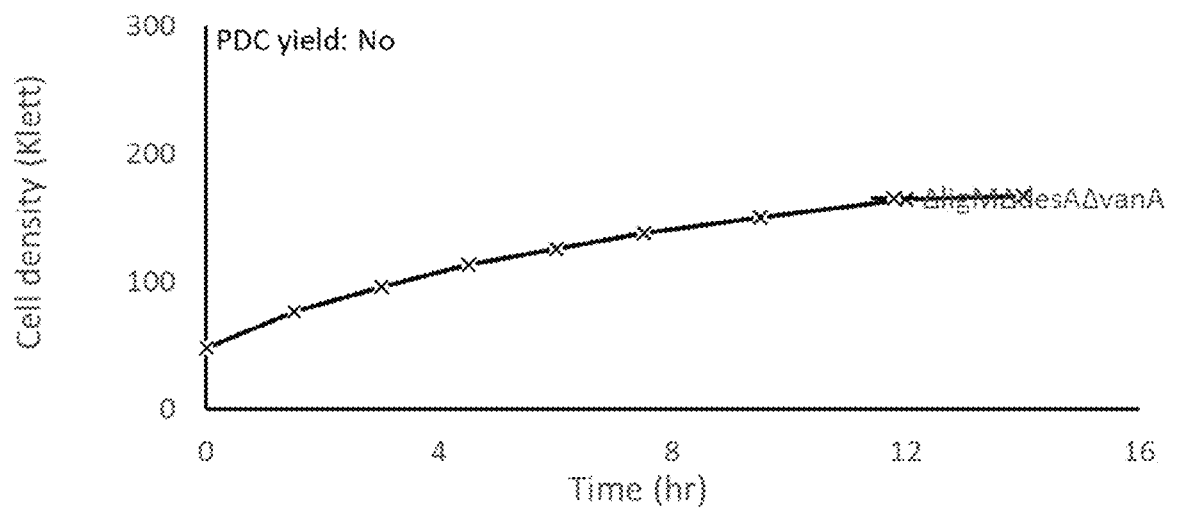
Figure 18H:
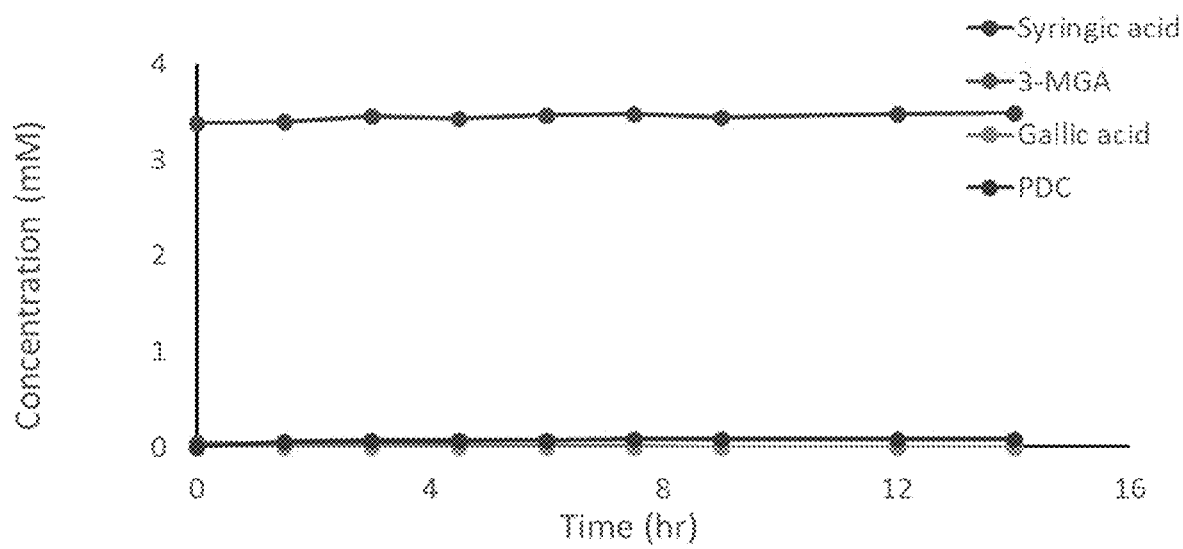

To determine the feasibility of producing PDC from lignin isolated from lignocellulosic biomass via γ-valerolactone (GVL) pretreatment and subsequently subjected to hydrogenolysis, production of PDC from isolated compounds found in such preparations was tested with the *N. aromaticivorans* 12444ΔligIΔdesCD strain. PDC was produced from many of these compounds (FIGS. 15A-15C), including methyl guaiacol (FIG. 15A), propyl guaiacol (FIG. 15A), dihydroconiferyl alcohol (FIG. 15A), methyl syringol (FIG. 15B), p-hydroxy benzoic acid methyl ester (FIG. 15B), dihydrop-hydroxy cinnamic acid methyl ester (FIG. 15B), dihydrosyringol alcohol (FIG. 15C), and dihydroferulic acid methyl ester (FIG. 15C).

In light of the high proportion of compounds capable of serving as PDC precursors, production of PDC from poplar (FIG. 16A), switchgrass (FIG. 16B), sorghum (FIG. 16C), and maple (FIG. 16D) lignin isolated from lignocellulosic biomass via γ-valerolactone (GVL) pretreatment and subjected to hydrogenolysis[48] was tested using the *N. aromaticivorans* 12444ΔligIΔdesCD strain. High amounts of PDC was produced in each case (FIGS. 16A-16D).

These results show that the *N. aromaticivorans* 12444ΔligIΔdesCD strain is capable of producing PDC from lignocellulosic biomass derived from various sources, pretreatments, and processing methods.

Additional Mutations to the *N. aromaticivorans* 12444ΔligIΔdesCD Strain

The effects of additional mutations to the *N. aromaticivorans* 12444ΔligIΔdesCD strain on PDC production were tested. The additional mutations included deletions of ligM (Saro_2861), desA (Saro_2404), vanA (Saro_1872), and combinations thereof. LigM (produced from ligM) and VanA (produced from vanA) are each vanillate/3-O-methylgallate O-demethylases. DesA (produced from desA) is a syringic acid O-demethylase. The parent 12444ΔligIΔdesCD strain and the variants thereof were tested for PDC production from vanillic acid (FIGS. 17A-17H) and syringic acid (FIGS. 18A-18H) as substrates.

Deletion of each ligM (FIG. 18B), and desA (FIG. 18C), individually in the 12444ΔligIΔdesCD strain increased PDC yields from syringic acid. Deletion of vanA (FIG. 18D) in the 12444ΔligIΔdesCD strain had no significant effect on PDC yield from syringic acid. Deletion of ligM in combination with vanA (FIG. 18F) in the 12444ΔligIΔdesCD strain increased the PDC yield from syringic acid to near stoichiometric conversion. Deletion of ligM in combination with desA (FIG. 18E), desA in combination with vanA (FIG. 18G), or ligM in combination with desA and vanA (FIG. 18H) ablated the production of PDC from syringic acid. Deletion of ligM (FIG. 17B), desA (FIG. 17C), or vanA (FIG. 17D) individually, or deletion of vanA in combination with ligM (FIG. 17F) or desA (FIG. 17G) in the 12444ΔligIΔdesCD strain had no significant effect on PDC production from vanillic acid. However, deletion of ligM in combination with desA (FIG. 17E) or deletion of ligM in combination with desA and vanA (FIG. 17H) in the 12444ΔligIΔdesCD strain decreased the production of PDC from vanillic acid.

Figure 19:
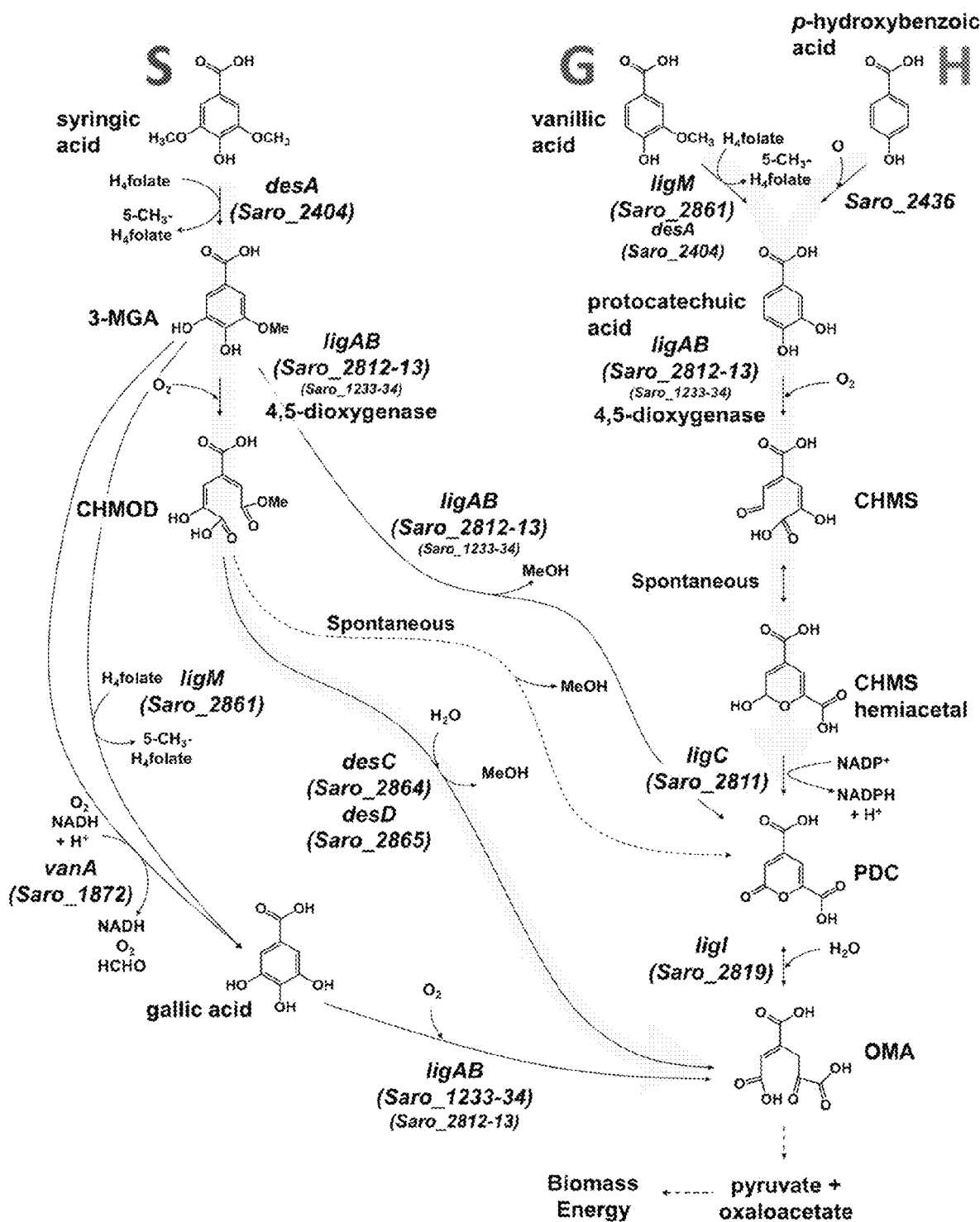
FIG. 19. Predicted pathways in addition to those shown in FIG. 1 of S unit (syringic acid), G unit (vanillic acid), and H unit (p-hydroxybenzoic acid) metabolism in N. aromaticivorans DSM12444.

The results outlined above suggest that DesA reacts with syringic acid as a substrate and likely also reacts with vanillic acid as a substrate, that LigM reacts with vanillic acid and 3-MGA as substrates and likely also reacts with syringic acid as a substrate, and that vanA may react with 3-MGA as a substrate. A revised model of the pathways leading to production of PDC from S units (syringic acid), G units (vanillic acid), and H units (p-hydroxybenzoic acid) based on the results outlined above is provided in FIG. 19.

Discussion

The economic and environmental viability of producing fuels and chemicals from lignocellulose is tightly connected to the efficiency of its utilization. New methods are needed to efficiently utilize the recalcitrant aromatic fractions, such as lignin.[31] Multiple chemical approaches have shown promising results for breaking down the complex lignin polymer into small molecule aromatic units.[6,7] However, the heterogeneous nature of the depolymerization products obtained pose challenges for further upgrading to valuable products.[32] One successful strategy to address the chemical heterogeneity is to funnel the mixture of compounds through convergent aromatic biodegradation pathways into one valuable product by interruption and/or redirection of the metabolic flow to a pathway intermediate.[19,22,23] These studies suggest that a mixed approach that integrates chemical and biological tools has the potential to be an effective strategy to maximize the yield of desired products from lignin transformation. Some of the major challenges in biological funneling are the transformation of unnatural products resulting from chemical depolymerization for which microbial metabolic capabilities are unknown, the maximization of target product yield while minimizing the accumulation of undesired intermediates or end products, and the identification of industrially useful target molecules that could most readily be produced from lignin components via known metabolic pathways.[15]

The present study addresses each of these issues using mutant strains of *N. aromaticivorans* DSM12444, a microbe naturally capable of degrading S, G, and H type aromatic compounds, as a well as lignin derived aromatic dimers.[25,33] We chose *N. aromaticivorans* DSM12444 due to its known or predicted ability to grow in the presence of multiple aromatic compounds, its suitability for genetic analysis and modification, its ability to co-metabolize aromatics in the presence of other organic compounds (such as sugars, which are another plentiful product of plant biomass degradation), the lack of toxicity of PDC to this organism, and the potential to produce single valuable products using defined mutants.

The efficiency of carbon recovery in valuable compounds depends on factors such as the target product, the minimization of undesired metabolic byproducts, and number or amount of substrates being metabolized by the bacterium. Products derived from metabolic intermediates in the upper aromatic catabolic pathways of bacteria like *N. aromaticivorans* DSM12444 should yield higher carbon recovery than products derived from lower pathways, where more carbon may have already been lost during degradation. We selected PDC as the target product for this study because, in addition to its proven potential as a polyester precursor,[26] it is the earliest compound in which the degradation pathways for S, G, and H aromatic compounds were predicted to converge in defined *N. aromaticivorans* mutants (FIG. 1).

The observation of PDC accumulation when strain 12444Δ1879 was grown on syringic acid (28%; FIG. 5 panel C) was surprising, since we had predicted that the majority of the syringic acid would follow the 3-MGA, CHMOD, OMA pathway (FIG. 1) when the pathway was not altered by mutation. Furthermore, we had predicted that any PDC formed during syringic acid degradation in this strain would be oxidized by LigI to OMA (FIG. 1). The sequential increase in PDC yield in strains 12444ΔdesCD (49%; FIG. 6 panel E) and 12444ΔligIΔdesCD (66%; FIG. 6 panel F) confirms the participation of DesC, DesD, and LigI in the degradation of S type aromatics in *N. aromaticivorans* and suggests that a large fraction of the syringic acid is naturally channeled through PDC. Since PDC does not accumulate in 12444Δ1879 cultures grown on the products from chemically depolymerized lignin (FIG. 9 panel D) we offer two alternative hypotheses that would need to be tested in the future. First, it is possible that G or H substrates regulate expression of LigI in *N. aromaticivorans*. Thus, LigI would be poorly or not expressed when S type aromatics are the sole carbon source, allowing for some PDC accumulation by strain 12444Δ1879 grown on syringic acid. On the other hand, LigI would be expressed when 12444Δ1879 is grown on the mixtures of S, G, and H aromatics present in depolymerized lignin, preventing PDC accumulation. Alternatively, since it is not known whether CHMOD transformation to PDC is abiotic or enzymatic, it may be possible that CHMOD is secreted into the growth media where it undergoes spontaneous cyclization, resulting in extracellular PDC accumulation. Higher PDC yields by 12444ΔdesCD and 12444ΔligIΔdesCD could then be explained by increased CHMOD secretion when the aromatic degradation pathways are blocked.

We observe nearly stoichiometric conversion of vanillin and G-diketone into PDC, without extracellular accumulation of other aromatics. However, conversion of p-coumaric acid, p-hydroxybenzaldehyde, p-hydroxybenzoic acid, ferulic acid, vanillic acid, syringaldehyde, syringic acid, and S-diketone to PDC was found to have somewhat lower efficiencies (Table 4). The non-stoichiometric conversion of these aromatic compounds into PDC by *N. aromaticivorans* is not due to accumulation of intermediate metabolites such as syringic acid, vanillic acid, p-hydroxybenzoic acid and protocatechuic acid, since they only accumulated transiently. Instead, the lower conversion efficiencies could potentially be explained by the presence of alternative, less efficient, and poorly studied pathways for the degradation of those compounds. For instance, the *N. aromaticivorans* genome contains multiple genes annotated as aromatic ring cleavage dioxygenases for which specificity has not yet been established.[34] The presence of a catechol degradation pathway in *N. aromaticivorans* that uses 2,3-cleavage of the aromatic ring has been suggested as a possible alternative pathway for protocatechuic acid degradation.[2] Such alternative non-specific reaction of a catechol dioxygenase could explain the observed lower efficiencies in the transformation of some G and H aromatics to PDC. This hypothesis is supported by the increased cell density observed in cultures of strain 12444ΔligIΔdesCD grown in media containing glucose plus protocatechuic acid compared to cultures only fed glucose (Table 5). Another enzyme with low substrate specificity appears to be the O-demethylase LigM, included in our model as catalyzing the demethylation of vanillic acid (FIG. 1). In *Sphingobium* sp. SYK-6, LigM is also predicted to catalyze O-demethylation of 3-MGA to gallate,[1] which is then proposed to be oxidized to OMA by either LigAB, a dioxygenase with broad specificity (FIG. 1), or DesB, an enzyme not present in *N. aromaticivorans*. Although this route for degradation of S aromatics is not predicted to be important in *N. aromaticivorans*,[2] LigM activity with 3-MGA and LigAB activity with gallate could contribute to lowering the efficiency of PDC formation from S aromatics by bypassing the blockage in S aromatic degradation intended with the desCD mutation. These consideration are solved with the experiments deleting the vanillate/3-O-methylgallate O-demethylases outlined above. Thus, future identification and analysis of additional pathways involved in aromatic metabolism by *N. aromaticivorans* DSM12444 could provide useful information for further increasing the yield of PDC or other target chemicals by preventing aromatic substrates from being degraded by alternative routes.

Fed-batch experiments in a pH-controlled bioreactor showed an increase of up to 8.7 times in PDC titers with respect to titers obtained in batch experiments. These results show a promising potential for production of PDC from aromatic compounds. However, in this experiment, a progressive accumulation of aromatic substrates and glucose was observed. Additional research will be necessary to optimize culture conditions.

The efficiency of lignin conversion to a desired product is also impacted by the nature of the aromatic compounds that result from chemical lignin depolymerization, which may be different from natural products of environmental lignin depolymerization. Therefore, the existence of microbial pathways to metabolize these products could be crucial to increase product recovery. For example, formic-acid-induced depolymerization of oxidized lignin produces a high proportion of aromatic diketones,[4] compounds that have also been reported to be present in lignocellulose dilute acid hydrolysates.[35] Biological sources of these or structurally related compounds have not been reported, so it was previously unknown whether N. aromaticivorans DSM12444 could metabolize these products or convert them into PDC or other valuable materials. In this study, we found that N. aromaticivorans can convert both S- and G-type diketones into PDC, indicating that they are also degraded via the predicted aromatic degradation pathways (FIG. 1). However, the upper pathway enzymes that transform the diketones to known intermediates in the aromatic degradation pathways remain unknown.

Finally, chemically depolymerized lignin yields a variety of higher molecular weight lignin derived products in addition to monomeric units.[4] Sphingomonad bacteria, such as N. aromaticivorans DSM12444, are known or predicted to be capable of breaking most of the linkages found between aromatic subunits in natural lignin in defined ways that yield predictable mono-aromatic products that can be further metabolized.[1,36] N. aromaticivorans, specifically, is known to be capable of degrading model aromatic dimers containing β-aryl-ether bonds[25] and its genome contains homologs of genes that code for the degradation of other aromatic dimers in Sphingobium sp. SYK-6.[1] This is an unexplored, but potentially important aspect of employing N. aromaticivorans as a platform microbe for valorization of mixtures of low molecular weight aromatic compounds generated from chemical depolymerization of lignin.

Aspects of the present examples are found in Perez et al.[46], which is incorporated herein by reference in its entirety.

CONCLUSIONS

A path to produce valuable products from the abundant and renewable raw material lignin is to integrate chemical and biological strategies to chemically depolymerize lignin into heterogeneous mixtures of compounds that are then funneled into a single valuable product using microbial catalysts. An ideal microbial catalyst would be capable of simultaneously converting aromatic compounds containing S, G, and H structures, including non-natural compounds generated by chemical depolymerization, into a single compound with high efficiency.

Here, we focused on the microbial production of PDC from aromatic products known to be generated by chemical methods of lignin depolymerization and direct, base-catalyzed release of aromatics from whole biomass. PDC has been shown to have potential as a precursor for polyesters and there is growing interest in using microbes to generate it from lignin.[21,22] However, the range of lignin-derived aromatic substrates that could be converted into PDC was limited.[21,22] This study expanded the range. Future improvement in PDC yields would require identification of alternative pathways that may be contributing to aromatic degradation. The information and strategies developed here with N. aromaticivorans DSM12444 can be implemented in other microbes.

REFERENCES

1. N. Kamimura, K. Takahashi, K. Mori, T. Araki, M. Fujita, Y. Higuchi and E. Masai, Environ. Microbiol. Rep., 2017, 9, 679-705.
2. J. H. Cecil, D. C. Garcia, R. J. Giannone and J. K. Michener, Appl. Environ. Microbiol., 2018, 84, 1-13.
3. J. Vogel, Curr. Opin. Plant Biol., 2008, 11, 301-307.
4. A. Rahimi, A. Ulbrich, J. J. Coon and S. S. Stahl, Nature, 2014, 515, 249-252.
5. H. Jørgensen, J. B. Kristensen and C. Felby, Biofuels, Bioprod Biorefin., 2007, 1(2), 119-134.
6. Z. Sun, B. Fridrich, A. de Santi, S. Elangovan and K. Barta, Chem. Rev., 2018, 118, 614-678.
7. W. Schutyser, T. Renders, S. Van den Bosch, S. F. Koelewijn, G. T. Beckham and B. F. Sels, Chem. Soc. Rev., 2018, 47, 852-908.
8. J. Ralph, G. Brunow and W. Boerjan, eLS, 2007.
9. P. J. Harris and R. D. Hartley, Nature, 1976, 259, 508.
10. P. J. Harris and R. D. Hartley, Biochem. Syst. Ecol., 1980, 8, 153-160.
11. D. C. C. Smith, Nature, 1955, 176, 267.
12. R. Vanholme, K. Morreel, C. Darrah, P. Oyarce, J. H. Grabber, J. Ralph and W. Boerjan, New Phytol., 2012, 196, 978-1000.
13. G. Fuchs, M. Boll and J. Heider, Nat. Rev. Microbiol., 2011, 9, 803-816.
14. T. D. Bugg, M. Ahmad, E. M. Hardiman and R. Rahmanpour, Nat. Prod. Rep., 2011, 28, 1883-1896.
15. G. T. Beckham, C. W. Johnson, E. M. Karp, D. Salvachua and D. R. Vardon, Curr. Opin. Biotechnol., 2016, 42, 40-53.
16. J. G. Linger, D. R. Vardon, M. T. Guarnieri, E. M. Karp, G. B. Hunsinger, M. A. Franden, C. W. Johnson, G. Chupka, T. J. Strathmann, P. T. Pienkos and G. T. Beckham, Proc. Natl. Acad Sci. U.S.A, 2014, 111, 12013-12018.
17. P. D. Sainsbury, E. M. Hardiman, M. Ahmad, H. Otani, N. Seghezzi, L. D. Eltis and T. D. H. Bugg, ACS Chem. Biol., 2013, 8, 2151-2156.
18. S. Austin, W. S. Kontur, A. Ulbrich, J. Z. Oshlag, W. Zhang, A. Higbee, Y. Zhang, J. J. Coon, D. B. Hodge, T. J. Donohue and D. R. Noguera, Environ. Sci. Technol., 2015, 49, 8914.
19. D. Vardon, M. A. Franden, C. Johnson, E. Karp, M. Guarnieri, J. Linger, M. Salm, T. Strathmann, G. Beckham and G. Ferguson, Energy Environ. Sci., 2015, 8, 617-628.
20. Y. Okamura-Abe, T. Abe, K. Nishimura, Y. Kawata, K. Sato-Izawa, Y. Otsuka, M. Nakamura, S. Kajita, E. Masai, T. Sonoki and Y. Katayama, J Biosci. Bioeng., 2016, 121, 652-658.
21. Y. Otsuka, M. Nakamura, K. Shigehara, K. Sugimura, E. Masai, S. Ohara and Y. Katayama, Appl. Microbiol. Biotechnol., 2006, 71, 608-614.
22. Y. Qian, Y. Otsuka, T. Sonoki, B. Mukhopadhyay, M. Nakamura, J. Jellison and B. Goodell, BioResources, 2016, 11, 6097-6109.
23. Z. Mycroft, M. Gomis, P. Mines, P. Law and T. D. H. Bugg, Green Chem., 2015, 17, 4974-4979.

24. J. K. Fredrickson, D. L. Balkwill, G. R. Drake, M. F. Romine, D. B. Ringelberg and D. C. White, *Appl. Environ. Microbiol.*, 1995, 61, 1917.
25. W. S. Kontur, C. A. Bingman, C. N. Olmsted, D. R. Wassarman, A. Ulbrich, D. L. Gall, R. W. Smith, L. M. Yusko, B. G. Fox, D. R. Noguera, J. J. Coon and T. J. Donohue, *J. Biol. Chem.*, 2018, 293, 4955-4968.
26. K. Shikinaka, Y. Otsuka, M. Nakamura, E. Masai and Y. Katayama, *J. Oleo Sci.*, 2018, 67, 1059-1070.
27. E. Masai, S. Shinohara, H. Hara, S. Nishikawa, Y. Katayama and M. Fukuda, *J. Bacteriol.*, 1999, 181, 55-62.
28. D. Kasai, E. Masai, K. Miyauchi, Y. Katayama and M. Fukuda, *J Bacteriol.*, 2004, 186, 4951-4959.
29. I. S. Sze and S. Dagley, *J. Bacteriol.*, 1987, 169, 3833-3835.
30. T. Michinobu, M. Hishida, M. Sato, Y. Katayama, E. Masai, M. Nakamura, Y. Otsuka, S. Ohara and K. Shigehara, *Polym. J.*, 2008, 40, 68-75.
31. A. J. Ragauskas, G. T. Beckham, M. J. Biddy, R. Chandra, F. Chen, M. F. Davis, B. H. Davison, R. A. Dixon, P. Gilna, M. Keller, P. Langan, A. K. Naskar, J. N. Saddler, T. J. Tschaplinski, G. A. Tuskan and C. E. Wyman, *Science*, 2014, 344, 1246843.
32. J. Zakzeski, P. C. A. Bruijnincx, A. L. Jongerius and B. M. Weckhuysen, *Chem. Rev.*, 2010, 110, 3552-3599.
33. D. L. Gall, J. Ralph, T. J. Donohue and D. R. Noguera, *Curr. Opin. Biotechnol.*, 2017, 45, 120-126.
34. V. D'Argenio, E. Notomista, M. Petrillo, P. Cantiello, V. Cafaro, V. Izzo, B. Naso, L. Cozzuto, L. Durante, L. Troncone, G. Paolella, F. Salvatore and A. Di Donato, *Acta Vet. Scand*, 2014, 15, 384.
35. V. D. Mitchell, C. M. Taylor and S. Bauer, *BioEnergy Res.*, 2014, 7, 654-669.
36. E. Masai, Y. Katayama and M. Fukuda, *Biosci., Biotechnol., Biochem.*, 2007, 71, 1-15.
37. A. Schäfer, A. Tauch, W. Jäger, J. Kalinowski, G. Thierbach and A. Pühler, *Gene*, 1994, 145, 69-73.
38. W. R. Sistrom, *J. Gen. Microbiol.*, 1962, 28, 607-616.
39. A. Bhalla, N. Bansal, R. Stoklosa, M. Fountain, J. Ralph, D. Hodge and E. Hegg, *Biotechnol. Biofuels*, 2016, 9, 34.
40. A. Das, A. Rahimi, A. Ulbrich, M. Alherech, A. H. Motagamwala, A. Bhalla, L. da Costa Sousa, V. Balan, J. A. Dumesic, E. L. Hegg, B. E. Dale, J. Ralph, J. J. Coon and S. S. Stahl, *ACS Sustainable Chem. Eng.*, 2018, 6, 3367-3374.
41. Z. Li, C. H. Chen, T. Liu, V. Mathrubootham, E. L. Hegg and D. B. Hodge, *Biotechnol. Bioeng.*, 2013, 110, 1078-1086.
42. T. Michinobu, M. Bito, Y. Yamada, Y. Katayama, K. Noguchi, E. Masai, M. Nakamura, S. Ohara and K. Shigehara, *Bull. Chem. Soc. Jpn.*, 2007, 80, 2436-2442.
43. D. Kasai, E. Masai, Y. Katayama and M. Fukuda, *FEMS Microbiol. Lett.*, 2007, 274, 323-328.
44. R. G. Taylor, D. C. Walker and R. R. McLnnes, *Nucleic Acids Res.*, 1993, 21, 1677-1678.
45. R. Simon, U. Priefer and A. Pühler, *Bio/Technology*, 1983, 1, 784.
46. Perez, Jose M. and Kontur, Wayne S. and Alherech, Manar and Coplien, Jason and Karlen, Steven D. and Stahl, Shannon S. and Donohue, Timothy J. and Noguera, Daniel R. Funneling aromatic products of chemically depolymerized lignin into 2-pyrone-4-6-dicarboxylic acid with *Novosphingobium aromaticivorans*. (2019) *Green Chemistry*. 21(6):1340-1350.
47. Karlen S D, Fasahati P, Mazaheri M, Serate J, Smith R A, Sirobhushanam S, Chen M, Tymkhin V I, Cass C L, Liu S, Padmakshan D, Xie D, Zhang Y, McGee M A, Russell J D, Coon J J, Kaeppler H F, de Leon N, Maravelias C T, Runge T M, Kaeppler S M, Sedbrook J C, Ralph J. Assessing the viability of recovering hydroxy-cinnamic acids from lignocellulosic biorefinery alkaline pretreatment waste streams. *ChemSusChem.* 2020 Jan. 26.
48. Wang H, Tucker M, Ji Y. Recent Development in Chemical Depolymerization of Lignin: A Review. (2013) *Journal of Applied Chemistry.* 2013:1-9.

What is claimed is:

1. A recombinant microorganism comprising modifications with respect to a corresponding native microorganism not comprising the modifications, wherein the recombinant microorganism is a bacterium capable of producing 2-pyrone-4,6-dicarboxylic acid, wherein the recombinant microorganism is *Novosphingobium aromaticivorans*, wherein the modifications comprise:
a first modification, wherein the first modification comprises a mutation of a native 2-pyrone-4,6-dicarboxylic acid (PDC) hydrolase gene present in the corresponding native microorganism, wherein the first modification reduces PDC hydrolase activity in the recombinant microorganism with respect to the corresponding native microorganism;
a second modification, wherein the second modification comprises a mutation of a native 4-carboxy-2-hydroxy-6-methoxy-6-oxohexa-2,4-dienoate (CHMOD) cis-trans isomerase gene present in the corresponding native microorganism, wherein the second modification reduces CHMOD cis-trans isomerase activity in the recombinant microorganism with respect to the corresponding native microorganism; and a third modification, wherein the third modification comprises a mutation of a native 4-carboxy-2-hydroxy-6-methoxy-6-oxohexa-2,4-dienoate (CHMOD) methyl esterase gene present in the corresponding native microorganism, wherein the third modification reduces CHMOD methyl esterase activity in the recombinant microorganism with respect to the corresponding native microorganism.

2. The recombinant microorganism of claim 1, wherein the modifications further comprise a fourth modification, wherein the fourth modification comprises a mutation of a native vanillate/3-O-methylgallate O-demethylase gene present in the corresponding native microorganism, wherein the fourth modification reduces vanillate/3-O-methylgallate O-demethylase activity in the recombinant microorganism with respect to the corresponding native microorganism.

3. The recombinant microorganism of claim 2, wherein the mutation of the native vanillate/3-O-methylgallate O-demethylase gene comprises at least one of:
a mutation of a native gene encoding LigM of *Novosphingobium aromaticivorans*; and
a mutation of a native gene encoding VanA of *Novosphingobium aromaticivorans*.

4. The recombinant microorganism of claim 1, wherein the recombinant microorganism exhibits enhanced production of 2-pyrone-4,6-dicarboxylic acid with respect to the corresponding native microorganism.

5. A method for producing 2-pyrone-4,6-dicarboxylic acid comprising culturing the recombinant microorganism as recited in claim 1 in a medium comprising a plant-derived phenolic.

6. The method of claim 5, wherein the plant-derived phenolic comprises a phenolic selected from the group consisting of a syringyl phenolic, a guaiacyl phenolic, and ap-hydroxyphenyl phenolic.

7. The method of claim 5, wherein the medium comprises depolymerized lignin comprising the plant-derived phenolic.

8. The method of claim 5, wherein the medium comprises chemically depolymerized lignin comprising the plant-derived phenolic.

9. The method of claim 5, further comprising isolating the 2-pyrone-4,6-dicarboxylic acid from the medium and/or the recombinant microorganism.

10. The recombinant microorganism of claim 2, wherein the mutation of the native vanillate/3-O-methylgallate O-demethylase gene comprises each of:
a mutation of a native gene encoding LigM of *Novosphingobium aromaticivorans*; and
a mutation of a native gene encoding VanA of *Novosphingobium aromaticivorans*.

* * * * *

SEQUENCE LISTING

```
<160> NUMBER OF SEQ ID NOS: 36

<210> SEQ ID NO 1
<211> LENGTH: 891
<212> TYPE: DNA
<213> ORGANISM: Novosphingobium aromaticivorans

<400> SEQUENCE: 1
atgaccgacc agaaccgcat cgtaagctgg cacgccaatc cgtcgaagcc gcgctacacc      60
ccgccgccgg gcgcggtcga cgcgcattgc cacgtcttcg gcccgatggc gcagttcccc     120
ttctcggcca aggccaagta cctgcccgag gacgccggcc ccgacatgct cttcgccctg     180
cgcgaccacc tcggcttcga gcgcaacgtg atcgtccagg caagctgcca cggcaccgac     240
aacgccgcca cgcttgatgc catcgccagg tcgaacggaa aggcgcgcgg cgtcgccgtc     300
gtcgatcccg ccatctcgga gacggacctc caggctctcc acgaaggcgg catccgcggc     360
atccgcttca acttcctcaa gcgcctcgtc gacgatgcgc ccaaggacaa gttcctcgaa     420
gtcgcccggc gcctgcccaa gggttggcac gtcgtgatct atttcgaggc cgacatcctc     480
gaggaactgc gtccgttcat ggatgcgatc cccgtgccgc tggtcatcga ccacatgggc     540
cgccccgatg tccgccaggg ccccgacggc gccgacatga aggccttccg caacttcctg     600
aacagccgcg acgacatctg gttcaaggcc acctgccccg accggctcga cgcgatcaag     660
```

```
gaaggcggcg cgggcgatcc gtggaacgcc tttgccgatg ccgtcgcgcc gctcgttgcc    720
gactaccagg accgggtcct gtggggggacc gactggccgc accccaacat ggacaccgag    780
atccccgacg acggccatct cgtcgacatg atccccgca tcgccccgac cgaggaactg     840
caacgcaagc tcctcgtcga caatccgatg cggctctact gggccgactg a             891
```

<210> SEQ ID NO 2
<211> LENGTH: 296
<212> TYPE: PRT
<213> ORGANISM: Novosphingobium aromaticivorans

<400> SEQUENCE: 2

```
Met Thr Asp Gln Asn Arg Ile Val Ser Trp His Ala Asn Pro Ser Lys
1               5                   10                  15

Pro Arg Tyr Thr Pro Pro Gly Ala Val Asp Ala His Cys His Val
            20                  25                  30

Phe Gly Pro Met Ala Gln Phe Pro Phe Ser Ala Lys Ala Lys Tyr Leu
        35                  40                  45

Pro Glu Asp Ala Gly Pro Asp Met Leu Phe Ala Leu Arg Asp His Leu
    50                  55                  60

Gly Phe Glu Arg Asn Val Ile Val Gln Ala Ser Cys His Gly Thr Asp
65                  70                  75                  80

Asn Ala Ala Thr Leu Asp Ala Ile Ala Arg Ser Asn Gly Lys Ala Arg
                85                  90                  95

Gly Val Ala Val Val Asp Pro Ala Ile Ser Glu Thr Asp Leu Gln Ala
            100                 105                 110

Leu His Glu Gly Gly Ile Arg Gly Ile Arg Phe Asn Phe Leu Lys Arg
        115                 120                 125

Leu Val Asp Asp Ala Pro Lys Asp Lys Phe Leu Glu Val Ala Arg Arg
    130                 135                 140

Leu Pro Lys Gly Trp His Val Val Ile Tyr Phe Glu Ala Asp Ile Leu
145                 150                 155                 160

Glu Glu Leu Arg Pro Phe Met Asp Ala Ile Pro Val Pro Leu Val Ile
                165                 170                 175

Asp His Met Gly Arg Pro Asp Val Arg Gln Gly Pro Asp Gly Ala Asp
            180                 185                 190

Met Lys Ala Phe Arg Asn Phe Leu Asn Ser Arg Asp Asp Ile Trp Phe
        195                 200                 205

Lys Ala Thr Cys Pro Asp Arg Leu Asp Ala Ile Lys Glu Gly Gly Ala
    210                 215                 220

Gly Asp Pro Trp Asn Ala Phe Ala Asp Ala Val Ala Pro Leu Val Ala
225                 230                 235                 240

Asp Tyr Gln Asp Arg Val Leu Trp Gly Thr Asp Trp Pro His Pro Asn
                245                 250                 255

Met Asp Thr Glu Ile Pro Asp Asp Gly His Leu Val Asp Met Ile Pro
            260                 265                 270

Arg Ile Ala Pro Thr Glu Glu Leu Gln Arg Lys Leu Leu Val Asp Asn
        275                 280                 285

Pro Met Arg Leu Tyr Trp Ala Asp
    290                 295
```

<210> SEQ ID NO 3
<211> LENGTH: 813
<212> TYPE: DNA
<213> ORGANISM: Novosphingobium aromaticivorans

<400> SEQUENCE: 3

```
atggcggcat gctcggcacc atgcgagtct gaaccgatgg ccttgaaata ctaccacgcc      60
gaaccgctgg ccaactctct caagtcgatg gtcccgctca aggaaaaggg cctcgcctac     120
gagagcatct acgtcgatct gcacaagttc gagcagcatc agccgtggtt caccgcgatc     180
aatcccgaag gccaggtgcc ggtgctcgac catgacggca cgatcatcac gcacacgacg     240
gtgatcaacg aatacctcga ggatgccttc cccgatgccc agcccgccga tgcgcccctg     300
cgtccgcgcg acccggtggg tgcggcgcgc atgcgctact ggaacaagtt catcgacgag     360
cacgtgatga actacgtctc gatgcacgga tggcaccgca tggtcggcgt gatcgcccgc     420
aacatcgcca gcggcgattt cgagaaactg ctcgaaagca ttccgctgcc cgatcagcgc     480
aagaagtggg ctaccgcgcg atcgggcttt tccgaagccg atctcgccaa tgccaccgcc     540
aagatcgaat acgcgctcga caaggtcgag aagcaactcg gcgagacgaa gtggctggcg     600
ggcgacacct acacgcttgc cgacatcaac ttctattcgc actgcggcgc gatggtcgaa     660
cgcatgttcc cggaaatgga agtggcgagg cgcgcgccgc gcctgtgcga atggcgtgat     720
cgcgttgccg cgcggcctgc cgtcgccgaa gcgctgaaaa gcgaagaccg cactgcgccc     780
gggctgcgcg tctggtcggg agaagtgcgc tga                                  813
```

<210> SEQ ID NO 4
<211> LENGTH: 270
<212> TYPE: PRT
<213> ORGANISM: Novosphingobium aromaticivorans

<400> SEQUENCE: 4

```
Met Ala Ala Cys Ser Ala Pro Cys Glu Ser Glu Pro Met Ala Leu Lys
1               5                   10                  15

Tyr Tyr His Ala Glu Pro Leu Ala Asn Ser Leu Lys Ser Met Val Pro
            20                  25                  30

Leu Lys Glu Lys Gly Leu Ala Tyr Glu Ser Ile Tyr Val Asp Leu His
        35                  40                  45

Lys Phe Glu Gln His Gln Pro Trp Phe Thr Ala Ile Asn Pro Glu Gly
    50                  55                  60

Gln Val Pro Val Leu Asp His Asp Gly Thr Ile Ile Thr His Thr Thr
65                  70                  75                  80

Val Ile Asn Glu Tyr Leu Glu Asp Ala Phe Pro Asp Ala Gln Pro Ala
                85                  90                  95

Asp Ala Pro Leu Arg Pro Arg Asp Pro Val Gly Ala Ala Arg Met Arg
            100                 105                 110

Tyr Trp Asn Lys Phe Ile Asp Glu His Val Met Asn Tyr Val Ser Met
        115                 120                 125

His Gly Trp His Arg Met Val Gly Val Ile Ala Arg Asn Ile Ala Ser
    130                 135                 140

Gly Asp Phe Glu Lys Leu Leu Glu Ser Ile Pro Leu Pro Asp Gln Arg
145                 150                 155                 160

Lys Lys Trp Ala Thr Ala Arg Ser Gly Phe Ser Glu Ala Asp Leu Ala
                165                 170                 175

Asn Ala Thr Ala Lys Ile Glu Tyr Ala Leu Asp Lys Val Glu Lys Gln
            180                 185                 190

Leu Gly Glu Thr Lys Trp Leu Ala Gly Asp Thr Tyr Thr Leu Ala Asp
        195                 200                 205

Ile Asn Phe Tyr Ser His Cys Gly Ala Met Val Glu Arg Met Phe Pro
```

```
                210                 215                 220
Glu Met Glu Val Ala Arg Arg Ala Pro Arg Leu Cys Glu Trp Arg Asp
225                 230                 235                 240

Arg Val Ala Ala Arg Pro Ala Val Ala Glu Ala Leu Lys Ser Glu Asp
                245                 250                 255

Arg Thr Ala Pro Gly Leu Arg Val Trp Ser Gly Glu Val Arg
            260                 265                 270

<210> SEQ ID NO 5
<211> LENGTH: 738
<212> TYPE: DNA
<213> ORGANISM: Novosphingobium aromaticivorans

<400> SEQUENCE: 5
atggccggct tcgtcctgat ccatggttcc tggcatggtg gctggtgctt cgatcccgtc     60
gccgaaatcc tgcgcgcgcg cggccacacg gtcgtcgcgc cgacgctgcc cgggatggga    120
ggcacggcgg aggaaatggc ggcggtcacg ctggatggct ggggcgaatt tgctgcgcag    180
cattgtcgcg acctgaaggc acggggcgtc ggccccgtgg tcctcgccgg ccactcgcgc    240
ggaggccttg tcgtctccac cgcggccgag cgcgaccctt ccgcgatgga cgccatcgtc    300
tacatatgcg cgatgatgct gccctcgggc atgagtcgcg ccgggttcaa ggaactggaa    360
ggcccgaacc ccgctttcga cgcgatcatc tcgaaggttc acggcggcat cgccacggtc    420
atcgacacgc agaatgctgc accggtcttt gcacaaattt cgccgcccga tctggtcgag    480
gcggcaatgg caaggctcgt ggccgaaccc catgctccgc gttcgcagca gatcaaggtc    540
acgccggaac gctggggcag cctcccgcgc acttacgtcg aatgcacgct cgaccgcacc    600
attccgatcg aaagccagcg ccgcatgatc gcgatgtcgc cgggtgcgaa cgtggtgact    660
ctggaggcgg accacagtcc ctatctgtcg aaaccgcagg aactggccga ggcgctggaa    720
gcggccattc cgcctga                                                   738

<210> SEQ ID NO 6
<211> LENGTH: 245
<212> TYPE: PRT
<213> ORGANISM: Novosphingobium aromaticivorans

<400> SEQUENCE: 6

Met Ala Gly Phe Val Leu Ile His Gly Ser Trp His Gly Gly Trp Cys
1               5                   10                  15

Phe Asp Pro Val Ala Glu Ile Leu Arg Ala Arg Gly His Thr Val Val
                20                  25                  30

Ala Pro Thr Leu Pro Gly Met Gly Gly Thr Ala Glu Glu Met Ala Ala
            35                  40                  45

Val Thr Leu Asp Gly Trp Gly Glu Phe Ala Ala Gln His Cys Arg Asp
        50                  55                  60

Leu Lys Ala Arg Gly Val Gly Pro Val Val Leu Ala Gly His Ser Arg
65                  70                  75                  80

Gly Gly Leu Val Val Ser Thr Ala Ala Glu Arg Asp Pro Ser Ala Met
                85                  90                  95

Asp Ala Ile Val Tyr Ile Cys Ala Met Met Leu Pro Ser Gly Met Ser
            100                 105                 110

Arg Ala Gly Phe Lys Glu Leu Glu Gly Pro Asn Pro Ala Phe Asp Ala
        115                 120                 125

Ile Ile Ser Lys Val His Gly Gly Ile Ala Thr Val Ile Asp Thr Gln
    130                 135                 140
```

```
Asn Ala Ala Pro Val Phe Ala Gln Ile Ser Pro Pro Asp Leu Val Glu
145                 150                 155                 160

Ala Ala Met Ala Arg Leu Val Ala Glu Pro His Ala Pro Arg Ser Gln
            165                 170                 175

Gln Ile Lys Val Thr Pro Glu Arg Trp Gly Ser Leu Pro Arg Thr Tyr
        180                 185                 190

Val Glu Cys Thr Leu Asp Arg Thr Ile Pro Ile Glu Ser Gln Arg Arg
    195                 200                 205

Met Ile Ala Met Ser Pro Gly Ala Asn Val Val Thr Leu Glu Ala Asp
210                 215                 220

His Ser Pro Tyr Leu Ser Lys Pro Gln Glu Leu Ala Glu Ala Leu Glu
225                 230                 235                 240

Ala Ala Ile Pro Ala
                245
```

<210> SEQ ID NO 7
<211> LENGTH: 1401
<212> TYPE: DNA
<213> ORGANISM: Novosphingobium aromaticivorans

<400> SEQUENCE: 7

```
atggcggcaa agaacctcga agaggtaatc cagcagaacg gcaacgtcgt cgaaatgctg      60
cgcaattcgc agctcggcgc ttatgtctat ccggtcgttg cgccggaatt ctcgaactgg     120
cgttcggaac agtgggcatg cagcacagcc gccgtgctgt cgaccagtc gcaccacatg     180
gtgaacctct acattcgcgg caaggatgcg ctgaagctcc tgtcggacac catgatcaac     240
agcccgaagg gctggacggt caacaaggcc aagcagtacg tcccgaccac gccctatggc     300
cacgtgatcg cgacgggcat catcttctgg gaagaagagg aaagcttcac ctacgtcggt     360
cgcgcgcccg cttcgaactg gctgcgctac cacgccgcga ccggcggcta cgattgcgag     420
atcgagctgg acgaccgttc gccgatgcgc ccgatgggca gcccgtccg ccgcaaggaa     480
tggcgcttcc agatccaggg ccccaacgcc tgggcggtga tcgagaagct gcacggcggc     540
ccgctcgaac agctcaagtt cttcaacatg agcaccatga acatcgccgg caagaccgtg     600
cgcaccctgc gccacggcat gtcgggcgcg ccgggcctcg aaatctgggg tccctatgac     660
gagcaggaag aaatccgcgc gcgatcctc gaagccggca aggaattcgg cctgattgcc     720
tgcggcagcc gcgcctatcc gtcgaacacg ctcgaatcgg gctggatccc ctcgccgctg     780
cccgccatct acaccggcga aaagctcaag ggcttccgcg aatggctcgc ggcggacagc     840
tacgaagcca ccggttcgat cggcggttcg ttcgtctcgg acaacatcga ggactactac     900
ctcaatccgt gggaactggg ttacggcaac ttcgtgaagt cgaccatga cttccacggt     960
cgcgaagccc tcgaagccct caacccggcc gagcagcgca agaaggtgac gctcgcctgg    1020
aaccccgagg acatggccaa gatcatggcc tcgctgttca atcccgatgg cgaccagtac    1080
aagttcttcg acaccccgct cgcgaactat gcctcgtcga actacgaccg cgtcgtcgat    1140
gcgggcggca agaccgtcgg cttctcgatg ttcaccggct actcgtacaa cgagaagcag    1200
gcgctttcgc tcgccacgat cgatccggaa atcccggtcg caccgagct gcgcgtcgtg    1260
tggggtgaag agaacggcgg cacccgcaag accactgtcg agccgcacaa gcagatcgag    1320
gtccgcgcga tcgtttcgcc ggtcccctac agccgcgtcg ctcgcgaaaa ctacgccgaa    1380
ggctggcgca ccgctcgcta a                                             1401
```

<210> SEQ ID NO 8
<211> LENGTH: 466
<212> TYPE: PRT
<213> ORGANISM: Novosphingobium aromaticivorans

<400> SEQUENCE: 8

```
Met Ala Ala Lys Asn Leu Glu Glu Val Ile Gln Gln Asn Gly Asn Val
1               5                   10                  15

Val Glu Met Leu Arg Asn Ser Gln Leu Gly Ala Tyr Val Tyr Pro Val
            20                  25                  30

Val Ala Pro Glu Phe Ser Asn Trp Arg Ser Glu Gln Trp Ala Trp Gln
        35                  40                  45

His Ser Ala Val Leu Phe Asp Gln Ser His His Met Val Asn Leu Tyr
    50                  55                  60

Ile Arg Gly Lys Asp Ala Leu Lys Leu Leu Ser Asp Thr Met Ile Asn
65                  70                  75                  80

Ser Pro Lys Gly Trp Thr Val Asn Lys Ala Lys Gln Tyr Val Pro Thr
                85                  90                  95

Thr Pro Tyr Gly His Val Ile Gly Asp Gly Ile Ile Phe Trp Glu Glu
            100                 105                 110

Glu Glu Ser Phe Thr Tyr Val Gly Arg Ala Pro Ala Ser Asn Trp Leu
        115                 120                 125

Arg Tyr His Ala Ala Thr Gly Gly Tyr Asp Cys Glu Ile Glu Leu Asp
    130                 135                 140

Asp Arg Ser Pro Met Arg Pro Met Gly Lys Pro Val Arg Arg Lys Glu
145                 150                 155                 160

Trp Arg Phe Gln Ile Gln Gly Pro Asn Ala Trp Ala Val Ile Glu Lys
                165                 170                 175

Leu His Gly Gly Pro Leu Glu Gln Leu Lys Phe Phe Asn Met Ser Thr
            180                 185                 190

Met Asn Ile Ala Gly Lys Thr Val Arg Thr Leu Arg His Gly Met Ser
        195                 200                 205

Gly Ala Pro Gly Leu Glu Ile Trp Gly Pro Tyr Asp Glu Gln Glu Glu
    210                 215                 220

Ile Arg Ala Ala Ile Leu Glu Ala Gly Lys Glu Phe Gly Leu Ile Ala
225                 230                 235                 240

Cys Gly Ser Arg Ala Tyr Pro Ser Asn Thr Leu Glu Ser Gly Trp Ile
                245                 250                 255

Pro Ser Pro Leu Pro Ala Ile Tyr Thr Gly Glu Lys Leu Lys Gly Phe
            260                 265                 270

Arg Glu Trp Leu Ala Ala Asp Ser Tyr Glu Ala Thr Gly Ser Ile Gly
        275                 280                 285

Gly Ser Phe Val Ser Asp Asn Ile Glu Asp Tyr Tyr Leu Asn Pro Trp
    290                 295                 300

Glu Leu Gly Tyr Gly Asn Phe Val Lys Phe Asp His Asp Phe His Gly
305                 310                 315                 320

Arg Glu Ala Leu Glu Ala Leu Asn Pro Ala Glu Gln Arg Lys Lys Val
                325                 330                 335

Thr Leu Ala Trp Asn Pro Glu Asp Met Ala Lys Ile Met Ala Ser Leu
            340                 345                 350

Phe Asn Pro Asp Gly Asp Gln Tyr Lys Phe Phe Asp Thr Pro Leu Ala
        355                 360                 365

Asn Tyr Ala Ser Ser Asn Tyr Asp Arg Val Val Asp Ala Gly Gly Lys
    370                 375                 380
```

```
Thr Val Gly Phe Ser Met Phe Thr Gly Tyr Ser Tyr Asn Glu Lys Gln
385                 390                 395                 400

Ala Leu Ser Leu Ala Thr Ile Asp Pro Glu Ile Pro Val Gly Thr Glu
            405                 410                 415

Leu Arg Val Val Trp Gly Glu Glu Asn Gly Gly Thr Arg Lys Thr Thr
        420                 425                 430

Val Glu Pro His Lys Gln Ile Glu Val Arg Ala Ile Val Ser Pro Val
        435                 440                 445

Pro Tyr Ser Arg Val Ala Arg Glu Asn Tyr Ala Glu Gly Trp Arg Thr
    450                 455                 460

Ala Arg
465

<210> SEQ ID NO 9
<211> LENGTH: 1071
<212> TYPE: DNA
<213> ORGANISM: Novosphingobium aromaticivorans

<400> SEQUENCE: 9
atgagcggcg gcgaaccggt tccgaagctg tcggcgaaac ccgccgccac gtatcttcgc        60
aacacctggt acgtggcggg ctgggccagc gatcttgccg cgagccgca  gcagcgcacg      120 ttcctggaag agccggtggc gctcttccgc gacggacacg gtgaggcgaa ggccatcggc      180
gggcgctgcc cgcaccggtt cgcgccgctc ggccatggca cgtcgtcga cggggcgctg      240 atgtgcccct accacggcct gcgtttcgat ggggatggac gctgcgtcca caacccgcat      300
cccggcggac atcttcccga tgcgcggcag cgggtctatc cgcttgtcga gcggcatgcc      360
ttgctgtgga tatggatggg cgatgcagca aaggctgatc cggcatcgat cccggacttt      420
tcgtggcttt cggaccccag atgggaggcc gtgcgcgggg ccacggtcgc cgagggtcac      480
ttcgagctct acagcgacaa cattctcgac ctcagccacg ccaacttcgt ccacccggcg      540
ctggtcgcca cgcattcac cgaaggcgag cgcaagttct ggcaggacgg agacaatgtc      600
tttgccgaat acgtgcggct gaacgacgag cttccgtcg gcatttcggc ggtgatgggg      660 accgagggc ggccgcagga tttctacggc atggtcaagt ggcatgcgcc ggccgtactc      720
tacttcgatt tccgcgcggg cgagccgggc acgccgcgcg agcaatgcac gctgctgcca      780
tcgctccatg ccttcacgcc ggaaacccct gacacgacgc attacttctg gcgaccgcg      840 cgcgactaca ggctgggcga cgcggagttc accgccggaa tgcgcgccgc gctcgaattc      900
gcgttcgagc aggaagacat gccgatcatc cgcgacagcc accggctcat gcgcggcgag      960
gacttctggg cgcttcgccc gctgatcctc ggtggcgatg gtggcggggt gcgggcccgg     1020
agaatgctgc aacggctgat cgagcgcgag agacagcagg acgctgcctg a             1071

<210> SEQ ID NO 10
<211> LENGTH: 356
<212> TYPE: PRT
<213> ORGANISM: Novosphingobium aromaticivorans

<400> SEQUENCE: 10

Met Ser Gly Gly Glu Pro Val Pro Lys Leu Ser Ala Lys Pro Ala Ala
1               5                   10                  15

Thr Tyr Leu Arg Asn Thr Trp Tyr Val Ala Gly Trp Ala Ser Asp Leu
            20                  25                  30

Ala Gly Glu Pro Gln Gln Arg Thr Phe Leu Glu Glu Pro Val Ala Leu
        35                  40                  45
```

Phe Arg Asp Gly His Gly Glu Ala Lys Ala Ile Gly Gly Arg Cys Pro
 50                  55                  60

His Arg Phe Ala Pro Leu Gly His Gly Ser Val Val Asp Gly Ala Leu
 65                  70                  75                  80

Met Cys Pro Tyr His Gly Leu Arg Phe Asp Gly Asp Gly Arg Cys Val
                 85                  90                  95

His Asn Pro His Pro Gly Gly His Leu Pro Asp Ala Arg Gln Arg Val
            100                 105                 110

Tyr Pro Leu Val Glu Arg His Ala Leu Leu Trp Ile Trp Met Gly Asp
        115                 120                 125

Ala Ala Lys Ala Asp Pro Ala Ser Ile Pro Asp Phe Ser Trp Leu Ser
130                 135                 140

Asp Pro Arg Trp Glu Ala Val Arg Gly Ala Thr Val Ala Glu Gly His
145                 150                 155                 160

Phe Glu Leu Tyr Ser Asp Asn Ile Leu Asp Leu Ser His Ala Asn Phe
                165                 170                 175

Val His Pro Ala Leu Val Ala Ser Ala Phe Thr Glu Gly Glu Arg Lys
            180                 185                 190

Phe Trp Gln Asp Gly Asp Asn Val Phe Ala Glu Tyr Val Arg Leu Asn
        195                 200                 205

Asp Glu Leu Ser Val Gly Ile Ser Ala Val Met Gly Thr Glu Gly Arg
210                 215                 220

Pro Gln Asp Phe Tyr Gly Met Val Lys Trp His Ala Pro Ala Val Leu
225                 230                 235                 240

Tyr Phe Asp Phe Arg Ala Gly Glu Pro Gly Thr Pro Arg Glu Gln Cys
                245                 250                 255

Thr Leu Leu Pro Ser Leu His Ala Phe Thr Pro Glu Thr Pro Asp Thr
            260                 265                 270

Thr His Tyr Phe Trp Ala Thr Ala Arg Asp Tyr Arg Leu Gly Asp Ala
        275                 280                 285

Glu Phe Thr Ala Gly Met Arg Ala Ala Leu Glu Phe Ala Phe Glu Gln
290                 295                 300

Glu Asp Met Pro Ile Ile Arg Asp Ser His Arg Leu Met Arg Gly Glu
305                 310                 315                 320

Asp Phe Trp Ala Leu Arg Pro Leu Ile Leu Gly Gly Asp Gly Gly
                325                 330                 335

Val Arg Ala Arg Arg Met Leu Gln Arg Leu Ile Glu Arg Glu Arg Gln
            340                 345                 350

Gln Asp Ala Ala
        355

<210> SEQ ID NO 11
<211> LENGTH: 1389
<212> TYPE: DNA
<213> ORGANISM: Novosphingobium aromaticivorans

<400> SEQUENCE: 11
atgtcccaga ccctagagca ggtcatccag aacgctggtg atctcgtgaa cttcgtccgc    60
aaccagcagg tcggccccaa cgtctatccc ggcgttccgg cggaatactc gaactggcgc   120
aacgaacagt gggcctgggc gcactccgca gtgctctaca ccagtcgta ccacatggtc    180 gatctggcgg ttaagggtcc ggatgcgttc aagatgctcg aacacctcgg catcaactcg   240
ttcaagaact tccagccgga tcgcgccaag cagttcgtcc ccgtcacgcc cgacggctat   300
gtcatcggcg acgtgatcct gttctatctc gacgagaacc atttcaacct cgtcggtcgc   360

```
gcgccgacga tcgaatgggt cgaatatcac gccgccagcg gcaactggaa cgtcaccgtc    420
gaacgtgacg agcgttgggc catgcgcacc gatggcaagc gcaattccta ccgcttccag    480
atccagggcc cgaacgcgat gaagatcatc gagaaggcca ccggcaagac cgctccggat    540
ctcaagttct tccacatgac ccgcatgacc atcggcggca aggaagtgcg cgcgctgcgc    600
cacggcatgg ccggccagcc gggcttcgag ctgatgggtc cgtgggaaga ctacggcgct    660
gtccatgccg cgctggtcga ggccggcaag gggttccaga tgcccctcgt cggcggccgc    720
gcctattcgt cgaacacgct ggaatcgggc tggatcccct cgcccttccc ggcgatctac    780
accggcgagg cgctgcgccc ctaccgcgaa tggctctcgg ccaattccta tgaagccaag    840
tgctcggttg cggcagcta tgtgcccgaa accatcgagg ctactacac cacgccgtgg    900 gatctgggtt acgcccctt cgtcaagttc gaccatgact tcatcggtcg cgccgcgctc    960
gagaagatgg cggccgaagg caagcaccgc accaaggtca cgctcgcgct cgacaacgaa   1020
gacgtgatgc gcgtccagtc ctcggcgctc agcaagggcg atcgcgccaa gttcatggaa   1080
tacccgagcg cggtctattc gatgcacccg ttcgaccagg tgcttgccga tggcaagatg   1140
gtcggcctct ccacctggat cggctacacc gccaacgagg caagttcct cacgctggcc   1200 atgatggagc cgggttacgt cgaaccgggc acgcaagtca gcctgctctg gggcgaaccg   1260 aacgcggca ccaccaagcc caccgtcgaa ccccacgtcc agaccgagat caaggccacc   1320
gtcgccgccg tccctactc ggaagtggcg cgcgacagct acgccgaggg ctggcgcacc   1380
aagaagtaa                                                            1389
```

<210> SEQ ID NO 12
<211> LENGTH: 461
<212> TYPE: PRT
<213> ORGANISM: Novosphingobium aromaticivorans

<400> SEQUENCE: 12

```
Met Ser Gln Thr Leu Glu Gln Val Ile Gln Asn Ala Gly Asp Leu Val
1               5                   10                  15

Asn Phe Val Arg Asn Gln Gln Val Gly Pro Asn Val Tyr Pro Gly Val
            20                  25                  30

Pro Ala Glu Tyr Ser Asn Trp Arg Asn Glu Gln Trp Ala Trp Ala His
        35                  40                  45

Ser Ala Val Leu Tyr Asn Gln Ser Tyr His Met Val Asp Leu Ala Val
    50                  55                  60

Lys Gly Pro Asp Ala Phe Lys Met Leu Glu His Leu Gly Ile Asn Ser
65                  70                  75                  80

Phe Lys Asn Phe Gln Pro Asp Arg Ala Lys Gln Phe Val Pro Val Thr
                85                  90                  95

Pro Asp Gly Tyr Val Ile Gly Asp Val Ile Leu Phe Tyr Leu Asp Glu
            100                 105                 110

Asn His Phe Asn Leu Val Gly Arg Ala Pro Thr Ile Glu Trp Val Glu
        115                 120                 125

Tyr His Ala Ala Ser Gly Asn Trp Asn Val Thr Val Glu Arg Asp Glu
    130                 135                 140

Arg Trp Ala Met Arg Thr Asp Gly Lys Arg Asn Ser Tyr Arg Phe Gln
145                 150                 155                 160

Ile Gln Gly Pro Asn Ala Met Lys Ile Ile Glu Lys Ala Thr Gly Lys
                165                 170                 175

Thr Ala Pro Asp Leu Lys Phe Phe His Met Thr Arg Met Thr Ile Gly
```

```
                180             185             190
Gly Lys Glu Val Arg Ala Leu Arg His Gly Met Ala Gly Gln Pro Gly
            195                 200                 205

Phe Glu Leu Met Gly Pro Trp Glu Asp Tyr Gly Ala Val His Ala Leu
210                 215                 220

Val Glu Ala Gly Lys Gly Phe Gln Met Ala Leu Val Gly Gly Arg Ala
225                 230                 235                 240

Tyr Ser Ser Asn Thr Leu Glu Ser Gly Trp Ile Pro Ser Pro Phe Pro
                245                 250                 255

Ala Ile Tyr Thr Gly Glu Ala Leu Arg Pro Tyr Arg Glu Trp Leu Ser
                260                 265                 270

Ala Asn Ser Tyr Glu Ala Lys Cys Ser Val Gly Gly Ser Tyr Val Pro
            275                 280                 285

Glu Thr Ile Glu Gly Tyr Tyr Thr Thr Pro Trp Asp Leu Gly Tyr Gly
            290                 295                 300

Pro Phe Val Lys Phe Asp His Asp Phe Ile Gly Arg Ala Ala Leu Glu
305                 310                 315                 320

Lys Met Ala Ala Glu Gly Lys His Arg Thr Lys Val Thr Leu Ala Leu
                325                 330                 335

Asp Asn Glu Asp Val Met Arg Val Gln Ser Ser Ala Leu Ser Lys Gly
                340                 345                 350

Asp Arg Ala Lys Phe Met Glu Tyr Pro Ser Ala Val Tyr Ser Met His
            355                 360                 365

Pro Phe Asp Gln Val Leu Ala Asp Gly Lys Met Val Gly Leu Ser Thr
        370                 375                 380

Trp Ile Gly Tyr Thr Ala Asn Glu Gly Lys Phe Leu Thr Leu Ala Met
385                 390                 395                 400

Met Glu Pro Gly Tyr Val Glu Pro Gly Thr Gln Val Ser Leu Leu Trp
                405                 410                 415

Gly Glu Pro Asn Gly Gly Thr Thr Lys Pro Thr Val Glu Pro His Val
            420                 425                 430

Gln Thr Glu Ile Lys Ala Thr Val Ala Ala Val Pro Tyr Ser Glu Val
        435                 440                 445

Ala Arg Asp Ser Tyr Ala Glu Gly Trp Arg Thr Lys Lys
        450                 455                 460

<210> SEQ ID NO 13
<211> LENGTH: 438
<212> TYPE: DNA
<213> ORGANISM: Novosphingobium aromaticivorans

<400> SEQUENCE: 13
gtgactgaca acagctcgac cgataagccc aagcctgtgc agaacatcca cgagtacctc      60
gccgagttcg aggacatccc cggcacgcgc atctataccg ctgcccgcgc ccgcaagggg     120
tactggatca accagttcgc gatgagcctg atgaagccgg agaaccgcga gcggttcaag     180
gcgaacgagc gggcctatct tgacgaatgg aagatcagcg aggaggccaa ggaagcgctg     240
ctcgcgcggg actacaaccg cctgctcgac cttggcggca acgtctattt cctgtcgaag     300
ctgttctcct cggacggact gccgttcgcc gaggcggtca gcacgatgac cgacatgacc     360
tggccggaat accgccagat gatgctggac ggcgacgca agcccgaagg caaccgatcg     420
atcaagggag gctattga                                                   438

<210> SEQ ID NO 14
```

<211> LENGTH: 145
<212> TYPE: PRT
<213> ORGANISM: Novosphingobium aromaticivorans

<400> SEQUENCE: 14

```
Met Thr Asp Asn Ser Ser Thr Asp Lys Pro Lys Pro Val Gln Asn Ile
1               5                  10                  15

His Glu Tyr Leu Ala Glu Phe Glu Asp Ile Pro Gly Thr Arg Ile Tyr
            20                  25                  30

Thr Ala Arg Ala Arg Lys Gly Tyr Trp Ile Asn Gln Phe Ala Met
        35                  40                  45

Ser Leu Met Lys Pro Glu Asn Arg Glu Arg Phe Lys Ala Asn Glu Arg
50                  55                  60

Ala Tyr Leu Asp Glu Trp Lys Ile Ser Glu Glu Ala Lys Glu Ala Leu
65                  70                  75                  80

Leu Ala Arg Asp Tyr Asn Arg Leu Leu Asp Leu Gly Gly Asn Val Tyr
                85                  90                  95

Phe Leu Ser Lys Leu Phe Ser Ser Asp Gly Leu Pro Phe Ala Glu Ala
            100                 105                 110

Val Ser Thr Met Thr Asp Met Thr Trp Pro Glu Tyr Arg Gln Met Met
        115                 120                 125

Leu Asp Gly Gly Arg Lys Pro Glu Gly Asn Arg Ser Ile Lys Gly Gly
130                 135                 140

Tyr
145
```

<210> SEQ ID NO 15
<211> LENGTH: 843
<212> TYPE: DNA
<213> ORGANISM: Novosphingobium aromaticivorans

<400> SEQUENCE: 15

| | | | | | |
|---|---|---|---|---|---|
| atggcccgca | taaccgctgg | cgttggctcc | agccacgttc | cgctgctggg | tgtcgctgtt | 60 |
| gatcagggca | agtggcagga | cgactatttc | ggcccgatct | tcaagggtta | tgaatggacc | 120 |
| cgcgaatggg | aaaagcgcga | gaagcccgat | gtggtcattc | tggtctacaa | cgaccacgct | 180 |
| tcggcattcg | acgcgaacat | catcccgacc | ttcgcaatcg | gctgcggcga | gcactacaag | 240 |
| tcggccgatg | aaggctgggg | cccgcgcccg | gtgcccgacg | tggaaggcca | tgccgacctt | 300 |
| gcctggcaca | tcgcgcagag | cctgatcctc | gacgatttcg | acatgaccat | catcaacgag | 360 |
| atggatgtgg | accacggcct | gaccgtgccg | ctctcgatga | tgttcggcca | gcccgagaag | 420 |
| tggccgtgca | aggtcgtgcc | gctggcggtg | aacgtcgtca | cctatccggt | gccgtcgggc | 480 |
| aaccgctgct | gggcgctggg | cgaggcgatc | gcccgcgcgg | tggaaagctt | ccccgaggac | 540 |
| ctcaacgtgc | agatctgggg | cacgggcggc | atgagccacc | agctccaggg | cccgcgcgcc | 600 |
| ggcctgctca | accgcgagtg | ggacaacaag | ttcctcgaca | tgctggaatc | ggacaacgac | 660 |
| gatgtccgct | acattccgca | tatcgaatac | ctgcgcgaga | ccggctcgga | aggcatcgag | 720 |
| atggtcatgt | ggctgatcat | gcgcggcgcg | ctcggcaaga | aggtcaagcg | cctgaaccgc | 780 |
| cattaccaca | ttccctgcag | caacaccgcg | atcgggcaca | tcgtgctcga | gcccgcggac | 840 |
| tga | | | | | | 843 |

<210> SEQ ID NO 16
<211> LENGTH: 280
<212> TYPE: PRT
<213> ORGANISM: Novosphingobium aromaticivorans

<400> SEQUENCE: 16

```
Met Ala Arg Ile Thr Ala Gly Val Gly Ser Ser His Val Pro Leu Leu
1               5                   10                  15
Gly Val Ala Val Asp Gln Gly Lys Trp Gln Asp Asp Tyr Phe Gly Pro
            20                  25                  30
Ile Phe Lys Gly Tyr Glu Trp Thr Arg Glu Trp Glu Lys Arg Glu Lys
        35                  40                  45
Pro Asp Val Val Ile Leu Val Tyr Asn Asp His Ala Ser Ala Phe Asp
    50                  55                  60
Ala Asn Ile Ile Pro Thr Phe Ala Ile Gly Cys Gly Glu His Tyr Lys
65                  70                  75                  80
Ser Ala Asp Glu Gly Trp Gly Pro Arg Pro Val Pro Asp Val Glu Gly
                85                  90                  95
His Ala Asp Leu Ala Trp His Ile Ala Gln Ser Leu Ile Leu Asp Asp
            100                 105                 110
Phe Asp Met Thr Ile Ile Asn Glu Met Asp Val Asp His Gly Leu Thr
        115                 120                 125
Val Pro Leu Ser Met Met Phe Gly Gln Pro Glu Lys Trp Pro Cys Lys
130                 135                 140
Val Val Pro Leu Ala Val Asn Val Val Thr Tyr Pro Val Pro Ser Gly
145                 150                 155                 160
Asn Arg Cys Trp Ala Leu Gly Glu Ala Ile Ala Arg Ala Val Glu Ser
                165                 170                 175
Phe Pro Glu Asp Leu Asn Val Gln Ile Trp Gly Thr Gly Gly Met Ser
            180                 185                 190
His Gln Leu Gln Gly Pro Arg Ala Gly Leu Leu Asn Arg Glu Trp Asp
        195                 200                 205
Asn Lys Phe Leu Asp Met Leu Glu Ser Asp Asn Asp Val Arg Tyr
210                 215                 220
Ile Pro His Ile Glu Tyr Leu Arg Glu Thr Gly Ser Glu Gly Ile Glu
225                 230                 235                 240
Met Val Met Trp Leu Ile Met Arg Gly Ala Leu Gly Lys Lys Val Lys
                245                 250                 255
Arg Leu Asn Arg His Tyr His Ile Pro Cys Ser Asn Thr Ala Ile Gly
            260                 265                 270
His Ile Val Leu Glu Pro Ala Asp
        275                 280
```

<210> SEQ ID NO 17
<211> LENGTH: 402
<212> TYPE: DNA
<213> ORGANISM: Novosphingobium aromaticivorans

<400> SEQUENCE: 17

```
atgacacctg aaggaaaccg cgaggaccgg gcggccgtgg acaaggcgct ccgccgcgcg    60
attccgctgt tcgatggcga tctcgccacg cgcggatacg agctcaacgc gatgtgtttt   120
tccttcaacg aaaaagccaa tgcgaggcc tttctggccg atgaagaagc ctattgccgc   180
aagttcaacc tgacgccgca gcaacgcaag gccgtggcca tcgcgatgt gctcgcgatg   240
ctcgatgcgg gcgggaacgt ctattatctg gccaagctgg ccggcatttt cggccttggc   300
gtgcaggacc tgggcgcatt gcagaccggc atgtcggtcg ctgatttcaa ggccatgctc   360
gtgcgctggg ccgacagtat tcccaacaag gagaacgcgt ga                     402
```

<210> SEQ ID NO 18
<211> LENGTH: 133
<212> TYPE: PRT
<213> ORGANISM: Novosphingobium aromaticivorans

<400> SEQUENCE: 18

```
Met Thr Pro Glu Gly Asn Arg Glu Asp Arg Ala Ala Val Asp Lys Ala
1               5                   10                  15

Leu Arg Arg Ala Ile Pro Leu Phe Asp Gly Asp Leu Ala Thr Arg Gly
            20                  25                  30

Tyr Glu Leu Asn Ala Met Cys Phe Ser Phe Asn Glu Lys Ala Asn Arg
        35                  40                  45

Glu Ala Phe Leu Ala Asp Glu Glu Ala Tyr Cys Arg Lys Phe Asn Leu
    50                  55                  60

Thr Pro Gln Gln Arg Lys Ala Val Ala Asp Arg Asp Val Leu Ala Met
65                  70                  75                  80

Leu Asp Ala Gly Gly Asn Val Tyr Tyr Leu Ala Lys Leu Ala Gly Ile
                85                  90                  95

Phe Gly Leu Gly Val Gln Asp Leu Gly Ala Leu Gln Thr Gly Met Ser
            100                 105                 110

Val Ala Asp Phe Lys Ala Met Leu Val Arg Trp Ala Asp Ser Ile Pro
        115                 120                 125

Asn Lys Glu Asn Ala
    130
```

<210> SEQ ID NO 19
<211> LENGTH: 843
<212> TYPE: DNA
<213> ORGANISM: Novosphingobium aromaticivorans

<400> SEQUENCE: 19

```
atggccaagg tcattggcgg ttatttcacc agccacgtcc cgggcattgg cggcgccatc     60
gttcgcggcg atcaggaaac gccttattgg aagccgttct tcgatggcta cccgcccatc    120
cgcgaatggc tggtggaggc ccggcctgac gtcgcaatcg tcttttccaa cgaccacggc    180
ctcaacttct tcctcgacaa gatgccgacc tttgccgtcg gtgcggcaga gcgctacgac    240
aatgccgacg agggctgggg cctgccggtc tacaagagct cgccggtca cccggcgctt     300
tcctggcacc tgatcgacag tctggtgcgt gacgagttcg acatcacaac ctgccagaag    360
atgctggtcg atcacgcggt ttcgatcccg ttcgaactga tctacccggg tgcggagagc    420
tggccgatca agctcgtccc gatctcgatc aacaccgtgc aatatccgct gccgagtcct    480
aagcgctgcc ttgcgcttgg ccgtgcggta ggtcgcgcgc tgcaatcctg gccggtgac    540
gaacgtgtcc tgatttgtgg taccggcggg ctttcgcatc agctggacgg tccacgcgcg    600
ggtttcatga acccggacta cgacatgttc tgccttgata tcttgcggc caatcccgac    660
gccctgaccg ccataccgc cgagcaggta gccgagcttg ccggaacgca gggcgtcgag    720
attctcaact ggatcgcggc gcgcggggca atgggcgatg tgccgctgca cgaggtcagc    780
cggaactacc atatccccat cagcaatact gcggccgcca gctcctcct cgagcctgcc    840
tga                                                                  843
```

<210> SEQ ID NO 20
<211> LENGTH: 280
<212> TYPE: PRT
<213> ORGANISM: Novosphingobium aromaticivorans

<400> SEQUENCE: 20

```
Met Ala Lys Val Ile Gly Gly Tyr Phe Thr Ser His Val Pro Gly Ile
1               5                   10                  15
Gly Gly Ala Ile Val Arg Gly Asp Gln Glu Thr Pro Tyr Trp Lys Pro
            20                  25                  30
Phe Phe Asp Gly Tyr Pro Pro Ile Arg Glu Trp Leu Val Glu Ala Arg
        35                  40                  45
Pro Asp Val Ala Ile Val Phe Ser Asn Asp His Gly Leu Asn Phe Phe
    50                  55                  60
Leu Asp Lys Met Pro Thr Phe Ala Val Gly Ala Ala Glu Arg Tyr Asp
65                  70                  75                  80
Asn Ala Asp Glu Gly Trp Gly Leu Pro Val Tyr Lys Ser Phe Ala Gly
                85                  90                  95
His Pro Ala Leu Ser Trp His Leu Ile Asp Ser Leu Val Arg Asp Glu
            100                 105                 110
Phe Asp Ile Thr Thr Cys Gln Lys Met Leu Val Asp His Ala Val Ser
        115                 120                 125
Ile Pro Phe Glu Leu Ile Tyr Pro Gly Ala Glu Ser Trp Pro Ile Lys
    130                 135                 140
Leu Val Pro Ile Ser Ile Asn Thr Val Gln Tyr Pro Leu Pro Ser Pro
145                 150                 155                 160
Lys Arg Cys Leu Ala Leu Gly Arg Ala Val Gly Arg Ala Leu Gln Ser
                165                 170                 175
Trp Ala Gly Asp Glu Arg Val Leu Ile Cys Gly Thr Gly Gly Leu Ser
            180                 185                 190
His Gln Leu Asp Gly Pro Arg Ala Gly Phe Met Asn Pro Asp Tyr Asp
        195                 200                 205
Met Phe Cys Leu Asp Asn Leu Ala Ala Asn Pro Asp Ala Leu Thr Gly
    210                 215                 220
His Thr Ala Glu Gln Val Ala Glu Leu Ala Gly Thr Gln Gly Val Glu
225                 230                 235                 240
Ile Leu Asn Trp Ile Ala Ala Arg Gly Ala Met Gly Asp Val Pro Leu
                245                 250                 255
His Glu Val Ser Arg Asn Tyr His Ile Pro Ile Ser Asn Thr Ala Ala
            260                 265                 270
Ala Ser Leu Leu Leu Glu Pro Ala
        275                 280
```

<210> SEQ ID NO 21
<211> LENGTH: 1170
<212> TYPE: DNA
<213> ORGANISM: Novosphingobium aromaticivorans

<400> SEQUENCE: 21

```
gtgaagaccc aggtcgccat catcggcgcc ggccctgccg gcctgctcct cggacatctg      60
ctcaaggccg aaggcatcga ctgcgtcgtg ctggaacggc agacgcccga ttacgtcctc     120
ggccgcatcc gcgccggcgt gctcgaacag atcacggtcg ggctcatgga acgcctcggc     180
ctcgacgcgc gcctcaaggc cgagggcctt gtcgaggaag gcttcaacct ggccgacggc     240
gaacgcctga tccgcatcga cgtcgccaat ctcaccggca agaccgtggt cgtctacggc     300
cagaccgaga tcaccaagga cctcatggac gccgctcccg aacgcgggtt gcaggtcatc     360
tatggcgcca cgcgaggtcg cgctcttcga catcgagagcg atgccccta cgtcacctac     420
gtgcatgatg gcgcccccg ccgcatcgat gcccgcttca tcgtaggctg cgacggcttc     480
```

```
cacggaccca gccgcaaggc cattccggcc agcgtcgcgc gcgagtacga gcgggtctat    540
ccgttcggct ggctcggcat cctcgccgac gttccgcctt gcaaccacga gctgatctac    600
gccaatcacg agcgcgggtt cgccctcgcc tcgatgcgca gccacacgcg cagccgctat    660
tacgtggacg tcccgctgac cgaaaaggtc gaggactggt cggacgagcg catctgggac    720
gaactggccg tgcgccttgg ccctgaagcc gccgccaaca tcacgcgcgg gccttcgatc    780
gagaagtcga tcgcgcccct cgctcctac gtgttcgaac cgatgcgcca cggcagcctg    840
ctgctctgcg gcgatgccgc gcatatcgtg ccgccgaccg cgccaaggg cctcaacctt    900 gcggccagcg acgtccacta tgccgccgaa gccctgaccg gcttcttcaa gcgcgccgac    960
aacgatgcag tgccccggta ctcggcaaag gcgctcgccc gcgtctggaa atccgaacgc   1020
ttctcgtggt cgctgaccaa gctgatgcac cgtttccccg aggacggccc gttcgaacgc   1080
gccatgcagg tggccgaact ggagtacatc gcaaccagca aggcggccca gaccagcatc   1140
gcggaaaact acgtcggcct gccggtctga                                    1170

<210> SEQ ID NO 22
<211> LENGTH: 389
<212> TYPE: PRT
<213> ORGANISM: Novosphingobium aromaticivorans

<400> SEQUENCE: 22

Met Lys Thr Gln Val Ala Ile Ile Gly Ala Gly Pro Ala Gly Leu Leu
1               5                   10                  15

Leu Gly His Leu Leu Lys Ala Glu Gly Ile Asp Cys Val Val Leu Glu
                20                  25                  30

Arg Gln Thr Pro Asp Tyr Val Leu Gly Arg Ile Arg Ala Gly Val Leu
            35                  40                  45

Glu Gln Ile Thr Val Gly Leu Met Glu Arg Leu Gly Leu Asp Ala Arg
        50                  55                  60

Leu Lys Ala Glu Gly Leu Val Glu Gly Phe Asn Leu Ala Asp Gly
65                  70                  75                  80

Glu Arg Leu Ile Arg Ile Asp Val Ala Asn Leu Thr Gly Lys Thr Val
                85                  90                  95

Val Val Tyr Gly Gln Thr Glu Ile Thr Lys Asp Leu Met Asp Ala Ala
            100                 105                 110

Pro Glu Arg Gly Leu Gln Val Ile Tyr Gly Ala Ser Glu Val Ala Leu
        115                 120                 125

Phe Asp Ile Glu Ser Asp Ala Pro Tyr Val Thr Tyr Val His Asp Gly
    130                 135                 140

Ala Pro Arg Arg Ile Asp Ala Arg Phe Ile Val Gly Cys Asp Gly Phe
145                 150                 155                 160

His Gly Pro Ser Arg Lys Ala Ile Pro Ala Ser Val Ala Arg Glu Tyr
                165                 170                 175

Glu Arg Val Tyr Pro Phe Gly Trp Leu Gly Ile Leu Ala Asp Val Pro
            180                 185                 190

Pro Cys Asn His Glu Leu Ile Tyr Ala Asn His Glu Arg Gly Phe Ala
        195                 200                 205

Leu Ala Ser Met Arg Ser His Thr Arg Ser Arg Tyr Tyr Val Asp Val
    210                 215                 220

Pro Leu Thr Glu Lys Val Glu Asp Trp Ser Asp Glu Arg Ile Trp Asp
225                 230                 235                 240

Glu Leu Ala Val Arg Leu Gly Pro Glu Ala Ala Ala Asn Ile Thr Arg
```

```
                    245                 250                 255
Gly Pro Ser Ile Glu Lys Ser Ile Ala Pro Leu Arg Ser Tyr Val Phe
            260                 265                 270

Glu Pro Met Arg His Gly Ser Leu Leu Cys Gly Asp Ala Ala His
        275                 280                 285

Ile Val Pro Pro Thr Gly Ala Lys Gly Leu Asn Leu Ala Ala Ser Asp
        290                 295                 300

Val His Tyr Ala Ala Glu Ala Leu Thr Gly Phe Phe Lys Arg Ala Asp
305                 310                 315                 320

Asn Asp Ala Val Pro Arg Tyr Ser Ala Lys Ala Leu Ala Arg Val Trp
                325                 330                 335

Lys Ser Glu Arg Phe Ser Trp Ser Leu Thr Lys Leu Met His Arg Phe
            340                 345                 350

Pro Glu Asp Gly Pro Phe Glu Arg Ala Met Gln Val Ala Glu Leu Glu
        355                 360                 365

Tyr Ile Ala Thr Ser Lys Ala Ala Gln Thr Ser Ile Ala Glu Asn Tyr
        370                 375                 380

Val Gly Leu Pro Val
385

<210> SEQ ID NO 23
<211> LENGTH: 945
<212> TYPE: DNA
<213> ORGANISM: Novosphingobium aromaticivorans

<400> SEQUENCE: 23
atgcgtatcg cactggccgg ggcgggagcc ttcggcgaaa agcacctcga tggcctgaag      60
aacatcgatg gcgtcgagat cacctcgatc atcagccgta ccggcgagca ggctgcggcc     120
gtcgccgcca agtatggcgc gaagcattcc tcgaccgagc tcgaggatgc cctggcgcgc     180
gacgacgtcg acgcggtgat cctgtgcacg ccgacgcaga tgcacgcatc gcaggccatc     240
gcctgcatga aggcgggcaa gcacgtgcag gtcgagatcc cgctggccga cagctgggcg     300
gattcgcagg aagttctgcg ggtgcagcag gaaacgggca aggtctgcat ggtcggccat     360
acccgccgct tcaatccgag ccaccagttc gtgcacaacc ggatcaaggc gggcgagttc     420
aacgtccagc agatggacgt gcagacctac ttcttccgcc gcaagaacat caacgccaag     480
ggcgagccgc gttcgtggac cgaccacctg ttgtggcacc acgccgcgca cggtggac      540 ctgttcgcct accaggcggg caggatcgtc aaggccaatg cggtggaagg gccgatccat     600
cccgagcttg catcgcgat ggacatgtcg atccagctca agagcgagac cggcgcgatc      660
tgcaccctgt cgctttcgtt caacaacgac gggccgctgg gcaccttctt ccgctacatc     720
ggcgataccg cgacctacat cgcgcgctac gacgacctgg tgaatggcaa ggaggagccg     780
atcgacgtgt ccaaggtcga cgtcagcatg aacggcatcg aattgcagga ccgcgaattc     840
gtcgccgcga tccgcgaggg cgcgcgagcc aacagctcgg tgcagaaggt cttcgactgc     900
taccgcgtgc tgggcgagct ggagcagcag ctggccaagg gttga                    945

<210> SEQ ID NO 24
<211> LENGTH: 314
<212> TYPE: PRT
<213> ORGANISM: Novosphingobium aromaticivorans

<400> SEQUENCE: 24

Met Arg Ile Ala Leu Ala Gly Ala Gly Ala Phe Gly Glu Lys His Leu
1               5                   10                  15
```

Asp Gly Leu Lys Asn Ile Asp Gly Val Glu Ile Thr Ser Ile Ile Ser
            20                  25                  30

Arg Thr Gly Glu Gln Ala Ala Val Ala Ala Lys Tyr Gly Ala Lys
    35                  40                  45

His Ser Ser Thr Glu Leu Glu Asp Ala Leu Ala Arg Asp Asp Val Asp
50                  55                  60

Ala Val Ile Leu Cys Thr Pro Thr Gln Met His Ala Ser Gln Ala Ile
65                  70                  75                  80

Ala Cys Met Lys Ala Gly Lys His Val Gln Val Glu Ile Pro Leu Ala
                85                  90                  95

Asp Ser Trp Ala Asp Ser Gln Glu Val Leu Arg Val Gln Gln Glu Thr
            100                 105                 110

Gly Lys Val Cys Met Val Gly His Thr Arg Arg Phe Asn Pro Ser His
    115                 120                 125

Gln Phe Val His Asn Arg Ile Lys Ala Gly Glu Phe Asn Val Gln Gln
130                 135                 140

Met Asp Val Gln Thr Tyr Phe Phe Arg Arg Lys Asn Ile Asn Ala Lys
145                 150                 155                 160

Gly Glu Pro Arg Ser Trp Thr Asp His Leu Leu Trp His His Ala Ala
                165                 170                 175

His Thr Val Asp Leu Phe Ala Tyr Gln Ala Gly Arg Ile Val Lys Ala
            180                 185                 190

Asn Ala Val Glu Gly Pro Ile His Pro Glu Leu Gly Ile Ala Met Asp
    195                 200                 205

Met Ser Ile Gln Leu Lys Ser Glu Thr Gly Ala Ile Cys Thr Leu Ser
210                 215                 220

Leu Ser Phe Asn Asn Asp Gly Pro Leu Gly Thr Phe Phe Arg Tyr Ile
225                 230                 235                 240

Gly Asp Thr Ala Thr Tyr Ile Ala Arg Tyr Asp Asp Leu Val Asn Gly
                245                 250                 255

Lys Glu Glu Pro Ile Asp Val Ser Lys Val Asp Val Ser Met Asn Gly
            260                 265                 270

Ile Glu Leu Gln Asp Arg Glu Phe Val Ala Ala Ile Arg Glu Gly Arg
    275                 280                 285

Glu Pro Asn Ser Ser Val Gln Lys Val Phe Asp Cys Tyr Arg Val Leu
290                 295                 300

Gly Glu Leu Glu Gln Gln Leu Ala Lys Gly
305                 310

<210> SEQ ID NO 25
<211> LENGTH: 1134
<212> TYPE: DNA
<213> ORGANISM: Novosphingobium aromaticivorans

<400> SEQUENCE: 25
atgtccgtgg tcaatccatc agaacaatcg attgcctcgt ttggcgcgac gccgtggcgt      60
cccgcaggct acggccagag cgcccggatt ccgctcatcg aagccgccga tgtcgtgcgc     120
ctcttcgacg acctggacct gtgggactgc tggcccctcg cgcacgagga cgggcgtacg     180
gttgagcatc tggacgcaa ctggtggttc tttctttcgg cgccggtctt ccccgatccg      240
gtcgaacggc atggccatgc ccgcatccgc ctcgtctcgc tggggaggga tggatggaag     300
gatcacggca cgcctttcc cgatggtctc acgcccggca gccgcgaatg ggcgggttcg      360
gccgtgctga tggacgacgg cgcaccgtg cagcatttct tcaccgccgc aggacggcgc      420

```
ggcgaggctg caccgacctt cgagcaacgc atattcgtca gcgaaggcac cctgaccgag    480
gccggccctg gcggatggca agccccgcgc gagatattcg aggccgatgg cctacgctac    540
gtgctcgacc ggcaggacag tggggcgccg gccagatca agggttttcg cgatcccgcg     600
tggcttcgag atccgccac cggcagggcg cacatcctgt tcaccggcag cgccgcatgg     660
tcggatcatc ctttcaacgg caatgtgggg atcgccacgc tcgagggtga cacctgggtt    720
ctcggcaatc cactggtcga ggcgatcgac gtgaacaacg agcttgaacg ccgcacatc    780
ctggtgcgcg acgggctgta ctatctcttc tggtcgaccc agacccacac tttcgcgccc    840
gctgcggtgg cagggcccaa cggcctctac ggcatggtgg ctgaaagcct tgcgggcccc    900
tggcgcatgc tcaacgaagg cgggctggtc gcggcgaacc cggatgcgga agcaaagcag    960
tcctacagtt ggtgggtcac cggcgagggc gaagtgtgga gcttcgtcga ctactggggc   1020
atggcagggc gcaccgtcga ggagcaaccc gaattgctgc gcagcaattt cggggaacc   1080
cccgcacctc ggttcatgct taacttcgat ggcgagcggg tcaccatcgc ctga         1134
```

<210> SEQ ID NO 26
<211> LENGTH: 377
<212> TYPE: PRT
<213> ORGANISM: Novosphingobium aromaticivorans

<400> SEQUENCE: 26

```
Met Ser Val Val Asn Pro Ser Glu Gln Ser Ile Ala Ser Phe Gly Ala
1               5                   10                  15

Thr Pro Trp Arg Pro Ala Gly Tyr Gly Gln Ser Ala Arg Ile Pro Leu
            20                  25                  30

Ile Glu Ala Ala Asp Val Val Arg Leu Phe Asp Asp Leu Asp Leu Trp
        35                  40                  45

Asp Cys Trp Pro Leu Ala His Glu Asp Gly Arg Thr Val Glu His Leu
    50                  55                  60

Gly Arg Asn Trp Trp Phe Phe Leu Ser Ala Pro Val Phe Pro Asp Pro
65                  70                  75                  80

Val Glu Arg His Gly His Ala Arg Ile Arg Leu Val Ser Leu Gly Glu
                85                  90                  95

Asp Gly Trp Lys Asp His Gly Asn Ala Phe Pro Asp Gly Leu Thr Pro
            100                 105                 110

Gly Ser Arg Glu Trp Ala Gly Ser Ala Val Leu Met Asp Asp Gly Arg
        115                 120                 125

Thr Val Gln His Phe Phe Thr Ala Ala Gly Arg Arg Gly Glu Ala Ala
    130                 135                 140

Pro Thr Phe Glu Gln Arg Ile Phe Val Ser Glu Gly Thr Leu Thr Glu
145                 150                 155                 160

Ala Gly Pro Gly Gly Trp Gln Ala Pro Arg Glu Ile Phe Glu Ala Asp
                165                 170                 175

Gly Leu Arg Tyr Val Leu Asp Arg Gln Asp Ser Gly Ala Pro Gly Gln
            180                 185                 190

Ile Lys Gly Phe Arg Asp Pro Ala Trp Leu Arg Asp Pro Ala Thr Gly
        195                 200                 205

Arg Ala His Ile Leu Phe Thr Gly Ser Ala Ala Trp Ser Asp His Pro
    210                 215                 220

Phe Asn Gly Asn Val Gly Ile Ala Thr Leu Glu Gly Asp Thr Trp Val
225                 230                 235                 240

Leu Gly Asn Pro Leu Val Glu Ala Ile Asp Val Asn Asn Glu Leu Glu
```

```
            245                 250                 255
Arg Pro His Ile Leu Val Arg Asp Gly Leu Tyr Tyr Leu Phe Trp Ser
            260                 265                 270

Thr Gln Thr His Thr Phe Ala Pro Ala Ala Val Ala Gly Pro Asn Gly
        275                 280                 285

Leu Tyr Gly Met Val Ala Glu Ser Leu Ala Gly Pro Trp Arg Met Leu
    290                 295                 300

Asn Glu Gly Gly Leu Val Ala Ala Asn Pro Asp Ala Glu Ala Lys Gln
305                 310                 315                 320

Ser Tyr Ser Trp Trp Val Thr Gly Glu Gly Glu Val Trp Ser Phe Val
            325                 330                 335

Asp Tyr Trp Gly Met Ala Gly Arg Thr Val Glu Glu Gln Pro Glu Leu
            340                 345                 350

Leu Arg Ser Asn Phe Gly Gly Thr Pro Ala Pro Arg Phe Met Leu Asn
        355                 360                 365

Phe Asp Gly Glu Arg Val Thr Ile Ala
    370                 375

<210> SEQ ID NO 27
<211> LENGTH: 51
<212> TYPE: DNA
<213> ORGANISM: Artificial Sequence
<220> FEATURE:
<223> OTHER INFORMATION: Saro2819_Del-R Primer

<400> SEQUENCE: 27
gcgccaatcc ataccacgga ttatgcgaat actactccat ccatcagctt g          51

<210> SEQ ID NO 28
<211> LENGTH: 56
<212> TYPE: DNA
<213> ORGANISM: Artificial Sequence
<220> FEATURE:
<223> OTHER INFORMATION: Saro2819-pK18_Amp-F Primer

<400> SEQUENCE: 28
cgattcatta atgcagctgg cacgacagga gcgaatggca tgagttcaca ttcagc      56

<210> SEQ ID NO 29
<211> LENGTH: 51
<212> TYPE: DNA
<213> ORGANISM: Artificial Sequence
<220> FEATURE:
<223> OTHER INFORMATION: Saro2819_Del-F Primer

<400> SEQUENCE: 29
gctgatggat ggagtagtat tcgcataatc cgtggtatgg attggcgcat g           51

<210> SEQ ID NO 30
<211> LENGTH: 56
<212> TYPE: DNA
<213> ORGANISM: Artificial Sequence
<220> FEATURE:
<223> OTHER INFORMATION: Saro2819-pK18_Amp-R Primer

<400> SEQUENCE: 30
gtttctgcgg actggctttc tagatgttcc tgcatggtct ggtcctgttc aagcag      56

<210> SEQ ID NO 31
<211> LENGTH: 37
<212> TYPE: DNA
<213> ORGANISM: Artificial Sequence
```

```
<220> FEATURE:
<223> OTHER INFORMATION: Saro2864-5Del R Primer

<400> SEQUENCE: 31
gggtagtctg gatcattcag actcgcatgg tgccgag                              37

<210> SEQ ID NO 32
<211> LENGTH: 55
<212> TYPE: DNA
<213> ORGANISM: Artificial Sequence
<220> FEATURE:
<223> OTHER INFORMATION: Saro2864-5-pK18_Amp_F Primer

<400> SEQUENCE: 32
cgattcatta atgcagctgg cacgacagca ggtcggcttc aaggaggaag ttctg          55

<210> SEQ ID NO 33
<211> LENGTH: 39
<212> TYPE: DNA
<213> ORGANISM: Artificial Sequence
<220> FEATURE:
<223> OTHER INFORMATION: Saro2864-5_Del_F Primer

<400> SEQUENCE: 33
ccatgcgagt ctgaatgatc cagactaccc gccgttatc                            39

<210> SEQ ID NO 34
<211> LENGTH: 57
<212> TYPE: DNA
<213> ORGANISM: Artificial Sequence
<220> FEATURE:
<223> OTHER INFORMATION: Saro2864-5-pK18_Amp_R Primer

<400> SEQUENCE: 34
gtttctgcgg actggctttc tagatgttcg accactatgc aatggaatgg aacctgc        57

<210> SEQ ID NO 35
<211> LENGTH: 20
<212> TYPE: DNA
<213> ORGANISM: Artificial Sequence
<220> FEATURE:
<223> OTHER INFORMATION: Saro2865_Start-SNP_F Primer

<400> SEQUENCE: 35
ggcatgctcg gcaccatgcg                                                 20

<210> SEQ ID NO 36
<211> LENGTH: 21
<212> TYPE: DNA
<213> ORGANISM: Artificial Sequence
<220> FEATURE:
<223> OTHER INFORMATION: Saro2865_Start-SNP_R2 Primer

<400> SEQUENCE: 36
gccgtcgacc gcgagagctt g                                               21
```